US008586354B2

(12) United States Patent
Holm

(10) Patent No.: US 8,586,354 B2
(45) Date of Patent: *Nov. 19, 2013

(54) ADENOVIRUSES, NUCLEIC ACIDS THAT CODE FOR THE SAME AND THE USE OF SAID VIRUSES

(76) Inventor: Per Sonne Holm, Furstenfeldbruck (DE)

(*) Notice: Subject to any disclaimer, the term of this patent is extended or adjusted under 35 U.S.C. 154(b) by 72 days.

This patent is subject to a terminal disclaimer.

(21) Appl. No.: 12/690,729

(22) Filed: Jan. 20, 2010

(65) Prior Publication Data

US 2010/0297731 A1 Nov. 25, 2010

Related U.S. Application Data

(63) Continuation of application No. 10/579,543, filed as application No. PCT/EP2004/012931 on Nov. 15, 2004, now abandoned.

(30) Foreign Application Priority Data

Nov. 14, 2003 (DE) .................................. 103 53 152
Apr. 14, 2004 (DE) .......................... 10 2004 018 117

(51) Int. Cl.
*C12N 15/63* (2006.01)
*C12N 15/11* (2006.01)
*A61K 35/00* (2006.01)

(52) U.S. Cl.
USPC ....................... 435/320.1; 536/23.1; 424/93.1

(58) Field of Classification Search
USPC ....................... 435/320.1; 536/23.1; 424/93.1
See application file for complete search history.

(56) References Cited

U.S. PATENT DOCUMENTS

| 5,998,205 | A | 12/1999 | Hallenbeck et al. |
| 2003/0095989 | A1 | 5/2003 | Irving et al. |
| 2004/0067586 | A1 | 4/2004 | Holm |
| 2010/0330037 | A1 | 12/2010 | Holm |

FOREIGN PATENT DOCUMENTS

| WO | 95/34671 | A1 | 12/1995 |
| WO | 02/053711 | A2 | 7/2002 |

OTHER PUBLICATIONS de Felipe et al, (Genet Vaccines Ther. Sep. 13, 2004;2(1):13).*
Steenenga et al, (Molecular and Cellular Biology, 19(5): 3885-3894, 1999).
Li et al, (Cancer Research, 61: 6428-6436, 2001).
John A. Howe et al., Evaluation of El-Mutan Adenoviruses as Conditionally Replicating Agents for Cancer Therapy, Molecular Therapy vol. 2, 485-95, (Nov. 2000).
Judith Clancy Keen et al., A novel histone deacetylase inhibitor, Scriptaid, enhances expression of functional estrogen receptor α (ER) in ER negative human breast cancer cells in combination with 5-aza 2'-deoxycytidine, Breast Cancer Research and Treatment vol. 81, 177-86, (2003).
Ann E. Tollefson et al., The Adenovirus Death Protein (E3-11.6K) Is Required at Very Late Stages of Irifection for Efficient Cell Lysis and Release of Adenovirus from Infected Cells, J. of Virology ,vol. 70, 2296-2306 (Apr. 1996).
Athina Efthymiadis, Lyndall J. Briggs, and David A. Jans, The HIV-1 Tat Nuclear Localization Sequence Confers Novel Nuclear Import Properties, J . of Biological Chemistry, vol. 273 No. 3, 1623-28 (Jan. 1998).
Silke Weigel and Matthias Dobbelstein, The Nuclear Export Signal within the E4orf6 Protein of Adenovirus Type 5 Supports Virus Replication and Cytoplasmic Accumulation of Viral rnRNA, J . of Virology, vol. 74 No. 2, 764-72 (Jan. 2000).
Ching-Yi Chen et al., Nucleolin and YB-1 are required for JNK-mediated interleukin-2 mRNA stabilization during T-cell activation, Genes & Development, vo1. 14, 1236-48 (2000).
Takefumi Ohga, et al., Role of the Human Y Box-binding Protein YB-1 in Cellular Sensitivity to the DNA-damaging Agents Cisplatin, Mitomycin C, and Ultraviolet Light, Cancer Research , vol. 56, 4224-28 (Sep. 1996).
Hiroto Izumi et al., Y box-binding protein-1 binds preferentially to single-stranded nucleic acids and exhibits 3'-5' exonuclease activity, Nucleic Acid Research, vol. 29 No. 5, 1200-07 (2001).
Injae Chung et al., Use of L-plastin promoter to develop an adenoviral system that confers transgene expression in ovarian cancer cells but not in normal mesothelial cells, Cancer Gene Therapy, vol. 6 No. 2, 99-106 (1999).
Ilana Braunstein, et al., Human Telomerase Reverse Transcriptase Promoter Regulation in National and Malignant Human Ovarian Epithelial Cells, Cancer Research, vol. 61, 5529-36 (Jul. 2001).
Sandor, V., et al., "Phase I trial of the histone deacetylase inhibitor, depsipeptide (FR901228, NSC 630176), in patients with refractory neoplasms", Clinical Cancer Research, vol. 8, pp. 718-728, Mar. 2002.
Goldsmith, M.E., et al., "The histone deacetylase inhibitor FK228 preferentially enhances adenovirus transgene expression in malignant cells," Clinical Cancer Research, vol. 9, pp. 5394-5401, Nov. 1, 2003.
Steenenga et al, (Molecular and Cellular Biology, 19(5):3885-3894, 1999).
Li et al, (Cancer Research, 61:6428-6436, 2001).
Fadlo R. Khuri et al., A controlled trial of intraturnoral ONYX-015, Nature Medicine 6, 879-85, (Aug. 2000).
John A. Howe et al., Evaluation of El-Mutan Adenoviruses as Conditionally Replicating Agents for Cancer Therapy, Molecular Therapy vol. 2, 485-95, (Nov. 2000).
Cristina Balague' et al., Human Papillormavirus E6E7-Mediated Adenovirus Cell Killing, J. of Virology vol. 75 No. 16, 7602-1 1, (Aug. 2001).
Ulrike Stein et al., Hyperthermia-induced Nuclear Translocation of Transcription Factor YB-I Leads to Enhanced Expression of Multidrug Resistance-related ABC Transporters, J. of Biological Chemistry, vol. 276 No. 30, 28562-69, (Jul. 2001).
Scott M. Wilhelm et al., Bay 43-9006 Exhibits Broad Spectrum Oral Antitumor Activity and Targets the RAF/MEK/ERK Pathway and Receptor Tyrosirze Kirzases Involved in Tumor Progression and Angiogenesis, Cancer Research. 64, 7099-109, (Oct. 2004).

(Continued)

*Primary Examiner* — Gerald Leffers, Jr.
*Assistant Examiner* — Magdalene Sgagias
(74) *Attorney, Agent, or Firm* — Lisa V. Mueller; Michael Best & Friedrich, LLP

(57) ABSTRACT

The present invention is related to an adenovirus expressing a first protein which is selected from the group comprising an E1B protein and an E4 protein, prior to a second protein which is selected from the group comprising an E1A protein.

14 Claims, 33 Drawing Sheets

(56) References Cited

OTHER PUBLICATIONS

Andrew Fribley et al., Proteasome Inhibitor PS-341 Induces Apoptosis through Induction of Endoplasmic Reticulum Stress-Reactive Oxygen Species in Head and Neck Squamous Cell Carcinoma Cells, Molecular and Cellular Biology vol. 24 No. 22, 9695-704 (Nov. 2004).
Kevin Camphausen et al., Enlzancernent of Xenograft Tumor Radiosensitivity by the Histone Deacetylase Inhibitor MS-275 and Correlation with Histone Hyperacetylation, Clinical Cancer Research, vol. 10, 6066-71 (Sep. 2004).
Sylvie Wittman et al., Flavopiridol Down-Regulates Antiapoptotic Proteins and Sensitizes Human Breast Cancer Cells to Epothilone B-induced Apoptosis, Cancer Research vol. 63, 93-99 (Jan. 2003).
Judith Clancy Keen et al., A novel histone deacetylase inhibitor, Scriptaid, enhances expression of functional estrogen receptor α (ER) in ER negative human breast cancer cells in combination with 5-aza 2'-deoxycytidine, Breast Cancer Research and Treatment vol. 81, 177-86, (2003).
Seong Hwan Kim et al., Apicidin is a histone deacetylase inhibitor with anti-invasive and anti-angiogenic potentials, Biochemical and Biophysical Research Communications vol. 3 15, 964-70, (2004).
Emmanuelle Querido et al., Identification of Three Functions of the Adenoovirus E4orf6 Protein That Mediate p53 Degradation by the E4orf6-EIB55K Complex, J. of Virology, vol. 75 No. 2, 699-709, (Jan. 2001).
Pierre A. Boulanger and Eric G. Blair, Expression and interactions of human adenovirus oncoproteins, Biochemistry J. vol. 275, 281-99 (1991).
Joan A. Howe et al., Evaluations of E1-Mutant Adenoviruses as Conditionally Replicating Agents for Cancer Therapy, Molecular Therapy vol. 2, 485-95 (Nov. 2000).
W.C. Russell, Update on adenovirus and its vectors, J. of Virology, vol. 81, 2573-2604 (2000).
Ann E. Tollefson et al., The Adenovirus Death Protein (E3-11.6K) Is Required at Very Late Stages of Irifection for Efficient Cell Lysis and Release of Adenovirus from Infected Cells, J. of Virology, vol. 70, 2296-2306 (Apr. 1996).
Ramya Sundararajan and Eileen White, E1B 19K Blocks Bax Oligomerization and Tumor Necrosis Factor Alpha-Medicated Apoptsis, J. of Virology, vol. 75 No. 16, 7506-16 (Aug. 2001).
V. Descamps et al., Strategies for cancer gene therapy using adenoviral vectors, J. Mol. Med., vol. 74, 183-89 (1996).
Anish Sen Majumdar et al., Efficacy of herpes simplex virus thymidine kinase in combination with cytokine gene therapy in an experimental inetastatic breast cancer model, Cancer Gene Therapy, vol. 7 No. 7, 1086-99 (2000).
Xinqiao Zhang et al., Adenoviral-mediated Retinoblastoma 94 Produces Rapid Telomere Erosion, Chromosomal Crisis, and Caspase-dependent Apoptosis in Bladder Cancer and Immortalized Human Urothelial Cells but not in Normal Urothlial Cells, Cancer Research, vol. 63, 760-65 (Feb. 2003).
Karoly Toth et al., Radiation increases the activity of oncolytic adenovirus cancer gene therapy vectors that overexpress the ADP (E3-11.6K) protein, Cancer Gene Therapy, vol. 10, 193-200 (2003).
T. Yamaguchi et al., Enhancement of thymidine kinase-mediated killing of malignant glioma by BimS, a BH3-only cell death activator, Gene Therapy, vol. 10, 375-85 (2003).
Lin Ji et al., Induction of Apoptosis and Inhibition of Tumorigenicity and Tumor Growth by Aderzovirus vector-mediated Fragile Histidine Triad (FHIT) Gene Overexpression, Cancer Research, vol. 59, 3333-39 (Jul. 1999).
Zao-Zhong Su et al., Melanoma differentiation associated gene- 7, mda- 7/IL-24, selectively induces growth suppression, apoptosis and radiosensitization in malignant gliomas in a p53-independent manner, Oncogene, vol. 22, 1164-1180 (2003).
Matti Ahonen et al., Antihumor Activity and Bystander effect of Adenovirally Delivered Tissue Inhibitor of Metalloproteinases-3, Molecular Therapy, vol. 5 No. 6, 705-15, (Jun. 2002).
Gerald A. Soff et al., Expression of Plasminogen Activator Inhibitor Type 1 by Human prostate Carcinoma Cells Inhibits Primary Tumor Growth, Tumor-associated Angiogenesis, arzd Metastasis to Lung and Liver in an Athyymic Mouse Model, J. Clinical Investigation, vol. 96, 2593-2600 (Dec. 1995).
Athina Efthymiadis, Lyndall J. Briggs, and David A. Jans, The HIV-1 Tat Nuclear Localization Sequence Confers Novel Nuclear Import Properties, J. of Biological Chemistry, vol. 273 No. 3, 1623-28 (Jan. 1998).
Joann Tufariello, Sangho Cho, and Marshall S. Horwitz, The Adenovirus E3 14.7-Kilodalton Protein Which Inhibits Cytolusis by Tumor Necrosis Factor Increases the Virulence of Vaccinia Virus in a Murine Pneumonia Model, J. of Virology, vol. 68 No. 1, 453-62 (Jan. 1994).
Anna-Marija Helt and Denise A. Galloway, Mechanisms by which DNA tumor oncoproteins target the Rb family of pocket proteins, Carcinogenesis, vol. 24 No. 2, 159-69 (2003).
Sathyamangalam Swaminathan and BayarThimmapaya, Transactivation of Adenovirus E2-early Promoter by E1A and E4 6/7 in the Context of Viral Chromosome, J. Molecular Biology, vol. 258, 736-46 (1996).
Wilma T. Steegenga, et al., The large E1B protein together with the E4orf6 protein target p53 for active degredation in adenovirus infected cells, Oncogene, vol. 16, 349-57 (1998).
Konstantin Doronin et al., Tumor-Specific, Replication-Competent Adenovirus Vectors Overexpressing the Adenovirus Death Protein, J. of Virology, vol. 74 No. 13, 6147-55 (2000).
Pierre A. Boulanger, and G. Eric Blair; Expression and interactions of human adenovirus oncoproteins, Biochemistry J. vol. 275, 281-99 (1991).
Silke Weigel and Matthias Dobbelstein, The Nuclear Export Signal within the E4orf6 Protein of Adenovirus Type 5 Supports Virus Replication and Cytoplasmic Accumulation Of Viral rnRNA, J. of Virology, vol. 74 No. 2, 764-72 (Jan. 2000).
Keith N. Leppard, Regulated RNA Processing and RNA Transport during Adenovirus Infection, Seminars in Virology, vol. 8, 301-07 (1998).
Peter R. Mertens et al., Glomerular Mesangial Cell-specific Transactivation of Matrix Metalloproteinase 2 Transcription Is Mediated by YB-1, J. of Biological Chemistry, vol. 272 No. 36, 22905-12 (1997).
Ching-Yi Chen et al., Nucleolin and YB-1 are required for JNK-mediated interleukin-2 mRNA stabilization during T-cell activation, Genes & Development, vol. 14, 1236-48 (2000).
Takefumi Ohga, et al., Role of the Human Y Box-binding Protein YB-1 in Cellular Sensitivity to the DNA-damaging Agents Cisplatin, Mitomycin C, and Ultraviolet Light Cancer Research, vol. 56, 4224-28 (Sep. 1996).
Hiroto Izumi et al., Y box-binding protein-1 binds preferentially to single-stranded nucleic acids and exhibits 3'-5' exonuclease activity, Nucleic Acid Research, vol. 29 No. 5, 1200-07 (2001).
Per S. Holm et al. YB-1 Relocates to the Nucleus in Adenovirus-infected Cells and Facilitates Viral Replication by Inducing E2 Gene Expression through the E2 Late Promoter J. of Biological Chemistry, vol. 277 No. 12, 10427-34 (Mar. 2002).
Felicia D. Goodrum and David A. Ornelies, Roles for the E4 orf6, orf3, and E1B 55-Kilodalton Proteins in Cell Cycle-Independent Adenovirus Replication, J. of Virology, vol. 73 No. 9, 7474-88 (Sep. 1999).
David M. Vigushin et al., Trichostatin A Is a Histone Deacetylase Inhibitor with Potent Antitumor Activity against Breast Cancer in Vivo, Clinical Cancer Research, vol. 7, 971-76 (Apr. 2001).
Masaki Kitazono et al., Enhanced Adenovirus Transgene Expression in Malignant Cells Treated with the Histone Deacetylase Inhibitor, Cancer Research, vol. 61, 6328-30 (Sep. 2001).
Jerry Jaboin et al., MS-27-275, an Inhibitor of Histone Deacetylase, Has Marked in Vitro and in Vivo Antitumor Activity against Pediatric Solid Tumors, Cancer Research, vol. 62, 6108-15 (Nov. 2002).
Peter Atadja et al., Selective Growth Inhibition of Tumor Cells by a Novel Histone Deacetylase Inhibitor, NVP-LAQ824, Cancer Research, vol. 64, 689-95 (Jan. 2004).
Mark R. Gilbert et al., Phase I Clinical and Pharmacokinetic Study of Irinotecan in Adults with Recurrent Malignant Glioma, Clinical Cancer Research, vol. 9, 2940-49 (Aug. 2003).

(56) References Cited

OTHER PUBLICATIONS

Rajeev Rajendra et al., Differential Effects of the Breast Cancer Resistance Protein on the Cellular Accumulation and Cytotoxicity of 9-Aminocamptothecin and 9-Nitrocamptothecin, Cancer Research, vol. 63, 3228-33 (Jun. 2003).

Monica Binaschi et al., Relationship between Lethal Effects and Topoisomerase 11-Mediated Double-Stranded DNA Breaks Produced by Anthracyclines with Different Sequence Specificity, Molecular Pharmacology, vol. 51, 1053-59 (1997).

Injae Chung at al., Use of L-plastin promoter to develope an adenoviral system that confers transgene expression in ovarian cancer cells but not in normal mesothelial cells, Cancer Gene Therapy, vol. 6 No. 2, 99-106 (1999).

Ilana Braunstein et al., Human Telomerase Reverse Transcriptase Promoter Regulation in National and Malignant Human Ovarian Epithelial Cells, Cancer Research, vol. 61, 5529-36 (Jul. 2001).

AS Majumdar et al., The telomerase reverse transcriptase promoter drives efficacious tumor suicide gene therapy while preventing hepatotixicity encountered with constitutive promoters, Gene Therapy, vol. 8, 568-78 (2001).

Matthias Dobbelstein et al., Nuclear export of the E1B 55k-Da and E4 34-kDa adenoviral oncoproteins mediated by a rev-like signal sequence, The EMBO J., vol. 16 No. 14, 4276-84 (1997).

Stuart A. Nicklin et al., Ablating Adenovirus Type 5 Fiber-CAR Binding and HI Loop Insertion of the SIGYPLP Peptide Generate an Endothlial Cell-Selective Adenovirus, Molecular Therapy, vol. 4 No. 6, 534-42 (Dec. 2001).

Henry K. Wong and Edward B. Ziff, Complementary Functions of E1a Conserved Region 1 Cooperate with Conserved Region 3 to Activate Adenovirus Serotype 5 Early Promoters, J. of Virology, vol. 68 No. 8, 4910-20 (Aug. 1994).

\* cited by examiner

Fig. 16
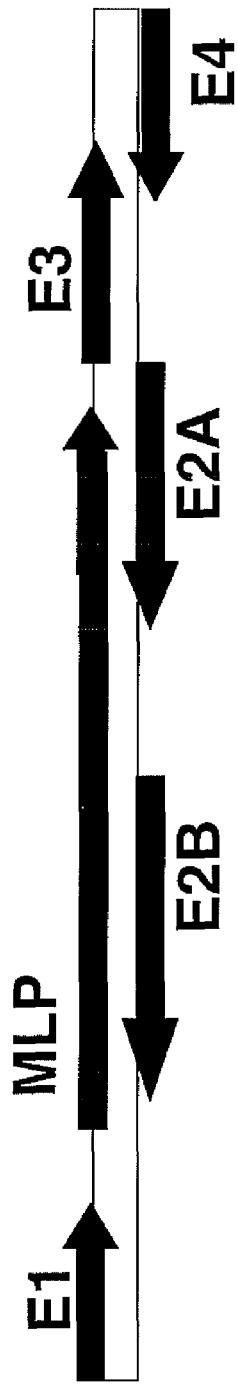
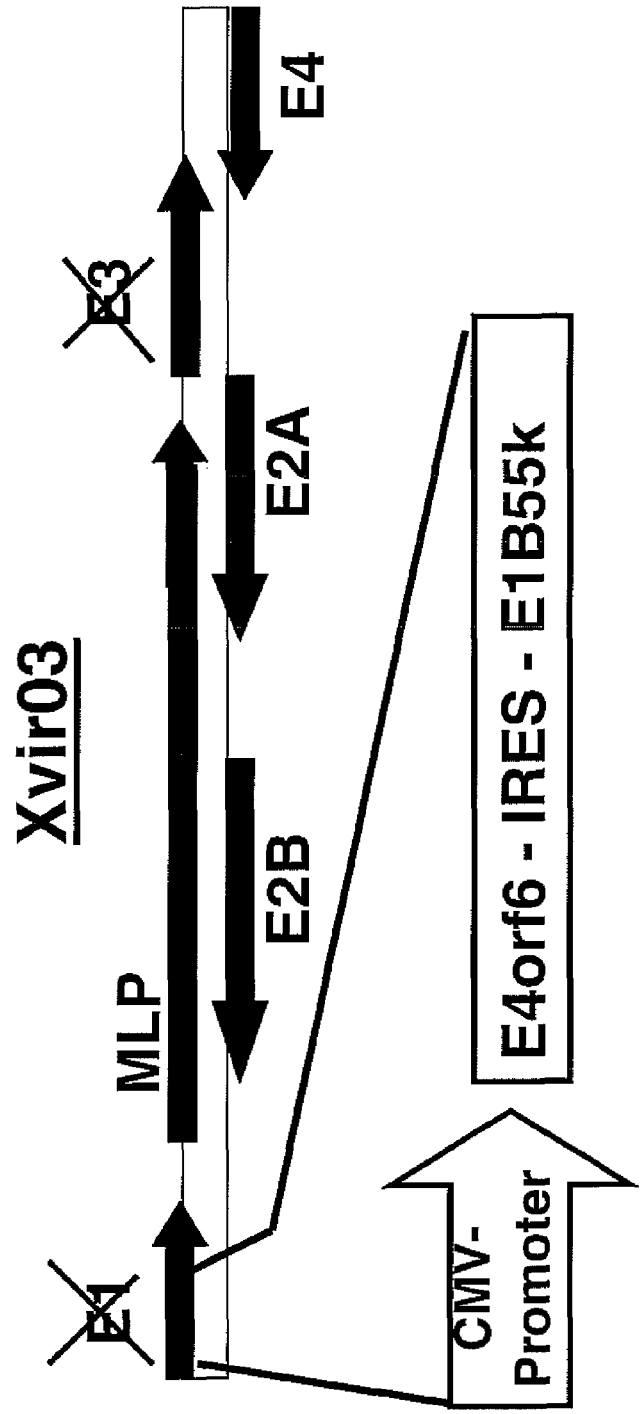

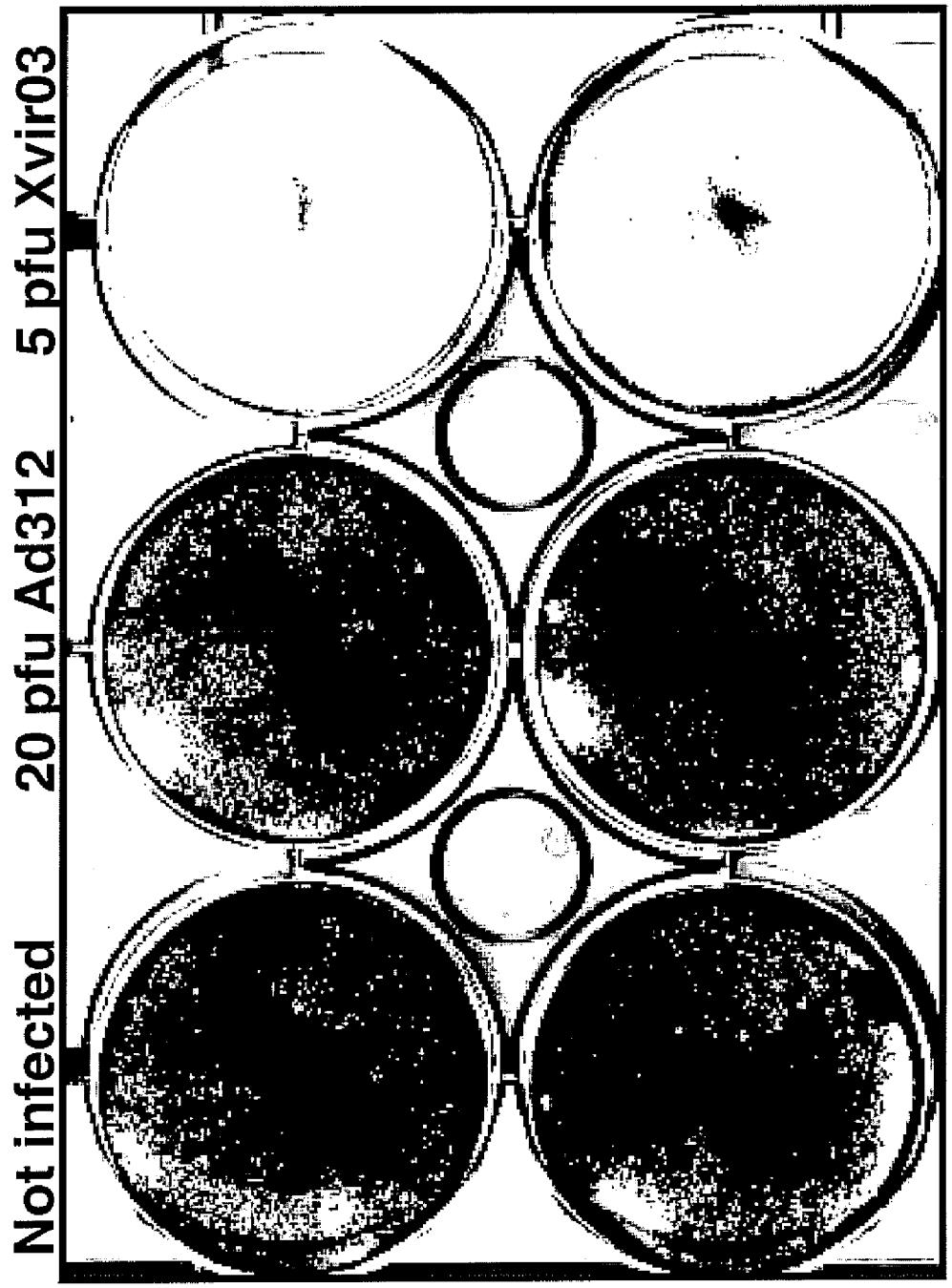

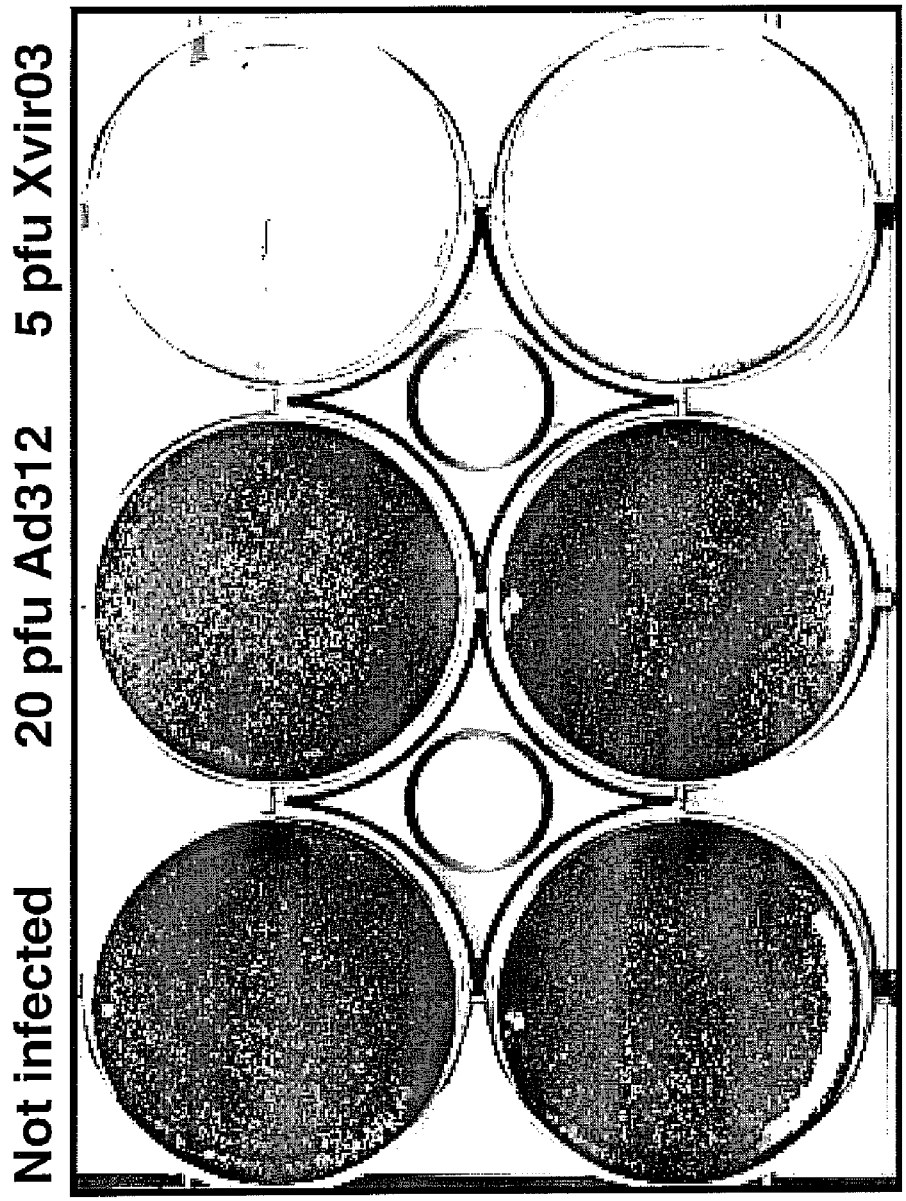

Fig. 20 Northern Blot Analysis of E2 gene expression in infected cells

Fig. 27 U373 cells infected with 10 pfu dl520/cell After incubation for 24 hours with increasing concentrations of Trichostatin Southern Blot Analysis Fig. 28 FACS analysis: CAR expression of U373 cells after incubation with Trichostatin for 24 hours Fig. 29 Oncolytic effect of dl520 in U373 cells in combination with Irinotecan and Trichostatin

Fig. 31

5'tgaggtactgaaatgtgtgggcgtggcttaagggtgggaaagaatataag
gtggggtcttatgtagttttgtatctgtttgcagcagccgcgccatgagc
accaactcgtttgatggaagcattgtgagctcatatttgacaacgcatgcccc
catgggcgggtgcgtcagaatgtgatgggctccagcattgatggtcgcccc
gtcctgcccgcaaactctactacctgacctacgagaccgtgtctgaacgccg
ttggagactgcagcctccgcccgcttcagccgctgcagccgcaccgcccgcg
ggattgtgactttgactttcctgagcccgcttgcaagcagtgcagcttcccgt
tcatccgcccgcgatgacaagtgacggctctttttggcacaattggattcttgac
ccgggaacttaatgtcgttttctcagcagtggatctgcgccagcaggtttctg
ccctgaaggcttcctcccctcccaatgcggtttaaaacataaataaaaaccag
actctgttttgattttggatcaagcaagtgtctgtctgtctttattttaggggttttgc ic viruses independent of the respective molecular prerequisites given for such treatment.

SEQUENCE LISTING

<160> NUMBER OF SEQ ID NOS: 31

<210> SEQ ID NO 1
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 1
tgaggctgat tggctgggca                                                    20

<210> SEQ ID NO 2
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 2
gtcggagatc agatccgcgt                                                    20

<210> SEQ ID NO 3
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 3
gatcctcgtc gtcttcgctt                                                    20

<210> SEQ ID NO 4
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 4
gtcggagatc agatccgcgt                                                    20

<210> SEQ ID NO 5
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 5
gatcctcgtc gtcttcgctt                                                    20

<210> SEQ ID NO 6
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 6
agctgatctt cgcttttg                                                   18

<210> SEQ ID NO 7
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 7
ggatagcaag actctgacaa ag                                              22

<210> SEQ ID NO 8
<211> LENGTH: 600
<212> TYPE: DNA
<213> ORGANISM: Adenovirus type 37
<220> FEATURE:
<221> NAME/KEY: misc_feature
<223> OTHER INFORMATION: E1B55k-3'UTR region

<400> SEQUENCE: 8
tgaggtactg aaatgtgtgg gcgtggctta agggtgggaa agaatatata aggtggggt      60 cttatgtagt tttgtatctg ttttgcagca gccgccgccg ccatgagcac caactcgttt    120
gatggaagca ttgtgagctc atatttgaca acgcgcatgc ccccatgggc cggggtgcgt    180
cagaatgtga tgggctccag cattgatggt cgccccgtcc tgcccgcaaa ctctactacc    240
ttgacctacg agaccgtgtc tggaacgccg ttggagactg cagcctccgc cgccgcttca    300
gccgctgcag ccaccgcccg cgggattgtg actgactttg cttctcctgag cccgcttgca   360 agcagtgcag cttcccgttc atccgcccgc gatgacaagt tgacggctct tttggcacaa    420
ttggattctt tgacccggga acttaatgtc gtttctcagc agctgttgga tctgcgccag    480
caggtttctg ccctgaaggc ttcctcccct cccaatgcgg tttaaaacat aaataaaaaa    540
ccagactctg tttggatttg gatcaagcaa gtgtcttgct gtctttattt aggggttttg    600

<210> SEQ ID NO 9
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: probe

<400> SEQUENCE: 9
atggagcgaa gaaaccc                                                    17

<210> SEQ ID NO 10
<211> LENGTH: 21

-continued

```
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 10
cacgtcctgg aaaaaataca c                                       21

<210> SEQ ID NO 11
<211> LENGTH: 27
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 11
cttcaggatc catgactacg tccggcg                                 27

<210> SEQ ID NO 12
<211> LENGTH: 37
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 12
gaagtgaatt cctacatggg ggtagagtca taatcgt                      37

<210> SEQ ID NO 13
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 13
tccggttatt ttccaccata ttgc                                    24

<210> SEQ ID NO 14
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 14
ttatcatcgt gtttttcaaa gg                                      22

<210> SEQ ID NO 15
<211> LENGTH: 24
<212> TYPE: DNA
<213> ORGANISM: Artificial
<220> FEATURE:
<223> OTHER INFORMATION: synthetic
<220> FEATURE:
```

```
<221> NAME/KEY: misc_feature
<223> OTHER INFORMATION: primer

<400> SEQUENCE: 15
gaggttaacc taagcactgc caag                                            24

<210> SEQ ID NO 16
<211> LENGTH: 43
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 16
catagagtat gcagatatcg ttagtgttac aggtttagtt ttg                       43

<210> SEQ ID NO 17
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 17
gtaacactaa cgatatctgc atactctatg tcattttcat gg                        42

<210> SEQ ID NO 18
<211> LENGTH: 26
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 18
cagcgacatg aacttaagtg agctgc                                          26

<210> SEQ ID NO 19
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: oligonucleotide introducing RGD

<400> SEQUENCE: 19
cacactaaac ggtacacagg aaacaggaga cacaacttgt gactgccgcg gagactgttt     60
ctgccc                                                                66

<210> SEQ ID NO 20
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: oligonucleotide introducing RGD
```

-continued

<400> SEQUENCE: 20
gggcagaaac agtctccgcg gcagtcacaa gttgtgtctc ctgtttcctg tgtaccgttt    60
agtgtg    66

<210> SEQ ID NO 21
<211> LENGTH: 78
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 21
tcgagctccg catttggcgg gcgggattgg tcttcgtaga acctaatctc gtgggcgtgg    60
tagtcctcag gtacaaat    78

<210> SEQ ID NO 22
<211> LENGTH: 79
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 22
agcttatttg tacctgagga ctaccacgcc cacgagatta ggttctacga agaccaatcc    60
cgcccgccaa atgcggagc    79

<210> SEQ ID NO 23
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 23
atggccgcca gtcttttg    18

<210> SEQ ID NO 24
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 24
ttatggcctg gggcgtttac    20

<210> SEQ ID NO 25
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

```
<400> SEQUENCE: 25
gaggttaacc taagcactgc caag                                              24

<210> SEQ ID NO 26
<211> LENGTH: 43
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 26
catagagtat gcagatatcg ttagtgttac aggtttagtt ttg                         43

<210> SEQ ID NO 27
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: primer

<400> SEQUENCE: 27
gtaacactaa cgatatctgc atactctatg tcattttcat gg                          42

<210> SEQ ID NO 28
<211> LENGTH: 26
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: oligonucleotide introducing RGD

<400> SEQUENCE: 28
cagcgacatg aacttaagtg agctgc                                            26

<210> SEQ ID NO 29
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: oligonucleotide introducing RGD

<400> SEQUENCE: 29
cacactaaac ggtacacagg aaacaggaga cacaacttgt gactgccgcg gagactgttt       60
ctgccc                                                                  66

<210> SEQ ID NO 30
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: oligonucleotide introducing RGD

<400> SEQUENCE: 30
```

-continued

```
gggcagaaac agtctccgcg gcagtcacaa gttgtgtctc ctgtttcctg tgtaccgttt        60
agtgtg                                                                   66

<210> SEQ ID NO 31
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<223> OTHER INFORMATION: peptide introducing RGD

<400> SEQUENCE: 31

Cys Asp Cys Arg Gly Asp Cys Phe Cys
1               5
```

ADENOVIRUSES, NUCLEIC ACIDS THAT CODE FOR THE SAME AND THE USE OF SAID VIRUSES

CROSS-REFERENCE TO RELATED APPLICATIONS

This application is a continuation of U.S. patent application Ser. No. 10/579,543, filed on May 15, 2006, now abandoned which is the national stage of International Application No. PCT/EP04/12931, filed on Nov. 15, 2004, which claims the benefit of German Patent Application Nos. DE 10 2004 018 117.9, filed on Apr. 14, 2004 and 10353152.1, filed on Nov. 14, 2003, the contents of all of which are incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 7, 2013, is named H_10020_US_C_1.txt and is 8.15 KB in size.

The invention is related to adenoviruses, nucleic acids coding therefor and use thereof, in particular for the manufacture of a medicament for the treatment of tumors.

A number of therapeutic concepts are currently used in the treatment of tumors. Apart from using surgery, chemotherapy and radiotherapy are predominant. All these techniques are, however, associated with considerable side effects. The use of replication selective oncolytic viruses provides for a new platform for the treatment of tumors. In connection therewith a selective intratumor replication of a viral agent is initiated which results in virus replication, lysis of the infected tumor cell and spreading of the virus to adjacent tumor cells. As the replication capabilities of the virus is limited to tumor cells, normal tissue is spared from replication and thus from lysis by the virus.

For the time being, several viral systems are subject to clinic trials aiming at tumor lysis. One example for such an adenovirus is dl1520 (Onyx-015) which has been successfully used in clinical phases I and II (Khuri, F. et al. Nature Medicine 6, 879-885, 2000). Onyx-015 is an adenovirus having a completely deleted E1B-55 kDa gene. The complete deletion of the E1B55 kDa protein of the adenovirus is based on the discovery that replication and thus lysis of cells is possible with an adenoviral vector which have a p53 deficiency (Kirn, D. et al., Proc. Am. Soc. Clin. Oncol. 17, 391a, 1998), whereby normal cells are not harmed. More particularly, the E1B-55 kDa gene product is involved in the inhibition of p53, the transport of viral mRNA and the switching off of the protein synthesis of the host cell. The inhibition of p53 occurs via formation of a complex consisting of p53 and the adenoviral encoded E1B-55 kDa protein and/or a complex consisting of E1B-55 kDa and E4orf6. p53, coded by TP53, is the starting point for a complex regulatory mechanism (Zambetti, G. P. et al., FASEB J. 7, 855-865, 1993), which results, among others, in an efficient inhibition of the cellular replication of viruses like adenovirus. The gene TP 53 is deleted or mutated in about 50% of all human tumors which results in the absence of—desired—apoptosis due to chemotherapy or radiation therapy resulting in an usually unsuccessful tumor treatment.

A further concept of tumorlytic adenoviruses is based on the discovery that if the E1A protein is present in a specific deleted form or comprises one or several mutations, which do not affect the binding of Rb/E2F and/or p107/E2F and/or p130/E2F, such adenovirus will not induce the entry of the infected cells into the S phase and will be capable of replicating in tumor cells which do not have a functional Rb protein. Additionally, the E1A protein can be deleted at the N-terminus and comprise one or several mutations in the region of amino acid positions 1 to 76 of the E1A proteins, respectively, in order to inhibit the binding of E1A to p300 and thus to provide for a more selective replication in tumor cells. These approaches are described in an exemplary manner in European patent EP 0 931 830. Examples for such viruses are AdΔ24, dl922-947, E1Ad/01/07 and CB016 (Howe, J. A. et al., Molecular Therapy 2, 485-495, 2000; Fueyo, J. et al., Oncogene 19, 2-12, 2000; Heise, C. et al., Nature Medicine 6, 11341139, 2001; Balague, C. et al., J. Virol. 75, 7602-7611, 2001). These adenoviral systems for oncolysis known in the prior art thus comprise distinct deletions in the E1A protein, whereby such deletions had been made under the assumption that a functional Rb protein and complexes consisting of inactive Rb protein and E2F, respectively, would block an efficient in vivo replication and in order to provide an adenoviral replication in vivo in Rb-negative/mutated cells only. These adenoviral systems according to the prior art are based on E1A in order to control in vivo replication by means of the early E2 promoter (engl. E2 early promoter) and free E2F (Dyson, N. Genes & Development, 12, 2245-2262, 1998).

A further form of tumorlytic adenoviral systems is based on the use of selective promoters for specifically expressing the viral oncogene E1A which provides for a selective replication in tumor cells (Rodriguez, R. et al., Cancer Res. 57, 2559-2563, 1997).

As described above, the selection of a cellular background which is appropriate for the respective concept underlying the mode of action is important for the various concepts of adenoviral tumorlytic viruses. In other words, the various adenoviral systems currently known may only be used if distinct molecular biological prerequisites are realized. This limits the use of such systems to distinct patient groups.

A particular problem in the treatment of tumor diseases arises once the patients develop a so-called multidrug resistance (engl. multidrug resistance (MDR)) which represents a particularly well studied form of resistance of tumors against cytostatics (Gottesman and Pastan, Annu. Rev. Biochem. 62, 385-427, 1993). It is based on the overexpression of the membrane-bound transport protein P-glycoprotein which belongs to the so-called ABC transporters (Stein, U. et al., JBC 276, 28562-69, 2001, J. Wijnholds, Novartis Found Symp., 243, 69-79, 2002). Bargou, R. C. et al. and Oda, Y. et al (Bargou, R. C. et al., Nature Medicine 3, 447-450, 1997; Clin. Cancer Res. 4, 2273-2277, 1998) were able to show that nuclear localisation of the human transcription factor YB-1 is directly involved in the activation of the expression of the P-glycoprotein. Further studies confirmed that YB-1 is transported into the nucleus by various stress conditions such as UV irradiation, administration of cytostatics (Koike, K. et al., FEBS Lett 17, 390-394, 1997) and hyperthermia (Stein, U. et al., JBC 276, 28562-69, 2001). Further studies confirmed that the nuclear localisation of YB-1 has an impact on one further ABC transporter. This ABC transporter is referred to as MRP (engl. multidrug resistance-related protein) and is involved in the formation of the so-called atypical non-P-glycoprotein dependent multidrug resistance (Stein, U. et al., JBC 276, 28562-69, 2001).

The problem underlying the present invention is to provide a technical teaching and in particular a means which allows to treat an organism, more particularly a human organism and a group of patients, respectively, specifically with tumorlytically active agents. It is a further problem underlying the present invention to provide a means which is suitable to cause tumorlysis in patients having tumor diseases which are resistant to cytostatics, particularly those which have a multidrug resistance. Finally, a problem underlying the present invention is to provide for an adenovirus which is suitable for cell lysis.

In a first aspect the problem underlying the invention is solved by an adenovirus expressing a first protein which is selected from the group comprising an E1B protein and an E4 protein, prior to a second protein which is selected from the group comprising an E1A-protein.

In an embodiment the first protein is an E1B protein, preferably an E1B55 kd protein.

In a further embodiment the first protein is an E4 protein, preferably an E4orf6 protein.

In a preferred embodiment the first protein is a combination of E1B protein and E4 protein, preferably a combination of E1B55 kD protein and E4orf6 protein.

In a preferred embodiment the E1A protein is an E1A12S protein. In an alternative embodiment the E1A protein is the E1A protein of the wildtype adenovirus, preferably of Ad 5, or the E1A of adenovirus delta 24.

In a second aspect the problem underlying the invention is solved by an adenovirus, whereby the adenovirus comprises at least one nucleic acid coding for a protein which is selected from the group comprising E1B proteins, E4 proteins and E1A proteins, whereby the at least one protein is under the control of a promoter which is different from the promoter controlling the expression of the protein in a wildtype adenovirus.

In an embodiment of the second aspect the adenovirus is an adenovirus according to the first aspect of the present invention.

In an embodiment of the second aspect the at least one protein is an E1B protein, preferably an E1B55 kD protein.

In an embodiment of the second aspect the at least one protein is an E4 protein, preferably an E4orf6 protein.

In an embodiment of the second aspect the at least one protein is an E1A protein, preferably an E1A12S protein. In a particularly preferred embodiment the E1A12S protein is a E1A12S protein of Ad5, preferably of wildtype Ad5, or a E1A12S protein of adenovirus delta 24.

In an embodiment of the second aspect the at least one protein is a combination of E1B protein and E4 protein, preferably a combination of E1B55 kD protein and E4orf6 protein.

In an embodiment of the second aspect the at least one protein is a combination of E1B protein and E1A protein, preferably a combination of E1B55 kD protein and E1A12S protein.

In a preferred embodiment of the second aspect the at least one protein is a combination of E4 protein and E1A protein, preferably a combination of E4orf6 protein and E1A12S protein.

In an embodiment of the second aspect the at least one protein is a combination of E1B protein, E4 protein and E1A protein, preferably a combination of E1B55 kD protein, E4orf6 protein and E1A12S protein.

In an embodiment of the second aspect the expression of the E1B protein is controlled by a promoter, whereby the promoter is selected from the group comprising tumor-specific promoters, organ-specific promoters, tissue-specific promoters, heterologous promoters and adenoviral promoters, whereby the adenoviral promoter is different from the E1B promoter.

In an embodiment of the second aspect the expression of the E4 protein is controlled by a promoter, whereby the promoter is selected from the group comprising tumor-specific promoters, organ-specific promoters, tissue-specific promoters, heterologous promoters and adenoviral promoters, whereby the adenoviral promoter is different from the E4 promoter.

In a preferred embodiment of the second aspect the adenoviral promoter is the E1A promoter.

In an embodiment of the second aspect the expression of the E1A protein is controlled by a promoter, whereby the promoter is selected from the group comprising tumor-specific promoters, organ-specific promoters, tissue-specific promoters, heterologous promoters and adenoviral promoters, whereby the adenoviral promoter is different from the E1A promoter.

In a preferred embodiment of the second aspect the promoter controlling the expression of the E1A protein is YB-1 controlled or can be regulated by YB-1.

In a preferred embodiment of the second aspect the promoter controlling the expression of the E1A protein is the adenoviral E2 late promoter.

In an embodiment of the first and second aspect the E4 protein, preferably the E4orf6 protein, and the E1B protein, preferably the E1B55 kd protein, are under the control of the same or a mutual promoter.

In a third aspect the problem underlying the invention is solved by an adenovirus, whereby the adenovirus provides YB-1 in the nucleus through at least one adenoviral protein or that the provision of YB-1 in the nucleus is mediated through at least one adenoviral protein, whereby preferably the adenoviral protein is different from E1A.

In an embodiment of the third aspect, the adenovirus is an adenovirus according to the first and/or second aspect of the present invention.

In a fourth aspect the problem underlying the invention is solved by an adenovirus, whereby the adenovirus provides YB-1 for adenoviral replication through at least one adenoviral protein or mediates the provision of YB-1 for adenoviral replication through at least one adenoviral protein, whereby preferably the adenoviral protein is different from E1A.

In an embodiment of the fourth aspect, the adenovirus us an adenovirus according to the first and/or second and/or third aspect of the present invention.

In an embodiment of the third and the fourth aspect, the adenoviral protein is a complex of E4orf6 and E1B55 kd.

In a fifth aspect the problem underlying the invention is solved by an adenovirus, whereby the nucleic acid of the adenovirus comprises at least one functionally inactive adenoviral region, whereby the region is selected from the group comprising the E1 region, the E3 region, the E4 region and combinations thereof.

In an embodiment of the fifth aspect the adenovirus is an adenovirus in accordance with the first and/or second and/or third and/or fourth aspect of the present invention.

In an embodiment of the fifth aspect the region is the E1 region.

In an embodiment of the fifth aspect the region is the E3 region.

In an embodiment of the fifth aspect the region is the E4 region.

In an embodiment of the fifth aspect the region comprises the E1 region, the E3 region and the E4 region.

In a sixth aspect the problem underlying the invention is solved by an adenovirus, whereby the adenovirus comprises at least one expression cassette, whereby the expression cassette comprises at least one promoter and a nucleic acid coding for an adenoviral protein, whereby the adenoviral protein is an E1B protein, preferably an E1B55kD protein.

In an embodiment of the sixth aspect the adenovirus is an adenovirus according to the first and/or second and/or third and/or fourth and/or fifth aspect of the present invention.

In an embodiment of the sixth aspect the promoter is different from the E1B promoter.

In an embodiment of the sixth aspect the promoter is selected from the group comprising tumor-specific promoters, organ-specific promoters, tissue-specific promoters, heterologous promoters and adenoviral promoters, whereby the promoter is different from the E1B promoter.

In a seventh aspect the problem underlying the invention is solved by an adenovirus, whereby the adenovirus comprises at least one expression cassette, whereby the expression cassette comprises at least one promoter and a nucleic acid coding for an adenoviral protein, whereby the adenoviral protein is an E4 protein, preferably an E4orf6 protein.

In an embodiment of the seventh aspect the adenovirus is an adenovirus according to the first and/or second and/or third and/or fourth and/or fifth and/or sixth aspect of the present invention.

In an embodiment of the seventh aspect the promoter is selected from the group comprising tumor-specific promoters, organ-specific promoters, tissue-specific promoters, heterologous promoters and adenoviral promoters, whereby the adenoviral promoters are different from the E4 promoter.

In an embodiment of the seventh aspect the promoter is the E1A promoter.

In an eighth aspect the problem underlying the invention is solved by an adenovirus, whereby the adenovirus comprises at least one expression cassette, whereby the expression cassette comprises at least one promoter and a nucleic acid coding for an adenoviral protein, whereby the adenoviral protein is an E1A protein, preferably an E1A12S protein.

In an embodiment of the eighth aspect, the adenovirus is an adenovirus according to the first and/or second and/or third and/or fourth and/or fifth and/or sixth and/or seventh aspect of the present invention.

In an embodiment of the eighth aspect the promoter is different from the E1A promoter.

In an embodiment of the eighth aspect the promoter is selected from the group comprising tumor-specific promoters, organ-specific promoters, tissue-specific promoters, heterologous promoters and adenoviral promoters.

In an embodiment of the first and/or second and/or third and/or fourth and/or fifth and/or sixth and/or seventh and/or eighth aspect the adenovirus comprises a nucleic acid, whereby the nucleic acid codes for YB-1.

In a preferred embodiment of the eighth aspect the nucleic acid coding for YB-1 is under the control of a promoter, whereby the promoter is preferably the E2 late promoter.

In an embodiment of the eighth aspect the nucleic acid coding for YB-1 is under the control of a promoter, whereby the promoter is YB-1 dependent and YB-1 controlled, respectively.

In an embodiment of the eighth aspect the nucleic acid coding for YB-1 is part of the expression cassette comprising a nucleic acid coding for an E1A protein, preferably a nucleic acid coding for an E1A12S protein.

In an embodiment of the eighth aspect the nucleic acid coding for the E1A protein is separated from the nucleic acid coding for YB-1 through an IRES sequence.

In an embodiment of the sixth and/or seventh and/or eighth aspect the nucleic acid coding for the E4 protein, preferably the E4orf6 protein, and the nucleic acid coding for the E1B protein, preferably the E1B55kD protein, are contained in an expression cassette, whereby preferably the two coding sequences are separated through an IRES sequence.

In a preferred embodiment of the eighth aspect the promoter of the expression cassette is selected from the group comprising tumor-specific promoters, organ-specific promoters, tissue-specific promoters, heterologous promoters and adenoviral promoters, whereby the adenoviral promoters are different from the E4 promoter and different from the E1B promoter, preferably different from the wildtype E4 promoter and different from the wildtype E1B promoter.

In an embodiment of the first and/or second and/or third and/or fourth and/or fifth and/or sixth and/or seventh and/or eighth aspect the adenovirus comprises an expression cassette comprising a promoter and a nucleic acid sequence, whereby the nucleic acid sequence is selected from the group comprising aptamers, ribozymes, aptazymes, antisense molecules and siRNA.

In an embodiment of the first and/or second and/or third and/or fourth and/or fifth and/or sixth and/or seventh and/or eighth aspect the adenovirus comprises an expression cassette comprising a promoter and a nucleic acid sequence, whereby the nucleic acid sequence is a coding nucleic acid, whereby the nucleic acid codes for a molecule which is selected from the group comprising peptides, polypeptides, proteins, anticalines, antibodies and antibody fragments.

In an embodiment of the first and/or second and/or third and/or fourth and/or fifth and/or sixth and/or seventh and/or eighth aspect the adenovirus comprises an expression cassette, whereby the expression cassette comprises a promoter and a nucleic acid sequence, whereby the nucleic acid sequence is selected from the group comprising apoptosis inducing genes, prodrug genes, protease inhibitors, tumor suppressor genes, cytokines and angiogenesis inhibitors.

In an embodiment of the first and/or second and/or third and/or fourth and/or fifth and/or sixth and/or seventh and/or eighth aspect the adenovirus is a recombinant adenovirus.

In an embodiment of the first and/or second and/or third and/or fourth and/or fifth and/or sixth and/or seventh and/or eighth aspect the adenovirus is an adenovirus mutant.

In an embodiment of the first and/or second and/or third and/or fourth and/or fifth and/or sixth and/or seventh and/or eighth aspect the adenovirus is replication deficient.

In an embodiment of the first and/or second and/or third and/or fourth and/or fifth and/or sixth and/or seventh and/or eighth aspect the adenovirus is capable of replicating in cells comprising deregulated YB-1 or having YB-1 in the nucleus.

In an embodiment of the first and/or second and/or third and/or fourth and/or fifth and/or sixth and/or seventh and/or eighth aspect the cells contain YB-1 in the nucleus independent of the cell cycle.

In an embodiment of the first and/or second and/or third and/or fourth and/or fifth and/or sixth and/or seventh and/or eighth aspect the adenovirus does not comprise any E1A13S protein and/or the adenovirus does not comprise any nucleic acid coding for a E1A13S protein.

In a ninth aspect the problem underlying the invention is solved by a nucleic acid coding for an adenovirus according to any of the aspects one to eight.

In a tenth aspect the problem underlying the invention is solved by replication system comprising a nucleic acid according to the ninth aspect and a nucleic acid of a helper virus, whereby the nucleic acid of the helper virus comprises one or more of the expression cassettes of the adenovirus according to any of the aspects one to eight.

In an embodiment of the tenth aspect the adenovirus or the nucleic acid coding therefor is lacking the expression cassette comprised by the helper virus.

In an eleventh aspect the problem underlying the invention is solved by a vector comprising a nucleic acid according to the ninth aspect and/or a replication system according to the tenth aspect.

In an embodiment of the eleventh aspect the vector is an expression vector.

In a twelfth aspect the problem underlying the invention is solved by an adenovirus ell comprising an adenovirus according to any of aspects one to eight and/or a nucleic acid according to the ninth aspect and/or a replication system according to the tenth aspect and/or a vector according to the eleventh aspect.

In an embodiment of the twelfth aspect the cell is a eucaryotic cell, preferably an animal cell, more preferably a mammalian cell.

In a preferred embodiment of the twelfth aspect the mammalian cell is a cell selected from the group comprising cells of mice, rats, guinea pigs, pigs, sheep, goats, cattle, horses, dogs, cats and human beings.

In a thirteenth aspect the problem underlying the invention is solved by an organism, preferably a mammal organism, comprising an adenovirus according to aspect one to eighth, a nucleic acid according to the ninth aspect, a replication system according to the tenth aspect, a vector according to the eighth aspect or a cell according to the twelfth aspect, whereby the organism is preferably selected from the group comprising mice, rats, guinea pigs, pigs, sheep, goats, cattle, horses, dogs and cats.

In a fourteenth aspect the problem underlying the invention is solved by the use of an adenovirus according to any of the aspects one to eighth, a nucleic acid according to the ninth aspect, a replication system according to the tenth aspect, a vector according to the eighth aspect, or a cell according to the twelfth aspect, for replication of an adenovirus, preferably for in vitro replication of an adenovirus.

In a fifteenth aspect the problem underlying the invention is solved by the use of an adenovirus according to any of aspects one to eighth, a nucleic acid according to the ninth aspect, a replication system according to the tenth aspect, a vector according to the eight aspect, or a cell according to the twelfth aspect for the manufacture of an adenovirus, preferably for in vitro manufacture of an adenovirus.

In a sixteenth aspect the problem underlying the invention is solved by the use of an adenovirus according to any of aspects one to eight, a nucleic acid according to the ninth aspect, a replication system according to the tenth aspect, a vector according to the eighth aspect, or a cell according to any the twelfth aspect for the expression of genes, preferably of genes which promote cell lysis, preferably cell lysis during adenoviral replication, and/or are promoting adenoviral mediated cell lysis.

In an embodiment of the sixteenth aspect the expressed genes are transgenes as disclosed herein.

In a seventeenth aspect the problem underlying the invention is solved by the use of an adenovirus according to any of aspects one to eight, a nucleic acid according to the ninth aspect, a replication system according to the tenth aspect, a vector according to the eighth aspect, or a cell according to the twelfth aspect for the manufacture of a medicament.

In an embodiment of the fourteenth to the seventeenth aspect the cell in which the adenovirus replicates, has YB-1 in its nucleus, preferably has YB-1 in its nucleus independent of the cell cycle.

In an embodiment of the fourteenth to the seventeenth aspect the cell in which the adenovirus replicates, comprises deregulated YB-1.

In an embodiment of the use of the seventeenth aspect the medicament is for the treatment of tumor diseases.

In a preferred embodiment of the use of the seventeenth aspect the tumor disease is selected from the group comprising malignant diseases, cancer, cancer diseases and tumors.

In an embodiment of the use of the seventeenth aspect the tumors are selected from the group comprising solids, non-solid, malignant and benign tumors.

In an embodiment of the use of the seventeenth aspect at least a part of the tumor forming cells have YB-1 in the nucleus, preferably have YB-1 in the nucleus independent of the cell cycle.

In an embodiment of the use of the seventeenth aspect at least a part of the cells forming the tumor comprises deregulated YB-1.

In an embodiment of the use of the seventeenth aspect at least a part of the cells forming the tumor are Rb positive or Rb negative.

In an embodiment of the use of the seventeenth aspect at least a part of the cells forming the tumor have a resistance, preferably a multiple resistance against pharmaceutically active agents.

In a preferred embodiment of the use of the seventeenth aspect the resistance is a multiple resistance.

In an embodiment of the use of the seventeenth aspect the resistance is against anti-tumor agents, preferably cytostatics, and/or that the resistance is caused by irradiation.

In an embodiment of the use of the seventeenth aspect the patient for which the medicament is intended, comprises a plurality of cells, whereby the cells are cells as described in the various embodiments of the use according to the seventeenth aspect of the present invention.

In an embodiment of the use of the seventeenth aspect the medicament comprises at least one further pharmaceutically active agent.

In an embodiment of the use of the seventeenth aspect the medicament is administered together with a further pharmaceutically active agent or is intended therefor.

In an embodiment of the use of the seventeenth aspect the further pharmaceutically active agent is selected from the group comprising cytokines, metalloproteinase inhibitors, angiogenesis inhibitors, cytostatics such as Irinotecan and CPT-11 against colorectal carcinoma and Daunorubicin against leukemia, cell cycle inhibitors such as CYC202 which inhibits CDK2/CyclinE kinase activity and can be used against colorectal tumors (McClue S J, Int. J. Cancer 2002, 102, 463-468) and BAY 43-9006 which inhibits Raf-1 and is, for example, effective against mamma carcinoma (Wilhelm S M et al., Cancer Res. 2004, 64, 7099-7109), proteosome inhibitors such as PS-341 which inhibits the 26S proteasome activity and is used against squamous-cell carcinoma (Fribley A et al., Mol Cell Biol 2004 November; 24(22): 9695-704), recombinant antibodies such as against the EGF receptor (Herceptin for breast carcinoma and prostate tumor; H. G. van der Poel, European Urology 2004, 1-17; Erbitux against head and neck tumors; Bauman M et al., Radiother. Oncol., 2004, 72, 257-266), and inhibitors of the signal transduction cascade such as STI 571 which represses, among others, c-kit and can be used against gastrointestinal tumors (H. G. van der Poel, European Urology 2004, 45, 1-17), ABT-627, an endothelin inhibitor, which may be used, among others, against prostate tumors (H. G. van der Poel, European Urology 2004, 45, 1-17), SU5416 which inhibits phosphorylation of the VEGF tyrosine kinase receptor and which may be used, among others, against glioblastoma and prostate cancer (Bischof M et al Int. J. Radiat. Oncol. Biol. Phys. 2004; 60 (4): 1220-32), ZD1839 which inhibits EGFR tyrosine activity and may be used, among others, against prostate tumors (H. G. van der Poel, European Urology 2004, 45, 1-17); rapamycin derivatives such as CCI-779 and RAD001 which inhibit mTOR and can be used against prostate tumors. It is within the present invention that the various adenoviruses described herein and the adenoviruses to be used in accordance with the present invention, respectively, can, in principle, be used with each and any of the aforementioned compounds for each and any of the indication described herein in connection therewith. In a particularly preferred embodiment the indication is the one which is described for any of the previously mentioned pharmaceutically active compounds.

In an embodiment of the use of the seventeenth aspect the medicament is administered prior, during or after irradiation.

In a preferred embodiment of the use of the seventeenth aspect the radiation is administered for the purpose of treating a tumor.

In an embodiment of the use of the seventeenth aspect the cell or the organism to be treated is subject to a measure, whereby the measure is selected from the group comprising irradiation, administration of cytostatics and hyperthermia.

In an embodiment of the use of the seventeenth aspect the measure is applied locally or systemically.

In an embodiment of the use of the seventeenth aspect the irradiation uses high-energy radiation, preferably uses any irradiation as used in the treatment of tumor diseases.

In an eighteenth aspect the problem underlying the invention is solved by the use of an adenovirus according to any of the aspects one to eight, a nucleic acid according to the ninth aspect, a replication system according to the tenth aspect, a vector according to the eleventh aspect, or a cell according to the twelfth aspect for the manufacture of a medicament for the treatment of tumor diseases, characterised in that the tumor disease is selected from the group comprising breast tumors, bone tumors, gastric tumors, intestinal tumors, gall-bladder tumors, pancreas tumors, liver tumors, kidney tumors, brain tumors, ovarian tumors, skin tumors, tumors of cutaneous appendages, head and neck cancer, uterine tumors, synovial tumors, laryngeal tumors, oesophageal tumors, lingual tumors, prostate tumors, preferably one of the preceding tumor diseases having the characteristics as described in any of the preceding claims.

In a nineteenth aspect the problem underlying the invention is solved by the use of an adenovirus according to any of the aspects one to eight, a nucleic acid according to the ninth aspect, a replication system according to the tenth aspect, a vector according to the eleventh aspect, or a cell according to the twelfth aspect for the manufacture of medicament for the treatment of tumor diseases, whereby the tumor-specific promoter is a promoter which is specific for the tumor for which the medicament is used.

In a twentieth aspect the problem underlying the invention is solved by a pharmaceutical composition comprising an adenovirus according to any of the aspects one to eight, a nucleic acid according to the ninth aspect, a replication system according to the tenth aspect, a vector according to the eleventh aspect, or a cell according to the twelfth aspect and optionally a pharmaceutically acceptable carrier.

In a twenty-first aspect the problem underlying the present invention is solved by the use of a virus, preferably an adenovirus, for the manufacture of a medicament, whereby the virus is replication deficient in normal cells which do not contain YB-1 in the nucleus, in cells which do not contain YB-1 in the nucleus independent of the cell cycle, and in cells which do not contain deregulated YB-1, respectively, and the virus codes for an oncogene or oncogene product, in particular an oncogene protein which at least transactivates one viral gene in YB-1 nucleus positive cells, preferably an adenoviral gene, whereby the gene is selected from the group comprising E1B55 kDa, E4orf6, E4orf3 and E3ADP. Preferably, the virus expresses the viral proteins E1B55kD, which is also referred to herein as E1B55 kDa, and E4orf6.

In a twenty-second aspect the problem underlying the invention is solved by the use of a virus, preferably an adenovirus, for replication in cells, which contain YB-1 in the nucleus, whereby the virus is replication deficient in cells which do not contain YB-1 in the nucleus, or cells which do not contain YB-1 in the nucleus independent of the cell cycle, or cells which do not contain any deregulated YB-1, and whereby the virus codes for an oncogene or an oncogene product, in particular an oncogene protein, which transactivates at least one viral gene, preferably an adenoviral gene, whereby the gene is selected from the group comprising E1B55kDa, E4orf6, E4orf3 and E3ADP.

In an embodiment of the uses in accordance with the twenty-first and twenty-second aspect of the invention the virus, in particular the adenovirus, replicates in cells which contain YB-1 in the nucleus or which do not contain YB-1 in the nucleus independent of the cell cycle, or which do not comprise any deregulated YB-1.

In a further embodiment of the uses in accordance with the twenty-first and twenty-second aspect of the invention the viral oncogene protein is E1A and/or the oncogene is the gene coding for E1A and/or the oncogene protein is E1A.

In a preferred embodiment the viral oncogene protein E1A is capable of binding a functional Rb tumor suppressor gene product.

In an alternative embodiment the viral oncogene protein E1A is incapable of binding a functional Rb tumor suppressor gene product.

In a further embodiment of the uses in accordance with the twenty-first and twenty-second aspect of the invention the viral oncogene protein E1A does not induce nuclear localisation of YB-1.

In a further embodiment of the uses in accordance with the twenty-first and twenty-second aspect of the invention the medicament is for patients the cells of which are either Rb positive or Rb negative.

In a preferred embodiment the cells are those cells involved in the formation of the condition which is to be affected by the medicament.

In a further embodiment of the uses in accordance with the twenty-first and twenty-second aspect of the invention the cells are Rb-negative and YB-1-positive in the nucleus, in particular are YB-1 positive in the nucleus independent of the cell cycle.

In a still further embodiment of the uses in accordance with the twenty-first and twenty-second aspect of the invention the medicament is for the treatment of tumors.

In a still further embodiment of the uses in accordance with the twenty-first and twenty-second aspect of the invention the cells, in particular the cells forming the tumor or parts thereof, are resistant, in particular multiple resistant against drugs, preferably anti-tumor agents and more preferably cytostatics.

In a preferred embodiment of the uses in accordance with the twenty-first and twenty-second aspect of the invention the cells are expressing, preferably are over-expressing the membrane-bound transport protein P-glycoprotein and/or MRP.

In a further embodiment of the uses in accordance with the twenty-first and twenty-second aspect of the invention the cells are either p53-positive or p53-negative.

In an embodiment of the uses in accordance with the twenty-first and twenty-second aspect of the invention the oncogene protein comprises, compared to the wildtype oncogene protein E1A, one or several mutations or deletions, whereby the deletions are preferably those selected from the group comprising deletions of the CR3 region and deletions of the N-terminus and deletions of the C-terminus. It is contemplated that the E1A oncogene protein is capable of binding to Rb.

In a further embodiment of the uses in accordance with the twenty-first and twenty-second aspect of the invention the oncogene protein comprises, compared to the wildtype oncogene protein, one or several mutations or deletions, whereby the deletion is preferably one in the CR1 region and/or CR2 region. It is contemplated that the oncogene protein E1A is incapable of binding to Rb.

In an embodiment of the uses in accordance with the twenty-first and twenty-second aspect of the invention the viral oncogene protein, in particular E1A, is under the control of a tissue-specific and/or tumor-specific promoter.

In a further embodiment of the uses in accordance with the twenty-first and twenty-second aspect of the invention the virus, in particular the adenovirus, is coding for YB-1.

In a still further embodiment of the uses in accordance with the twenty-first and twenty-second aspect of the invention YB-1 is under the control of a tissue-specific and/or tumor-specific promoter.

In a preferred embodiment of the uses in accordance with the twenty-first and twenty-second aspect of the invention the virus, in particular the adenovirus, codes for at least one protein which is selected from the group comprising E4orf6, E4orf3, E1B55k and adenoviral E3ADP protein.

In a alternative embodiment of the uses in accordance with the twenty-first and twenty-second aspect of the invention the cells contain YB-1 in the nucleus, in particular the cells forming the tumor or part thereof comprise YB-1 in the nucleus.

In a further embodiment of the uses in accordance with the twenty-first and twenty-second aspect of the invention the tumor contains YB-1 in the nucleus after induction of the transport of YB-1 into the nucleus.

In a preferred embodiment of the uses in accordance with the twenty-first and twenty-second aspect of the invention the transport of YB-1 into the nucleus is caused by at least one measure, whereby the measure is selected from the group comprising irradiation, administration of cytostatics and hyperthermia.

In a particularly preferred embodiment of the uses in accordance with the twenty-first and twenty-second aspect of the invention the measure is applied to a cell, an organ or an organism.

In a preferred embodiment of the uses in accordance with the twenty-first and twenty-second aspect of the invention the virus, in particular the adenovirus, is selected from the group comprising AdΔ24, dl922-947, E1Ad/01/07, dl1119/1131, CB 016, dl520 and viruses which are lacking an expressed viral E1A oncogene which is capable of binding a functional Rb tumor suppressor gene product.

In a twenty-third aspect the problem is solved by the use of a virus, preferably the adenovirus, for the manufacture of a medicament, whereby the virus, in particular the adenovirus, is adapted such that the replication is controlled through or by YB-1 mediated activation of the E2-late promoter, preferably predominantly controlled by the activation of the E2-late promoter. In an embodiment YB-1 is either a transgenic YB-1 or a cellular YB-1, in particular a cellular deregulated YB-1 or deregulated YB-1. A transgenic YB-1 is preferably a YB-1 which is expressed in a cell by a vector, in particular by a or the adenovirus. The E2-late promoter is preferably the adenoviral E2-late promoter as contained in wildtype adenovirus, or an E2-late promoter as used in connection with the expression of the transgens as described herein.

In a twenty-fourth aspect the problem is solved by the use of a virus, in particular the adenovirus, for replication in cells which contain YB-1 in the nucleus, whereby the virus, in particular the adenovirus, is adapted such that the replication is controlled by YB-1 through the activation of the E2-late promoter, preferably predominantly by the activation of the E2-late promoter. In an embodiment the YB-1 is either a transgenic YB-1 or a cellular YB-1, in particular a cellular deregulated or deregulated YB-1. A transgenic YB-1 is preferably a YB-1 which is expressed in a cell by a vector, in particular a or the adenovirus. The E2-late promoter is preferably the adenoviral E2-late promoter as present in wildtype adenovirus, or an E2-late promoter as used in connection with the expression of transgenes as described herein.

In a preferred embodiment of the twenty-third and/or twenty-fourth aspect of the present invention the adenovirus is adapted as disclosed herein, particularly adapted such that it may be used in accordance with the present invention.

In a twenty-fifth aspect the problem is solved by a viral oncogene protein, in particular an isolated viral oncogene protein, whereby the viral oncogene protein has the following characteristics:
a) transactivation of at least one viral gene in YB-1 nucleus positive cells which is selected from the group comprising E1B55k, E3ADP and E4orf6 and E4orf4; and
b) no induction of YB-1 in a cell nucleus, in particular in the cell nucleus of the cell in which the viral oncogene protein is present.

In an embodiment the viral oncogene protein is E1A.

In a further embodiment the viral oncogene protein comprises, compared to the wildtype oncogene protein, one or several mutations or deletions, whereby the deletions are preferably those selected from the group comprising deletion of the CR3 region, deletion of the N-terminus and deletion of the C-terminus.

In an embodiment the induction of YB-1 through the viral oncogene protein does not occur under the proviso that E4orf6 and/or E1B55kD is/are not present in the cell comprising said nucleus.

It is contemplated that the viral oncogene protein is capable of binding to Rb.

In an alternative embodiment the viral oncogene protein comprises one or several mutations or deletions, whereby the deletion is preferably one in the CR1 region and/or the CR2 region of the E1A oncogene protein. It is contemplated that the viral oncogene protein is incapable of binding to Rb.

In a twenty-sixth aspect the invention is related to the use of a viral replication system, in particular an adenoviral replication system comprising a nucleic acid coding for a virus, in particular an adenovirus, as used in accordance with the present invention, and comprising a nucleic acid of a helper virus, whereby the nucleic acid of the helper virus comprises a nucleic acid sequence coding for YB-1.

In an embodiment the viral nucleic acid, in particular the adenoviral nucleic acid, and/or the nucleic acid of the helper virus is present as replicable vector.

In a twenty-seventh aspect the invention is related to the use of a nucleic acid coding for a virus, in particular an adenovirus, as used in accordance with the present invention, for the manufacture of a medicament, in particular for the manufacture of a medicament for the treatment of tumors.

In a preferred embodiment the cells, in particular the cells forming the tumor or parts thereof, show a resistance, in particular a multiple resistance against drugs, in particular anti-tumor agents and more particularly cytostatics.

In a twenty-eighth aspect the present invention is related to the use of a nucleic acid coding for a virus, in particular an adenovirus, as used in accordance with the present invention, for the replication in cells which contain YB-1 in the nucleus, whereby the virus is replication deficient in cells which do not contain YB-1 in the nucleus or which do not comprise YB-1 in the nucleus independent of the cell cycle or which do not comprise any deregulated YB-1, and whereby the virus codes for an oncogene or an oncogene protein which at least trans-activates one viral gene, preferably an adenoviral gene in YB-1 nucleus positive cells, whereby the gene is selected from the group comprising E1B55 kDa, E4orf6, E4orf3 and E3ADP.

In a twenty-ninth aspect the problem is solved by the use of a nucleic acid coding for a virus, in particular an adenovirus, as used in accordance with the invention, for the manufacture of a medicament, whereby the virus is adapted such that the replication is controlled by YB-1 through the activation of the E2-late promoter, preferably predominantly through the activation of the E2-late promoter. In an embodiment the YB-1 is either a transgenic YB-1 or a cellular, in particular cellular deregulated, or deregulated YB-1. A transgenic YB-1 is preferably a YB-1 which is expressed in a cell by a vector, in particular by a or the adenovirus. The E2-late promoter is preferably the adenoviral E2-late promoter such as contained in wildtype adenovirus, or an E2-late promoter as used in connection with the expression of transgenes described herein.

In a thirtieth aspect the problem is solved by the use of a nucleic acid coding for a virus, in particular an adenovirus, as used in accordance with the present invention, for the replication in cells, whereby the virus is adapted so that the replication is controlled by YB-1 through the activation of E2-late promoter, preferably predominantly through the activation of the E2-late promoter. In an embodiment YB-1 is either a transgenic YB-1 or a cellular, in particular cellular deregulated YB-1. A transgenic YB-1 is preferably one which is expressed in a cell by a vector, preferably by a or the adenovirus. The E2-late promoter is preferably the adenoviral E2-late promoter as present in wildtype adenovirus, or an E2-late promoter as used in connection with the expression of transgenes as described herein.

In a thirty-first aspect the problem is solved by the use of a vector comprising one of the previously described nucleic acids, for the use in accordance with the twenty-first or twenty-second aspect of the present invention.

In a thirty-second aspect the invention is related to the use of an agent interacting with YB-1 for the characterisation of cells, of cells of a tumor tissue or of patients in order to determine whether they shall be contacted and/or treated with a virus, in particular an adenovirus, as used in accordance with the present invention.

In an embodiment the agent is selected from the group comprising antibodies, anticalines, aptamers, aptazymes and spiegelmers.

In a thirty-second aspect the problem is solved by the use of the viral oncogene protein in accordance with the present invention, or a nucleic acid coding therefor, for the manufacture of a virus, in particular of an adenovirus, as used in connection with the uses in accordance with the twenty-first and twenty-second aspect of the present invention.

In an embodiment the virus comprises a nucleic acid coding for a transgene.

In a further embodiment the virus comprises the translation product and/or the transcription product of a transgene.

In a preferred embodiment the nucleic acid of the adenoviral replication system and/or the nucleic acid of the helper virus comprises a transgene or a nucleic acid coding for a transgene.

In a still further embodiment the nucleic acid comprises a transgen or a nucleic acid coding for a transgene.

In an alternative embodiment the transgene is selected from the group comprising prodrugs, cytokines, apoptosis-inducing genes, tumor suppressor genes, genes for metalloproteinase inhibitors and genes for angiogenesis inhibitors and for tyrosine kinase inhibitors.

In an embodiment the transgene is selected from the group comprising nucleic acids for siRNA, for aptamers, for antisense molecules and for ribozymes, whereby the siRNA, the aptamers, the antisense molecules and/or the ribozymes are directed against the target molecule.

In a further embodiment the target molecule is selected from the group comprising resistance relevant factors, anti-apoptosis factors, oncogenes, angiogenesis factors, DNA synthesis enzymes, DNA repair enzymes, growth factors and their receptors, transcription factors, metalloproteinases, in particular matrix metalloproteinases, and plasminogen activator of the urokinase type. In an embodiment the resistance relevant factors are preferably selected from the group comprising P-glycoprotein, MRP and GST, and also comprise the nucleic acids coding therefor. In an embodiment the anti-apoptosis factors are selected from the group comprising BCL2, and also comprise the nucleic acids coding therefor. In an embodiment the oncogenes are selected from the group comprising Ras, in particular mutated Ras, Rb and MYC, and also comprise the nucleic acids coding therefor. In an embodiment the angiogenesis factors are selected from the group comprising VEGF and HMG proteins, and also comprise the nucleic acids coding therefor. In an embodiment the DNA synthesis enzymes are selected from the group comprising telomerase, and also comprise the nucleic acids coding therefor. In an embodiment the DNA repair enzymes are selected from the group comprising Ku-80, and also comprise the nucleic acids coding therefor. In an embodiment the growth factors are selected from the group comprising PDGF, EGF and M-CSF, and also comprise the nucleic acids coding therefor. In a further embodiment the receptors are preferably those for growth factors, whereby preferably the growth factors are selected from the group comprising PDGF, EGF and M-CSF, and also comprise the nucleic acids coding therefor. In an embodiment the transcription factors are selected from the group comprising YB-1, and also comprise the nucleic acids coding therefor. In an embodiment the metalloproteinases are in particular matrix metalloproteinases. In a preferred embodiment the matrix metalloproteinases are selected from the group comprising MMP-1 and MMP-2, and also comprise the nucleic acids coding therefor. In an embodiment the plasminogen activators of the urokinase type are selected from the group comprising uPa-R, and also comprise the nucleic acids coding therefor.

In a still further embodiment the medicament further comprises at least one pharmaceutically active compound.

In a preferred embodiment the pharmaceutically active compound is selected from the group comprising cytokines, metalloproteinase inhibitors, angiogenesis inhibitors, cytostatics such as Irinotecan and CPT-11 against colorectal carcinoma and Daunorubicin against leukemia, cell cycle inhibitors such as CYC202 which inhibits CDK2/CyclinE kinase activity and can be used against colorectal tumors (McClue S J, Int. J. Cancer 2002, 102, 463-468) and BAY 43-9006 which inhibits Raf-1 and is, for example, effective against mamma carcinoma (Wilhelm S M et al., Cancer Res. 2004, 64, 7099-

7109), proteosome inhibitors such as PS-341 which inhibits the 26S proteasome activity and is used against brain tumors, recombinant antibodies such as against the EGF receptor (Herceptin for breast carcinoma and prostate tumor; H. G. van der Poel, European Urology 2004, 1-17; Erbitux against head and neck tumors; Bauman M et al., Radiother. Oncol., 2004, 72, 257-266), and inhibitors of the signal transduction cascade such as STI 571 which represses, among others, c-kit and can be used against gastrointestinal tumors (H. G. van der Poel, European Urology 2004, 45, 1-17), ABT-627, an endothelin inhibitor, which may be used, among others, against prostate tumors (H. G. van der Poel, European Urology 2004, 45, 1-17), SU5416 which inhibits phosphorylation of the VEGF tyrosine kinase receptor and which may be used, among others, against neck and head tumors (Yin D. et al., Oncogene 2004), ZD1839 which inhibits EGFR tyrosine activity and may be used, among others, against prostate tumors (H. G. van der Poel, European Urology 2004, 45, 1-17); rapamycin derivatives such as CCI-779 and RAD001 which inhibit mTOR and can be used against prostate tumors. It is within the present invention that the various adenoviruses described herein and the adenoviruses to be used in accordance with the present invention, respectively, can, in principle, be used with each and any of the aforementioned compounds for each and any of the indication described herein in connection therewith. In a particularly preferred embodiment the indication is the one which is described for any of the previously mentioned pharmaceutically active compounds.

In an embodiment the medicament comprises a combination of at least two agents, whereby any agent is individually and independently selected from the group comprising cytostatics.

In a preferred embodiment at least two of the agent act upon different target molecules.

In an alternative embodiment at least two of the agents are active through a different mode of action.

In an embodiment at least one agents increases the capacity of a cell to be infected in which the virus replicates.

In an embodiment at least one agent has an impact on the availability of a component within the cell, which preferably increases the availability of the component, whereby the component mediates the uptake of the virus.

In an embodiment at least one agent mediates the transport in of YB-1 to the nucleus, preferably increases said transport.

In an embodiment at least one agent is a histone deacylase inhibitor.

In a preferred embodiment the histone deacylase inhibitor is selected from the group comprising trichostatine A, FR 901228, MS-27-275, NVP-LAQ824 and PXD101.

In an embodiment at least one agent is selected from the group comprising trichostatin A, FR 901228 (against pancreas tumors, Sato N et al., Int. J. Oncol. 2004, 24, 679-685; MS-27-275 (against prostate tumors; Camphausen K et al., Clinical Cancer Research 2004, 10, 6066-6071), NVP-LAQ824 (against leukemiae; Nimmanapalli R et al., Cancer Res. 2003, 63, 5126-5135; PXD101 (against ovary tumors, Plumb J A et al, Mol. Cancer. Ther. 2003, 2, 721-728), Scriptaid (against breast carcinoma, Keen J C et al., Breast Cancer Res. Treat. 2003, 81, 177-186), apicidin (against melanoma, Kim S H et al., Biochem. Biophys. Res. Commun. 2004, 315, 964-970) and CI-994 (against various tumors, Nemunaitis J J et al., Cancer J. 2003, 9, 58-66). The mode of action of histone deacetylase inhibitors is, among others, described in Lindemann R K et al., Cell Cycle 2004, 3, 77-86. It is within the present invention that the various adenoviruses described herein and the adenoviruses to be used in accordance with the present invention, respectively, may be used with the aforementioned compounds, in principle, for each and any of the indications described herein in connection therewith. In a particularly preferred embodiment the indication is one as has been described for each and any of the aforementioned pharmaceutically active compounds.

In an embodiment at least one agent is a topoisomerase inhibitor.

In a preferred embodiment the topoisomerase inhibitor is selected from the group comprising camptothecin, irinotecan, topotecan, DX-895If, SN-38, 9-aminocamptothecin, 9-nitro-camptothecin, etoposid and daunorubicin. These may be used against various tumors, for example, colorectal tumors, pancreas tumors, ovary carcinomas and prostate carcinomas. The fields of use are, among others, described by Recchia F et al., British J. Cancer 2004, 91, 1442-1446; Cantore M et al., Oncology 2004, 67, 93-97; Maurel J. et al., Gynecol. Oncol 2004, 95, 114-119; Amin A. et al., Urol. Oncol. 2004, 22, 398-403; Kindler H I, et al., Invest. New Drugs 2004, 22, 323-327, Ahmad T. et al., Expert Opin. Pharmacother. 2004, 5, 2333-2340; Azzariti A. et al., Biochem Pharmacol. 2004, 68, 135-144; Le Q T et al., Clinical Cancer Res. 2004, 10, 5418-5424. It is within the present invention that the various adenoviruses described herein and the adenoviruses to be used in accordance with the present invention, respectively, may in principle be used with the aforementioned compounds for each and any of the indications described herein in connection therewith. In a particularly preferred embodiment the indication is one as described for each of the aforementioned pharmaceutically active compounds.

In a preferred embodiment the agent comprises trichostatine A and irinotecan.

In an embodiment the virus, in particular the virus in accordance with one of the aspects of the present invention, is separated from the at least two agents.

In a preferred embodiment at least one unit doses of the virus is separated from at least one unit doses of one or the at least two agents.

In a thirty-fourth aspect the invention is related to a kit comprising a virus, in particular a virus according to any aspect of the present invention, and at least two agents, whereby any agent is individually and independently selected from the group comprising cytostatics.

The above disclosed adenovirus according to the present invention, particularly those as described in connection with aspects one to eight of the present invention, are also referred to herein as group I adenoviruses, and the adenoviruses having a transactivating oncogene protein such as, for example, E1A, and/or those referred to herein and particularly above, as to be used in accordance with the present invention, are also referred to herein as group II adenoviruses. Group I adenoviruses and group II adenoviruses are also collectively referred to herein as adenoviruses or adenoviruses according to the invention or viruses according to the invention.

The present invention is based on the surprising finding that the reversal of the expression sequence of adenoviral genes results in an efficient replication and optionally in the lysis of the cell infected by the adenovirus. With regard to the chronologically changed expression of the adenoviral genes particular emphasis is to be put on an E1B protein and an E4 protein which are also referred to herein, individually or collectively, as the first protein, which are expressed prior to a second protein. The second protein is selected from the group comprising E1A proteins. This expression sequence which is reversed compared to wildtype adenoviruses where first an E1A protein and only subsequently the E1B protein and an E4 protein are expressed, ensures that transcription factors are activated, for example transported, into the nucleus of the infected cell and influence the further replication activity or control the same there. The kinetics of the adenoviral transcripts in wildtype adenoviruses are, for example, described in Glenn G. M. and Ricciardi R. P. Virus Research 1988, 9, 73-91, who report that in the wildtype the E1A transcripts, i.e. the E1A12S transcript and the E1A13S transcript, are usually detectable prior to the transcripts and translation products, respectively, E4orf6 and E1B55k. In the present case the E1B protein is, and also herein in general if not indicated to the contrary, preferably the E1B-55 kD protein. In the present case, the E4 protein is, and also herein in general if not indicated to the contrary, preferably the E4orf6 protein. In the present case, the E1A protein is, and also herein in general if not indicated to the contrary, preferably an E1A12S protein or such an E1A protein as described herein in connection with the E1A-modified adenoviruses.

It is within the present invention that the E1A protein, in particular also the E1A12S protein may be substituted in principle. Such substituted E1A proteins and E1A12S proteins, respectively, are also referred to herein as E1A protein and E1A12S protein, respectively, or shall be deemed to be comprised by this term, if not indicated to the contrary. Instead of the E1A12S protein also an E1A protein may be used which has a tumor suppressor function, such as, for example, described by Dickopp A, Esche H, Swart G, Seeber S, Kirch H C, Opalka B. Cancer Gene Ther. 2000, July; 7(7):1043-50. Further derivatives of E1A proteins, in particular of the E1A12S protein, as used and/or as referred to as such herein, are generally also such proteins which are capable of releasing the factor E2F from the Rb/E2F complex. These are, among others, Simian virus 40 tumor antigen (SV40 large T antigen), papillomavirus E7 protein (HPV E7) as described by Chellappan S. et al., Proc. Natl. Acad. Sci. USA 1992, 89, 4549-4533.

It is also within the present invention that derivatives of E4orf6 and E1B55k may be used, whereby the term E4orf6 and E1B55k, as used herein, comprises such derivatives. The derivatives are, for example, described in Shen Y et al., J. of Virology 2001, 75, 4297-4307; Querido E. et al., J. of Virology 2001, 75, 699-709.

It is within the present invention that an E1B protein is expressed prior to the E1A protein, or that an E4 protein is expressed prior to an E1A protein, or that both an E1B protein and an E4 protein are expressed prior to the E1A protein, each as described above.

An adenovirus designed in such a way is capable of replicating at a particularly high level upon infection of a cell which expresses YB-1 in the nucleus, preferably expresses YB-1 in the nucleus independent from the cell cycle, or which comprises deregulated YB-1, preferably in the cytoplasm. Without wishing to be bound thereto in the following the present inventor assumes that a complex consisting of E1B protein and/or E4 protein and individual ones of these two proteins, respectively, is/are capable of transporting deregulated YB-1 into the cellular nucleus or is/are capable of initiating adenoviral replication there under the influence of the E1B protein and/or E4 protein being expressed prior to the E1A protein. Once in the cellular nucleus or being present there in activated form, YB-1 may, as described herein, in particular using the E2-late promoter, efficiently replicate. The chronologically early expression of an E1B protein and/or an E4 protein thus avoids the cascade as observed in wildtype going along with initial expression of E1A protein. In a preferred embodiment the E1A protein is an E1A protein which is in particular no longer transactivating or transactivating only to a very limited extent the E1B protein and/or the E4 protein. Preferably, this transactivation is neither sufficient to ensure an efficient replication, nor sufficient to ensure replication in cells which do not have YB-1 in the nucleus. It is preferred that the transactivation does not occur in cells which do not have YB-1 in the nucleus independent from the cell cycle or which do not have deregulated YB-1.

Furthermore, the present invention is based on the surprising finding that an adenovirus is capable of replicating in a particularly efficient manner if it comprises at least a nucleic acid which codes for a protein, whereby the protein is selected from the group comprising E1B proteins, E4 proteins and E1A proteins and that at least one protein thereof is under the control of a promoter which is different from the promoter which controls the expression of the respective protein in a wildtype adenovirus. Such replication is particularly efficient and usually results in tumor lysis in case the cells have YB-1 in the nucleus, in particular have YB-1 in the nucleus independent of the cell cycle, or in case the cells comprise deregulated YB-1, in particular comprise deregulated YB-1 in the cytoplasm. What has been said above about the E1B proteins, E4 proteins and E1A proteins applies also here. In wildtype adenoviruses the E1B protein is controlled by the E1B promoter, the E4 protein is controlled by the E4 promoter and the E1A protein is controlled by the E1A promoter. By selecting promoters which are different from those which control the expression of the aforementioned proteins in wildtype adenoviruses, the expression of the previously mentioned proteins and thus the regulatory interplay of the individual adenoviral nucleic acids and proteins is changed. By selecting the promoters a chronologically different expression pattern can be created which, without wishing to be bound thereto in the following, results in the observed replication in cells, whereby the mechanism may be the one as already previously described with regard to the chronologically different expression of the adenoviral proteins E1B, E4 and E1A. An example of a specific design for the control of said proteins through promoters different from those controlling the expression of the respective proteins in wildtype adenovirus, may be taken from the sub-claims and from the example part, whereby in particular the viruses referred to therein as XVirPSJL1 and XVirPSJL2 are representative thereof. Preferably, the E1B protein is the E1B55 kD protein, the E4 protein is the E4orf6 protein and the E1A protein is the E1A12S protein.

The promoters which preferably control the E1B protein as well as the E4 protein, are selected from the group comprising tumor-specific promoters, organ-specific promoters, tissue-specific promoters, heterologous promoters and adenoviral promoters under the proviso that when adenoviral promoters are used, they are different from the E1B promoter in case of the expression control of the E1B protein, and are different from the E4 promoter in case of expression control of the E4 protein. The use of the E1A promoter for the expression control of the E1B protein and/or the E4 protein is particularly preferred. The E1A promoter is, for example, described by Boulanger P. A. and Blair, G. E. Biochem. J. 1991, 275, 281-299. Additionally, also the use of each and any other heterologous promoter is possible, i.e. a promoter which is different from the one which controls the expression of the respective protein in a wildtype adenovirus. A representative example is the CMV promoter, whereby other promoters will be obvious for the ones skilled in the art.

The promoter which is used for the control of the E1A protein, may also be selected from the group comprising tumor-specific promoters, organ-specific promoters, tissue-specific promoters, heterologous promoters and adenoviral promoters under the proviso that the adenoviral promoter is different from the E1A promoter. It is within the present invention that one or several of the aforementioned proteins, i.e. the E1B protein, the E4 protein or the E1A protein are under the control of the same promoter, whereby it is nevertheless preferred that particularly the E1B protein and the E4 protein are under the control of the same promoter. It is particularly preferred that the expression of the E1A protein is controlled by a YB-1-controlled promoter or a promoter which can be regulated by YB-1. Such promoters are disclosed herein in connection with other aspects of the present invention. The use of the adenoviral E2-late promoter is particularly preferred for the control of the expression of the E1A promoter as it can, first, be regulated by YB-1 and, second, shows only little transcription in the absence of YB-1 which can factually be neglected so that a very good expression control of the nucleic acid which is under the control of the E2-late promoter, is ensured. This considerably increases biological safety, particularly when applied in the field of medicine.

Furthermore, the present inventor has found that adenoviruses will replicate particularly well in cells which have YB-1 in the nucleus, particularly have YB-1 in the nucleus independent of the cell cycle, and/or which have deregulated YB-1, preferably have deregulated YB-1 in the cytoplasm, if YB-1 is provided for replication either directly or indirectly in particular in the cellular nucleus or if the provision of YB-1 is directly or indirectly mediated through an adenoviral protein, whereby such adenoviral protein is different from E1A. This aspect of the present invention is different from the aspect which is also disclosed herein, namely that the use of transactivating E1A-modified adenoviruses, preferably group II adenoviruses, allows for replication of these viruses in YB-1 nucleus-positive tumor cells, particularly YB-1 nucleus-positive cells which are YB-1 positive independent of the cell cycle, and those cells which have deregulated YB-1, particularly comprise YB-1 in the cytoplasm, insofar that the transactivating characteristics of the E1A protein, particularly the E1A 13S protein are not used here, i.e. in connection with the group I adenoviruses, but rather in a preferred embodiment the E1A13S protein is functionally inactive and is thus no longer capable of transactivating also E4orf6 and E1B55k, which are involved in the transport and provision of YB-1, respectively, in the nucleus, either directly or indirectly. Consequently, an effective replication of the adenovirus is not possible in accordance with this aspect of the present invention. Insofar, the provision of YB-1 in the nucleus and the provision of YB-1 for adenoviral replication, respectively, is now no longer under the control of the direct or indirect involvement of the E1A protein but occurs through the expression of the E1B protein, particularly E1B55 kD protein, and/or the E4 protein, particularly the E4orf6 protein, which is not controlled by E1A.

This embodiment of the adenovirus may also be provided by one of the above-described measures, for example by bringing forward the chronological expression of the E1B protein and/or the E4 protein compared to the expression of the E1A protein, or by putting one or several of the E1B proteins, E4 proteins and E1A proteins under the control of a promoter which is different from the promoter which controls the expression of the respective protein in wildtype adenovirus.

Finally, the present inventor starts from the surprising finding that an effective adenoviral replication may also occur, particularly in cells which have YB-1 in the nucleus, more particularly YB-1 in the nucleus independent of the cell cycle, or in cells which have deregulated YB-1, preferably in the cytoplasm, in case at least one of the E1B proteins, E4 proteins and E1A proteins, particularly the preferred forms thereof, are expressed in an expression cassette under the control of a promoter. In one embodiment of the present invention basically three expression cassettes each comprising a single one of said proteins are provided. In an alternative embodiment an expression cassette may also comprise two or more of the proteins E1B, E4 and E1A and their derivatives and possible substituents, respectively, particularly in case of E1A12S. What has previously been said in relation to the aspect that the adenoviruses comprise nucleic acids related to proteins E1B, E4 and E1A, is also applicable to the design of the various proteins and the respectively used promoters. When using such expression cassettes it is preferred that proteins and nucleic acids coding therefor in the genome of the wildtype adenovirus which correspond to the respective proteins of the expression cassettes, are either completely or partially deleted to ensure that the virus is stable and to avoid recombinations, at least to a bigger extent.

In principle, the expression cassettes can be cloned into each region and each site, respectively, of the adenovirus, whereby preferably one or several of the cassettes are inserted either individually or in combination with each other into the E1 region, the E3 region and/or the E4 region of the virus. It is possible that the nucleic acids of the E1, E3 and E4 region are completely deleted, partially deleted or not deleted at all, whereby it is preferred with regard to the adenoviruses according to the invention that the nucleic acid coding for the E1A13S gene is inactivated or deleted so as not to provide any transactivating E1A protein by the virus. The extent of such deletion in one or several of the regions E1, E3 and E4 is determined by the expression cassette used and, optionally, further introduced foreign genes or transgenes or the further expression cassettes comprising them, i.e. genes which are different from the adenoviral genes, at least different in the sense that they are not provided in the regulatory context of the adenoviral nucleic acid as prevailing in wildtype adenovirus or are not provided in the sequence of the adenoviral nucleic acids of wildtype adenoviruses at such site. It is within the present invention that the nucleic acids which are contained in one or several of the expression cassettes which code for an E1B protein, an E4 protein and/or an E1A protein, are partially or completely deleted in the adenoviral genome. In an embodiment, such as in the adenovirus according to the present invention XvirPSJL1 or 2, the adenoviral nucleic acid coding for E4orf6 is partially deleted and/or completely deleted, however, the complete nucleic acid coding therefor is contained in the expression cassette. Preferably, this will also be realised for the E1B55k (also referred to as E1 55 Kd) protein and/or the E1A12S protein. The extent of the deletion is to be selected in preferred embodiments such that a maximum package size of about 103% of the maximum package size of the wildtype adenovirus is reached, although this limit is only a preferred limit. The possible deletions to be made in the adenoviral genome are only subject to limitations in preferred embodiments such as to make sure that still infectious and packed particles can be manufactured. The precise extent of the deletions may be determined by the ones skilled in the art on the basis of the disclosure provided herein together with standard tests.

As a starting point for the construction of the adenoviruses described herein, any wildtype adenovirus may be used, but also other adenoviruses may be used provided that they are constructed in accordance with the technical teaching of the present invention. It is particularly preferred to have recourse to adenoviruses of subgroup C and within this group in turn to adenovirus 2 and adenovirus 5.

The terms E1B protein and E1B proteins, E4 protein and E4 proteins as well as E1A protein and E1 proteins are used herein in a synonymous manner, if not indicated to the contrary.

As used herein, the term "deregulated" YB-1 refers to a YB-1 molecule or YB-1 protein as described herein which is present in a form which is quantitatively and/or qualitatively different from YB-1 as normally present in cells, preferably in non-tumor cells. A deregulated YB-1 can be characterised and identified as such by particular viruses being able to replicate in the presence of deregulated YB-1 in a cellular background comprising such deregulated YB-1. The particular viruses in connection therewith are those the E1A protein of which is mutated and exhibits a transactivating function. Examples for these particular viruses are AD delta 24, dl 922-947, E1 Ad/01/07 and CB 016 and/or those described by Howe, J. A et al., Molecular Therapy 2, 485-495, 2000; Fueyo J. et al., Oncogene 19, 2-12, 2000; Heise C. et al., Nature Medicine 6, 1134-1139, 2001; Balague, C et al., J. Virol. 75, 7602-7611, 2001; Bautista, D. S. et al., Virology 1991, 182, 578-596; Jelsma T. N. et al., Virology 1988, 163, 494-502; Wong, H. K. and Ziff E. B., J. of Virology 1994, 68, 4910-4920]. Such a cell and a cell, respectively, having such a background can be used for the replication of group I adenoviruses and/or group II adenoviruses. Additionally, tumors comprising such cells may be lysed by the adenoviruses according to the invention.

Furthermore, the present invention is based on the surprising finding that the DNA replication of E1A-modified adenoviruses in YB-1 nucleus-positive tumor cells is based on the activation of the E2-late promoter. E1A-modified adenoviruses are to be understood as those which (a) have, in YB-1 nucleus-negative cells, a reduced or no replication at all compared to wildtype, (b) have a transactivation activity on at least one viral gene, whereby the gene is particularly selected from the group comprising E1B-55 kDa, E4orf6, E4orf3 and E3ADP, and/or (c) do not translocate cellular YB-1 into the nucleus by the adenovirus. Optionally, the adenoviruses used in accordance with the present invention have the further characteristic that the binding of the E1A protein encoded by the adenovirus is interfering with the binding of E2F to RB and is capable of dissolving the respective complex consisting of E2F and Rb. Adenoviruses which have one or several of the aforementioned features a) to c), preferably all of the features a) to c), are replication deficient in cells which do not have YB-1 in the nucleus.

In an embodiment a strongly reduced replication herein in particular means a replication which is decreased compared to the wildtype by a factor of 2, preferably a factor of 5, more preferably a factor of 10 and most preferably a factor of 100. In a preferred embodiment the comparison of the replication is made using identical or similar cell lines, identical or similar virus titres for the infection (multiplicity of infection, MOI or plaque forming unit, pfu) and/or identical or similar general experimental conditions. Replication particularly means the formation of particles. In further embodiments the measure for replication may be the extent of viral nucleic acid synthesis. Methods for determining the extent of viral nucleic acid synthesis and methods for the determining particle formation are both known to the ones skilled in the art.

The findings, methods, uses or nucleic acids, proteins, replication systems and the like, are not necessarily limited to adenoviruses. Basically, such systems also exist in other viruses which are also encompassed herewith.

Using the viruses according to the present invention or the use of the viruses described herein in accordance with the present invention, may result in a replication comparable to wildtype when using an infection rate of 1 to 10 pfu/cell compared to 10 to 100 pfu/cell in accordance with the prior art.

Cellular YB-1 shall be any YB-1 which is encoded and is, preferably, also expressed by the cell, whereby this YB-1 is present in the cell particularly prior to the infection of the respective cell by an adenovirus, preferably an adenovirus and/or a helper virus as described herein. However, it is also within the present invention that cellular YB-1 is also a YB-1 which is introduced into the cell or produced by the cell only when exogenous measures such as infection with a virus, preferably an adenovirus, are applied.

Without wishing to be bound thereto, the present inventor assumes that the E2-early promoter, i.e. the early E2 promoter, is not switched on by means of the human cellular E2F transcription factor in connection with the replication of the viruses used in accordance with the present invention and in connection with the use in accordance with the present invention of the adenoviruses of the present invention. Under such circumstances the start of the replication is independent of the Rb status of the cells, i.e. the tumor cells which are infected by using the viruses disclosed herein and which are preferably lysed subsequently, may contain either functional as well as inactive Rb proteins. In addition, adenoviral replication using the adenoviruses disclosed herein or using the conditions disclosed herein, does not require any functional p53 protein, however is neither negatively affected by its presence. Insofar the technical teaching turns away from the principle underlying the use of oncolytic or tumorlytic adenoviruses of the type of AdΔ24, dl922-947, E1Ad/01/07, CB016 or those adenoviruses described, for example, in European patent EP 0 931 830, which had been made subject to one and/or several deletion(s) in the E1A protein under the assumption that intact functional Rb proteins would hinder an efficient in vivo replication and thus provide for adenoviral replication in vivo only in Rb-negative and Rb-mutated cells. These adenoviral systems of the prior art are based on E1A in order to control in vivo replication of adenoviruses by means of the early E2 promoter (E2-early promoter) and "free E2F". Nevertheless, these known viruses of the prior art may be used in accordance with the present invention for the replication in cells which contain YB-1 in the nucleus independent of the cell cycle, or in cells which comprise deregulated YB-1.

The viruses in particular adenoviruses described in said European patent EP 0 931 830 may be used in accordance with the present invention. More specifically, the viruses described in said patent are viruses which are replication deficient and which lack an expressed viral oncoprotein which is capable of binding a functional Rb tumor suppressor gene product. The adenovirus can particularly be any adenovirus which lacks expressed viral E1A oncoprotein which is capable of binding a functional tumor suppressor gene product, more particularly Rb. The viral E1A oncoprotein can exhibit an inactivating mutation, for example in the CR1 domain at the amino acid positions 30 to 85 in adenovirus Ad5, which is also referred to herein as Ad5, Ad 5, the nucleotide positions 697-790 and/or the CR2 domain at amino acid positions 120 to 130 in Ad 5, the nucleotide position 920 to 967 which are involved in the binding of p105 Rb protein, p130 and p107 protein. However, it is within the present invention that the adenovirus is of type 2 dl 312 or type 5 NT dl 1010.

In connection with the use of adenoviruses in accordance with the present invention for the manufacture of a medicament, in particular for the manufacture of a medicament for the treatment of tumor diseases and of the other diseases disclosed herein, and in connection with the use of adenoviruses in accordance with the present invention as well as the use of the adenoviruses according to the present invention for replication in cells which have YB-1 in the nucleus, preferably have YB-1 in the nucleus independent of the cell cycle or which comprise deregulated YB-1, preferably in the cytoplasm, replication finally occurs in those cells which have YB-1 in the nucleus, preferably independent of the cell cycle, which are, in other words, YB-1 nucleus-positive, or in cells which comprise deregulated YB-1. It is particularly to be acknowledged that the adenoviruses as such do not replicate or only replicate at a significantly reduced level in cells which do not have YB-1 in the nucleus but only contain YB-1 in the cytoplasm, or in cells which do not contain any deregulated YB-1. Insofar it is necessary for a successful replication of these viruses that YB-1 is present in the nucleus, preferably independent of the cell cycle, or that deregulated YB-1 is present. As will also be explained in the following, this can be achieved, for example, by applying to the cells conditions which result in the expression or presence of YB-1, preferably independent of the cell cycle, or deregulated YB-1 in the nucleus or in the expression of deregulated YB-1. A respective measure can, for example, be the coding and expression, respectively, of YB-1 by the adenoviruses which are either used in accordance with the present invention or which are subject to the present invention, which in addition to the adenoviral genes also carry genetic information which codes for YB-1 and which particularly codes for its expression. Other measures which result in the transport, induction or expression of YB-1 in the nucleus of the cell, are application of stress such as the administration to the cell and to an organism containing such a cell of cytostatics, irradiation, hyperthermia and the like. In a preferred embodiment irradiation is any radiation which is, for example, used in the treatment of tumor diseases.

The adenoviruses used in accordance with the present invention, particularly for tumor lysis, as well as the adenoviruses according to the invention are characterised in preferred embodiments by the fact that they do not replicate in cells which do not have YB-1 in the nucleus independent of the cell cycle and which are thus YB-1 nucleus-negative, or which do not comprise any deregulated YB-1.

A further feature of a part of the adenoviruses to be used in accordance with the present invention which are different from the adenoviruses of the present invention, is that they code for a viral oncogene which is also referred to herein as oncogene protein, whereby the oncogene protein is preferably E1A and whereby the oncogene protein is capable of activating at least one viral gene which has an impact on the replication of the virus and/or cell lysis of the cell infected by said virus. Preferably, the impact on the replication is such that the virus replicates better in the presence of the oncogene protein compared to the scenario where the oncogene protein of the respective virus is absent. This process is also referred to herein as transactivating and particularly as E1A transactivating in case the transactivation is mediated by E1A. The term "transactivate" or "transactivation" preferably describes the process that the respective viral oncoprotein has an impact on the expression and/or on the transcription of one or several other genes which are different from the gene coding for the viral oncogene protein itself, i.e. controls its/their expression and/or translation and particularly activates it/them. Such viral genes are preferably E1B55 kDa, E4orf6, E4orf3 and E3ADP as well as any combination of the aforementioned genes and gene products, respectively.

A further, although only optional feature of the adenoviruses to be used in accordance with the present invention as well as of the adenoviruses of the present invention is their binding characteristics and the binding characteristics of particular ones of the proteins coded by them, respectively, to tumor suppressor Rb. Basically, it is within the present invention that the adenoviruses used in accordance with the present invention may or may not bind to Rb. The use of any of the two alternative embodiments of the adenoviruses is independent of the Rb status of the cells treated or the cells to be treated.

In order to confer to E1A the ability not to bind to Rb, the following deletions can be made to the E1A oncoprotein: deletion in the CR1 region (amino acid positions 30-85 in Ad5) and deletion of the CR2 region (amino acid positions 120-139 in Ad5). In doing so, the CR3 region is preserved and can exercise its transactivating function on the other early viral genes.

In order to confer to E1A the ability to bind to Rb, the following deletions to E1A oncoprotein, however, are basically possible: deletion of the CR3 region (amino acid positions 140-185); deletion of the N-terminus (amino acid positions 1-29); deletion of the amino acid positions 85-119; and deletion of the C-terminus (amino acid positions 186-289). The regions listed above do not interfere with the binding of E2F to Rb. The transactivating function remains intact, however, is reduced compared to wildtype Ad5.

It is also within the present invention, particularly with regard to the adenoviruses of the present invention, that the E1A protein, particularly the E1A12S protein is designed such that, in an embodiment, it is capable of binding to Rb and, in a different embodiment, is not capable of binding to Rb, whereby such E1A12S protein is an E1A protein and particularly an E1A12S protein in the meaning of the present invention which is nevertheless referred to in the prior art sometimes as modified E1A12S. The respective design of the E1A12S protein is within the skills of those of the art, particularly with regard to the aforementioned deletions of the E1A protein which is also referred to herein simply as E1A.

Such adenoviruses which are basically already known in the prior art and which do not show any transactivation, are generally regarded as replication deficient. However, it is the merit of the present inventor that he has recognised that they are nevertheless capable of replicating in a suitable background, in particular a cellular background. Such suitable cellular background is caused or provided by the presence of YB-1 in the nucleus, preferably a cell cycle independent presence of YB-1 in the nucleus, or by deregulated YB-1. The term cells or cellular systems as used herein in connection with each and any other aspect of the present invention, comprises fragments or fractions of cell extracts as well as cells which are present in vitro, in vivo or in situ. Insofar, the term cellular systems or cells also comprises cells which are present in cell culture, tissue culture, organ culture or in any tissue or organ in vivo and in situ, respectively, isolated, in groups or as part of tissues, organs or organisms, but which may also be present as such in a preferably living organism. The organism is preferably any vertebrate organism and more preferably a mammal. More preferably the organism is a human organism. Other preferred organisms are those disclosed in connection with the various aspects of the present invention.

Additionally, it is within the present invention that based on the technical teaching provided herein, new viruses are generated which show the replication behaviour of the adenoviruses described herein and of those of the prior art in such cells which are YB-1 nucleus-positive, preferably YB-1 nucleus-positive independent of the cell cycle, or which comprise deregulated YB-1. In other words, particularly starting preferably from the adenoviruses already known, further viruses can be constructed which exhibit the features defined herein which are relevant for the use in accordance with the invention.

In connection with the present invention the modified E1A oncoprotein of the various adenoviruses to be used in accordance with the present invention is, in contrast to the viruses of the present invention, capable of transactivating the early viral genes such as E1B55K, E4orf3, E4orf6, E3ADP in YB-1 nucleus-positive cells or cells which comprise deregulated YB-1. There are preferably no other changes made to the viral genome and the respective adenovirus may insofar correspond otherwise to a wildtype adenovirus or a derivative thereof.

The viruses disclosed herein which code or comprise a transactivating oncogene protein in the meaning of the present invention, comprise, for example, the adenoviruses AdΔ24, dl922-947, E1Ad/01/07, CB106 and/or the adenoviruses described in European patent EP 0 931 830 which are each capable of transactivating the early genes such as E1B, E2, E3 and/or E4 and which are comparable to the adenoviruses of wildtype, particularly wildtype Ad5. In these cases, a distinct region of the E1A protein is responsible for the transactivation. Within the various adenoviral serotypes there are three highly conserved regions within the E1A protein. The region CR1 from amino acid positions 41-80, CR2 from amino acid positions 120-139 and CR3 from amino acid positions 140-188. The transactivating function is mainly based on the presence of the CR3 region within the E1A protein. The amino acid sequence of CR3 is present in an unchanged manner in the above mentioned adenoviruses. This results in a transactivation of the early genes E1B, E2, E3 and E4 independent of whether YB-1 is present in the nucleus or in the cytoplasm.

In contrast thereto, the CR3 region has been deleted in the recombinant adenovirus dl520. Thus, dl520 expresses a so-called E1A12S protein which does not comprise the amino acid sequence of the CR3 region. Consequently, dl520 may exercise only a very weak transactivating function, particularly on the E2 region, and thus does not replicate in YB-1 nucleus-negative cells. In YB-1 nucleus-positive cells YB-1 is responsible for the transactivation of the E2 region and thus allows for an efficient replication of dl520. The use of systems like dl520 or systems originating therefrom for the purposes disclosed herein, is based thereon. A further important difference between the two previously described groups of adenoviruses such as, for example, delta 24 (also referred to herein as AdΔ24) and, for example, dl520, resides in the fact that' the early genes E1B, E3 and E4 are more comprehensively transactivated in cells being YB-1 nucleus-positive cells independent of the cell cycle or in cells containing deregulated YB-1, compared to YB-1 nucleus-negative cells or cells which do not comprise deregulated YB-1. In contrast thereto, there are no or only minor differences in delta 24. The transactivation of dl520, more specifically of the E1A12S protein is, however, significantly reduced compared to wildtype adenovirus. This transactivation, however, is sufficient so as to provide for an efficient replication in YB-1 nucleus-positive cells as also shown in example 10. The design of the E1A protein as described herein and in particular as described in this connection, and of the nucleic acid coding therefor, such that the E1A protein has, compared to the wildtype oncogene protein E1A, one or several deletions and/or mutations, including and particularly preferably those designs of the E1A protein as described in connection with dl520 or AdΔ24, dl922 to 947, E1Ad/01/07, CB106 and/or the adenoviruses described in European patent EP 0 931 830, are embodiments of viruses, in particular of adenoviruses, the replication of which is controlled, preferably predominantly controlled by the activation of the E2-late promoter. Preferably, the deletion is such that it is selected from the group comprising deletions of the CR3 region and deletions of the N-terminus and deletions of the C-terminus. Further embodiments of the E1A protein which allow this kind of replication of adenoviruses, can be generated by the ones skilled in the art based on the disclosure provided herein. The embodiment of the E1A protein as described previously is an embodiment which may also be used in connection with the adenoviruses of the present invention which are also referred to herein as adenoviruses of the present invention or group I adenoviruses.

The adenoviruses of the present invention, particularly the group I adenoviruses, which are also referred to herein as derivatives and which may be used in accordance with the present invention, typically comprise an E1 deletion, an E1/E3 deletion and/or an E4 deletion, i.e. the corresponding adenoviruses are not capable of generating functionally active E1 and/or E3 and/or E4 expression products and corresponding products, respectively. Or in other words these adenoviruses are only capable of generating functionally inactive E1, E3 and/or E4 expression products, whereby a functionally inactive E1, E3 and/or E4 expression product is an expression product which is either not present as an expression product at all, either at the transcription level and/or at the translation level, or is present in a form which at least does not have one of the functions attributed to it in a wildtype adenovirus. This/these function(s) inherent to the expression product in wildtype adenovirus is/are known to the ones skilled in the art and, for example, described in Russell, W. C., Journal of Virology, 81, 2573-2604, 2000. Russell (supra) also describes design principles of adenoviruses and adenoviral vectors which are incorporated herein by reference. It is also within the present invention that the modified E1A oncoprotein, i.e. the no longer transactivating E1A protein and other proteins such as E1A12S, E1B-55K, E4orf6 and/or E3ADP (adenoviral death protein (ADP)) (Tollefson, A. et al., J. Virology, 70, 2296-2306, 1996) are expressed in such vector either alone or in any combination. The individual mentioned genes as well as the transgenes disclosed herein, may be, independently from each other, cloned into the E1 and/or E3 and/or E4 region and expressed using a suitable promoter or under the control of a suitable promoter. Basically, each of the E1, E3 and E4 region is suitable as cloning site within the adenoviral nucleic acid, whereby the regions not used for the cloning can, either individually or as a whole, be present, partially and/or completely deleted. In case that these regions are present, in particular are present in their entirety, it is within the present invention that they are either intact and preferably provide for a translation product and/or a transcription product, and/or are not intact and preferably do not provide for a translation product and/transcription product. In some embodiments suitable promoters are those as disclosed herein in connection with the control and expression, respectively, of E1A, preferably of the modified E1A.

Finally, in an embodiment, the group II adenoviruses used in accordance with the present invention are E1B deficient, particularly E1B 19 kDa deficient. The term deficient as generally used herein refers to a condition, wherein the E1B does not exhibit all of the characteristics of the wildtype E1B and lacks at least one of these characteristics.

The adenoviral BCL2 homolog E1B19k avoids the E1A induced apoptosis by interaction with the pro-apoptotic proteins Bak and Bax. Because of this a maximum replication and/or particle formation is possible in infected cells (Ramya Sundararajan and Eileen White, Journal of Virology 2001, 75, 7506-7516). The lack of E1B19k results in a better release of the viruses as, if present, it will minimize the function of the adenoviral death protein. By such a deletion the virus induced cytopathic effect is increased (Ta-Chiang Liu et al., Molecular Therapy, 2004) and thus results in a more pronounced lysis of infected tumor cells. Additionally, the lack of E1B19k causes that TNF-alpha does not exert an influence on the replication of such recombinant adenoviruses in tumor cells, whereas in normal cells the treatment results in a reduced replication and release of infectious viruses. Insofar, selectivity and specificity are increased (Ta-Chiang Liu et al., Molecular Therapy 2004, 9, 786-803).

At least some embodiments of the group II adenoviruses as used in accordance with the invention disclosed herein, are as such known in the art. The adenoviruses used in accordance with the invention are preferably recombinant adenoviruses, particularly also if, compared to the wildtype, a change has been made in the sense of the technical teaching provided herein. It is within the skills of those of the art to delete and mutate, respectively, the adenoviral nucleic acid sequences which are irrelevant for the invention. Such deletions may be related to, e.g. a part of the E3 and E4 coding nucleic acids as also described herein. A deletion of E4 is particularly preferred provided that such deletion does not extend to the protein E4orf6, in other words the adenovirus to be used in accordance with the invention codes for E4orf6. In preferred embodiments, these adenoviral nucleic acids may still be packed into viral capsids and thus form infectious particles. This is also true for the use of the nucleic acids in accordance with the invention. Generally it is also to be acknowledged that the adenoviral systems may be deficient with regard to single or several expression products. In connection therewith it is to be taken into consideration that this, in connection with both the group I adenoviruses and the group II adenoviruses, may be caused by the mutation or deletion of the nucleic acid coding the expression product, whereby such mutation and deletion, respectively, is either a complete one or performed to the extent that no expression product is formed anymore or by the regulatory elements and elements controlling the expression such as promoters and transcription factors being missing or being active in a way different from wildtype, either at the level of the nucleic acid (lack of a promoter; cis acting elements) or at the level of the translation and transcription system (transacting elements), respectively. Particularly the latter aspect may depend on the respective cellular background.

Apart from using adenoviruses which are as such already known, in accordance with the present invention also novel adenoviruses such as group II adenoviruses may be used for the purposes already disclosed for the other adenoviruses described herein. The new adenoviruses of the invention result from the technical teaching provided herein. Particularly preferred representatives are, for example, the viruses Xvir03 and Xvir03/01 which are depicted in FIGS. 16 and 17, the design principle of which is further illustrated in examples 11 and 12.

In case of vector Xvir03 a CMV promoter was cloned into the E1 region which controls the nucleic acids for E1B 55k and E4orf6 which are separated by an IRES sequence. In connection therewith the E3 and E4 region may be deleted and/or may be present in an intact form Due to the cloning of these two genes into the virus and due to the gene products generated therefrom, respectively, a high replication efficiency results, whereby the selective replication in cells, preferably tumor cells, is maintained insofar as a replication occurs particularly in YB-1 nucleus-positive cells and more particularly in those cells which comprise deregulated YB-1 in the sense of the present disclosure. Cells in which deregulated YB-1 is present are, in an embodiment, cells which show an increased expression of YB-1, preferably compartment independent expression of YB-1, compared to normal or non-tumor cells. E1B 55k and E4orf6 can also be cloned into the E4 region, whereby the E3 region can be intact or/and partially or completely deleted.

A further development of virus Xvir03 is virus Xvir03/01 into which in a preferred embodiment therapeutic genes or transgenes have been cloned under the control of a specific promoter, in particular a tumor-specific or tissue-specific promoter. In connection therewith the E3 and the E4 region can be deleted and/or be intact. Furthermore, in connection with such virus also the E4 region is functionally inactive, is preferably deleted. The transgenes described herein may also be cloned into the E4 region, whereby this can be done either alternatively or in addition to the cloning of the transgenes into the E3 region.

The transgenes described herein and particularly described in the following, may also be expressed in connection with or by the adenoviruses of the present invention, i.e. group I adenoviruses and their nucleic acids, respectively, or the replication systems of the invention and are thus comprised in connection with an expression cassette comprising a promoter and a nucleic acid sequence, whereby such nucleic acid sequence codes for one or several of said transgenes. The E1, E3 and/or E4 regions are particularly suitable cloning sites in the adenoviral genome, however, the cloning sites are not limited thereto. Transgenes as used herein, may be viral genes, preferably adenoviral genes, which are preferably not present in the genome and, respectively, which are not present at the site of the genome of the wildtype where they are present in the particular virus now, or therapeutic genes.

Therapeutic genes may be prodrug genes, genes for cytokines, apoptosis inducing genes, tumor suppressor genes, genes for metalloproteinase inhibitors and/or angiogenesis inhibitors, and tyrosine kinase inhibitors. Additionally, siRNA, aptamers, antisense molecules and ribozymes may be expressed which are preferably directed against cancer-relevant target molecules. Preferably the individual or the several target molecules are selected from the group comprising the resistance-relevant factors, anti-apoptosis factors, oncogenes, angiogenesis factors, DNA synthesis enzymes, DNA repair enzymes, growth factors and their receptors, transcription factors, metalloproteinases, particularly matrix metalloproteinases, and plasminogen activator of the urokinase type. Preferred embodiments thereof are those which have been disclosed already herein in connection with other aspects of the invention.

Possible prodrug genes as may be used in preferred embodiments, are, for example, cytosine deaminase, thymidine kinase, carboxypeptidase, uracil phosphoribosyl transferase; or purine nucleoside phosphorylase (PNP); [Kirn et al, Trends in Molecular Medicine, volume 8, no. 4 (suppl), 2002; Wybranietz W. A. et al., Gene Therapy, 8, 1654-1664, 2001; Niculescu-Duvaz et al., Curr. Opin. Mol. Therapy, 1, 480.486, 1999; Koyama et al., Cancer Gene Therapy, 7, 1015-1022, 2000; Rogers et al., Human Gene Therapy, 7, 2235-2245, 1996; Lockett et al., Clinical Cancer Res., 3, 2075-2080, 1997; Vijayakrishna et al., J. Pharmacol. And Exp. Therapeutics, 304, 1280-1284, 2003].

Possible cytokines as may be used in preferred embodiments, are, for example, GM-CSF, TNF-alpha, Il-12, Il-2, Il-6, CSF or interferon-gamma; [Gene Therapy, Advances in Pharmacology, volume 40, editor: J. Thomas August, Academic Press; Zhang and Degroot, Endocrinology, 144, 1393-

1398, 2003; Descamps et al., J. Mol. Med., 74, 183-189, 1996; Majumdar et al., Cancer Gene Therapy, 7, 1086-1099, 2000].

Possible apoptosis-inducing genes as may be used in preferred embodiments, are, for example, Decorin [Tralhao et al., FASEB J, 17, 464-466, 2003]; retinoblastoma 94 [Zhang et al., Cancer Res., 63, 760-765, 2003]; Bax and Bad [Zhang et al., Hum. Gene Ther., 20, 2051-2064, 2002]; apoptin [Noteborn and Pietersen, Adv. Exp. Med. Biol., 465, 153-161, 2000]; ADP [Toth et al., Cancer Gene Therapy, 10, 193-200, 2003]; bcl-xs [Sumantran et al., Cancer Res, 55, 2507-2512, 1995]; E4orf4 [Braithwaite and Russell, Apoptosis, 6, 359-370, 2001]; FasL, Apo-1 and Trail [Boehringer Manheim, Guide to Apoptotic Pathways, Arai et al., PNAC, 94, 13862-13867, 1997]; Bims [Yamaguchi et al., Gene Therapy, 10, 375-385, 2003; GNR163: Oncology News, 17 Jun., 2000].

Possible tumor suppressor genes as may be used in preferred embodiments, are, for example, E1A, p. 53, p16, p21, p27 or MDA-7 [Opalka et al., Cell Tissues Organs, 172, 126-132, 2002, Ji et al., Cancer Res., 59, 3333-3339, 1999, Su et al., Oncogene, 22, 1164-1180, 2003].

Possible angiogenesis inhibitors as may be used in preferred embodiments, are, for example, endostatin or angiostatin [Hajitou et al., FASEB J., 16, 1802-1804, 2002], and antibodies against VEGF [Ferrara, N., Semin Oncol 2002 December; 29 (6 suppl 16): 10-4].

Possible metalloproteinase inhibitors as may be used in preferred embodiments, are, for example, Timp-3 [Ahonen et al., Mol Therapy, 5, 705-715, 2002]; PAI-1 [Soff et al., J. Clin. Invest., 96, 2593-2600, 1995]; Timp-1 [Brandt K. Curr. Gene Therapy, 2, 255-271, 2002].

Further transgenes in the sense of the present invention which may be expressed by both group I adenoviruses and group II adenoviruses are also tyrosine kinase inhibitors. Exemplary tyrosine kinases are EGFR (epidermal growth factor receptor) [Onkologie, Entstehung and Progression maligner Tumoren; author: Christoph Wagner, Georg Thieme Verlag, Stuttgart, 1999]. A preferred tyrosine kinase inhibitor is herceptin [Zhang H et al., Cancer Biol Ther. 2003, July-August; 2 (4 suppl 1): S122-6].

SiRNA (short interfering RNA) which may be used in connection with the present invention, consists of two, preferably separate RNA strands which hybridise to each other due to base complementarity which means that they are present essentially base paired and preferably have a length of up to 50 nucleotides, preferably between 18 and 30 nucleotides, more preferably less than 25 nucleotides and most preferably 21, 22 or 23 nucleotides, whereby these figures refer to the single strand of the siRNA, particularly to the length of the stretch of the single strand which hybridises to or is base paired with a, more precisely the second single strand. siRNA specifically induces or mediates the degradation of mRNA. The specificity required theretofore is mediated by the sequence of the siRNA and thus its binding site. The target sequence to be degraded is essentially complementary to the first or to the second of the siRNA forming strands. Although the precise mode of action is not yet clear, it is assumed that siRNA is a biological strategy for cells in order to inhibit distinct alleles during development and to protect themselves against viruses. siRNA mediated RNA interference is used as a method for the specific suppression or complete elimination of the expression of a protein by introducing a gene specific double-stranded RNA. For higher organisms a siRNA comprising 19 to 23 nucleotides is insofar particularly suitable as it does not result in the activation of a non-specific defense reaction such as an interleukin response. The direct transfection of double-stranded RNA of 21 nucleotides having symmetrical 2-nt 3' overhangs was suitable to mediate RNA interference in mammalian cells and is highly efficient compared to other technologies such as ribozymes and antisense molecules (Elbashir, S. Harborth J. Lendeckel W. Yalvcin, A. Weber K, Tuschl T: Duplexes of 21-nucleotide RNAs mediate RNA interference in cultured mammalian cells. Nature 2001, 411: 494-498). As little as a few siRNA molecules are sufficient so as to suppress expression of the target gene. In order to avoid the limitations of exogenously added siRNA which particularly reside in the transient nature of the interference phenomenon and specific delivery (delivery) of the siRNA molecules, vectors are used in the prior art which allow for an endogenous siRNA expression. For such purpose, for example, oligonucleotides having a length of 64 nucleotides are introduced into the vector which comprise the 19 nucleotide long target sequence both in the sense and in the antisense orientation, separated by, for example, a 9 nucleotide spacer sequence. The resulting transcript folds into a hairpin structure with a stem structure (stem) of, for example, 19 base pairs. The loop is rapidly degraded in the cell so that a functional siRNA molecule is generated (Brummelkamp et al., Science, 296, 550-553, 2002).

The nucleic acid coding for YB-1 which may be part of the adenoviruses in an embodiment of the adenoviruses to be used in accordance with the invention, particularly group II adenoviruses, but also of the adenoviruses according to the invention, i.e. group I adenoviruses, may comprise a nucleic acid sequence which mediates the transport of YB-1 into the nucleus. The nucleic acids, adenoviruses and adenoviral systems according to the invention as well as the adenoviruses known in the prior art such as, for example, Onyx-15, AdΔ24, dl922-947, E1Ad/01/07, CB016, dl 520 and the adenoviruses described in patent EP 0 931 830 may be used, as adenoviruses and adenoviral systems, respectively, and the corresponding nucleic acids, in combination with these nucleic acids in accordance with the invention. Suitable nucleic acid sequences mediating nuclear transport are known to the ones skilled in the art and, for example, described in Whittaker, G. R. et al., Virology, 246, 1-23, 1998; Friedberg, E. C., TIBS 17, 347, 1992; Jans, D. A. et al., Bioassays 2000 June; 22(6): 532-44; Yoneda, Y., J. Biochem. (Tokyo) 1997 May; 121(5): 811-7; Boulikas, T., Crit. Rev. Eukaryot. Gene Expr. 1993; 3(3): 193-227; Lyons R H, Mol. Cell Biol., 7 2451-2456, 1987). The nucleic acid sequences mediating nuclear transport may realise different principles. One such principle is that YB-1 forms a fusion protein with a signal peptide or is provided with such signal peptide and is transferred into the cellular nucleus because of the signal peptide, whereupon the replication of the adenoviruses in accordance with the invention occurs.

A further principle which may be used in the design of the adenoviruses to be used in accordance with the invention, particularly group II adenoviruses, but also with the adenoviruses in accordance with the present invention, i.e. the group I adenoviruses, is providing YB-1 with a transport sequence which results in the transfer or translocation of YB-1 into the cellular nucleus, preferably starting from a synthesis in the cytoplasm, and prompts viral replication there. An example for a particularly effective nucleic acid sequence mediating transport into the nucleus, is the TAT sequence of HIV which is, for example, described together with other suitable nucleic acid sequences of that kind in Efthymiadis, A., Briggs, L J, Jans, D A., JBC 273, 1623-1628, 1998. It is within the present invention that the adenoviruses to be used in accordance with the invention, particularly group II adenoviruses, but also the adenoviruses according to the present invention, i.e. group I adenoviruses, comprise the nucleic acid sequences which code for the peptides which mediate nuclear transport.

It is within the present invention that YB-1 is present in its full length, particularly in a form which corresponds to wild-type YB-1. Furthermore, it is within the invention that YB-1 is used or present as a derivative, for example in a shortened or truncated form. A YB-1 derivative as may be used or may be present in connection with the present invention, is a YB-1 which is preferably capable of binding to the E2 late promoter and thus activates gene expression of the adenoviral E2 region. Such derivatives particularly comprise the YB-1 derivatives disclosed herein. Further derivatives can be generated by deletion of single or several amino acids at the N-terminus, the C-terminus or within the amino acid sequence. It is within the present invention that also YB-1 fragments are used as YB-1 proteins in the sense of the present invention. In the paper of Jürchott K et al. [JBC 2003, 278, 27988-27996] various YB-1 fragments are disclosed which are characterised by deletions at the C- and the N-terminus. The distribution of the various YB-1 fragments has shown that both the cold shock domain (CSD) as well as the C-terminus is relevant for the cell cycle regulated transport of YB-1 into the cellular nucleus. It is thus within the present invention that a shortened YB-1 (herein also referred to as YB-1 protein) in connection with the inventive expression of E1B55k and E4orf6 migrates better into the nucleus and thus induces a stronger CPE without necessarily binding better to the E2-late promoter compared to native YB-1, whereby it cannot be excluded that also a shortened YB-1 migrates better into the nucleus and is causing both effects, i.e. induces CPE and binds to the E2-late promoter. Finally, such shortened YB-1 fragments may also migrate better into the nucleus and bind more efficiently to the E2-late promoter without inducing a better CPE. It is also within the present invention that shortened YB-1 proteins and fragments, respectively, comprise further sequences as disclosed herein in connection with the full length YB-1, in particular cell localisation signal sequences (NLS) and the like.

With regard to the aforementioned various further genes and gene products encoded and expressed, respectively, by the adenovirus, it is in principle possible that these are coded and expressed, respectively, in any combination.

It is within the present invention that the terms adenovirus and adenoviral systems are to be understood as having essentially the same meaning. The term adenovirus shall particularly be understood such as to be related to the complete virus particle comprising the capsid and the nucleic acid. The term adenoviral system particularly focuses on the fact that the nucleic acid is changed compared to the wildtype. Preferably such changes comprise changes in the set-up of the genome of the adenovirus as may result from deleting and/or adding and/or mutating promoters, regulatory sequences and/or coding sequences such as reading frames. The term adenoviral system is additionally more preferably used such that it is a vector which may, for example, be used in gene therapy.

The above comments, including any use and any design of the adenoviruses and adenoviral systems, respectively, are also applicable to the nucleic acids coding therefor and vice versa.

In connection with the present invention it is possible that the adenoviruses used in accordance with the invention, particularly group II adenoviruses, but also group I adenoviruses and the nucleic acids coding therefor, is any respective adenoviral nucleic acid which as such or in combination with further nucleic acid sequences results in a replication event. It is possible, as explained herein, that the sequences and/or gene products necessary for replication are provided by helper viruses. To the extent it is referred to coding nucleic acid sequences and said nucleic sequences are nucleic sequences which are known, it is within the present invention that not only the identical sequence is used but also sequences derived therefrom. Herein, derived sequences shall mean in particular any sequences which still result in a gene product, either a nucleic acid or a polypeptide which has a function which corresponds to a or the function of the non-derived sequence. This can be tested by routine tests known to the one skilled in the art. An example for such derived nucleic acid sequences are those nucleic acid sequences which code for the same gene product, in particular for the same amino acid sequence, which, however, have a different base sequence due to the degeneracy of the genetic code.

With regard to the adenoviruses according to the invention of group II and/or the corresponding adenoviral replication system according to the invention and their use in accordance with the invention, respectively, in an embodiment the adenoviral nucleic acid is deficient for the expression of the oncogene protein, in particular is E1A protein deficient, i.e. does either not code for the 12S E1A protein (herein also referred to as E1A12S protein) or for the 13S E1A protein (herein also referred to as E1A13S protein) or does not code for both the 12S E1A protein and the 13S E1A protein, or is modified, as defined herein, if not indicated to the contrary, and that the adenoviral replication system further comprises a nucleic acid of a helper virus, whereby the nucleic acid of the helper virus comprises a nucleic acid sequence which codes for the oncogene protein, particularly the E1A protein, which has the following characteristics and confers the following characteristics to the adenovirus, respectively: It is preferably non-replicating in YB-1 nucleus-negative cells but is replicating in cells which are independent of the cell cycle in YB-1 nucleus-positive or in cells exhibiting deregulated YB-1, is transactivating at least one viral gene, in particular E1B55 kDa, E4orf6, E4orf3 and/or E3ADP, in YB-1 nucleus-positive cells, and/or does not transfer cellular YB-1 into the nucleus. It is within the present invention that the transgenes described herein are either individually or collectively coded and/or expressed by the helper virus. This applies to helper viruses for both group I adenoviruses and group II adenoviruses.

Furthermore, in an embodiment of such an adenoviral replication system in accordance with the invention the adenoviral nucleic acid and/or the nucleic acid of the helper virus is/are present as replicable vector.

It is further within the present invention that the nucleic acid(s) coding for group I adenoviruses and/or group II adenoviruses is/are preferably present in an expression vector and that this expression vector is used in accordance with the invention.

In a further aspect the present invention is also related to a vector group comprising at least two vectors, whereby the vector group comprises in total an adenoviral replication system for group I adenoviruses and/or group II adenoviruses as described herein, and the vector group is used in accordance with the invention. In an embodiment each component of the adenoviral replication system is arranged on an individual vector, preferably an expression vector.

Finally, the present invention is related in a further aspect to the use of a cell which contains one or several of the nucleic acids which code for the group I adenoviruses and/or group II adenoviruses which are preferably used in accordance with the present invention, and which are to be used in accordance with the invention of and/or a corresponding adenoviral replication system and/or a corresponding vector and/or a vector group according to the invention, for the very same purpose as described herein for the various adenoviruses.

The above described constructs of adenoviruses and in particular their nucleic acids and the nucleic acids coding therefor, may also be introduced in a multipartite form into a cell, preferably a tumor cell, whereby due to the presence of the various individual components they act together as if the individual components were derived from a single nucleic acid and a single or several adenoviruses, respectively.

The nucleic acids which are used in accordance with the invention and which code for group I adenoviruses and/or group II adenoviruses, corresponding adenoviral systems or parts thereof, may also be present as vectors. Preferably these vectors are viral vectors. In case the nucleic acids comprise adenoviral nucleic acids, preferably the virus particle is the vector. It is, however, also within the present invention that said nucleic acids are present in a plasmid vector. In each case the vector comprises elements which allow for and control the propagation of inserted nucleic acid, i.e. replication and the optional expression of the inserted nucleic acid. Suitable vectors, preferably expression vectors, and respective elements are known to the ones skilled in the art and, for example, described in Grunhaus, A., Horwitz, M. S., 1994, Adenoviruses as cloning vectors. In Rice, C., editor, Seminars in Virology, London: Saunders Scientific Publications.

The aspect related to the vector groups takes into account the afore-described embodiment that the various elements of said nucleic acid are not necessarily contained in a single vector only. Accordingly, a vector group consists of at least two vectors. Apart from that, any statements made in relation to the vectors is also applicable to the vectors and the vector group, respectively.

Group I adenoviruses and/or group II adenoviruses are characterised by the various nucleic acids and gene products, respectively, disclosed herein and may otherwise comprise all those elements known to the ones skilled in the art and which are inherent to the wildtype adenoviruses (Shenk, T.: Adenoviridae: The virus and their replication. Fields Virology, vol. 3, editors Fields, B. N., Knipe, D. M., Howley, P. M. et al., Lippincott-Raven Publishers, Philadelphia, 1996, chapter 67).

For purpose of illustration but not for purpose of limitation of the present invention the replication of adenoviruses shall be briefly discussed in the following.

The replication of adenoviruses is a very complex process and is usually based on the human transcription factor E2F. During viral infection at first the "early genes" E1, E2, E3 and E4 are expressed. The group of the "late genes" is responsible for the synthesis of the structural proteins of the virus. The E1 region consisting of two transcriptional units E1A and E1B which code for different E1A and E1B proteins, play a critical role for the activation of both the early and the late genes, as they induce the transcription of the E2, E3 and E4 genes (Nevins, J. R., Cell 26, 213-220, 1981). Additionally, the E1A proteins may initiate DNA synthesis in resting cells and thus trigger their entry into the S phase (c. f. Boulanger and Blair, 1991). Additionally, they interact with the tumor suppressors of the Rb class (Whyte, P. et al., Nature 334, 124-127, 1988). In doing so, the cellular transcription factor E2F is released. The E2F factors may subsequently bind to corresponding promoter regions of both cellular and viral genes (in particular to the adenoviral E2 early promoter) and initiate transcription and thus replication (Nevins, J. R., Science 258, 424-429, 1992). The activity of pRb and E2F is regulated by phosphorylation. The hypophosphorylated form of pRb particularly exists in the G1 and M phase. In contrast thereto, the hyperphosphorylated form of pRb is present in the S and G2 phase. By phosphorylation of pRb E2F is released from the complex consisting of E2F and hypophosphorylated pRb. The release of E2F from the complex of E2F and hypophosphorylated pRb results in transcription of E2F dependent genes. The E1A protein binds only to the hypophosphorylated form of pRb, whereby the binding of E1A to pRb predominantly occurs through the CR2 region of the E1A protein. Additionally, it also binds to the CR1 region, however, with a lower affinity (Ben-Israel and Kleiberger, Frontiers in Bioscience, 7, 1369-1395, 2002; Helt and Galloway, Carcinogenesis, 24, 159-169, 2003).

The gene products of the E2 region are especially needed for the initiation and completion of the replication as they code for three essential proteins. The transcription of the E2 proteins is controlled by two promoters, the "E2 early E2F dependent" promoter, which is also referred to herein as E2-early promoter or early E2 promoter, and the "E2-late" promoter (Swaminathan and Thimmapaya, The Molecular Repertoire of Adenoviruses III: Current Topics in Microbiology and Immunology, vol 199, 177-194, Springer Verlag 1995). Additionally, the products of the E4 region together with the E1A and E1B-55 kDa protein play a crucial role for the activity of E2F and the stability of p53. For example, the E2 promoter is even more transactivated by direct interaction of the E4orf6/7 protein encoded by the E4 region with the heterodimer consisting of E2F and DP1 (Swaminathan and Thimmapaya, JBC 258, 736-746, 1996). Furthermore, the complex consisting of E1B-55 kDa and E4orf6 is inactivated by p53 (Steegenga, W. T. et al., Oncogene 16, 349-357, 1998) in order to complete a successful lytic infectious cycle. Additionally, E1B-55 kDa has a further important function insofar as it promotes, when interacting with E4orf6 protein, the export of viral RNA from the nucleus, whereas cellular RNAs are retained in the nucleus (Bridge and Ketner, Virology 174, 345-353, 1990). A further important observation is that the protein complex consisting of E1B-55 kDa/E4orf6 is localised in the so-called "viral inclusion bodies". It is assumed that these structures are the sites of replication and transcription (Ornelles and Shenk, J. Virology 65, 424-429, 1991).

The E3 region is another important region for the replication and in particular for the release of adenoviruses. The E3 region more precisely contains the genetic information for a variety of comparatively small proteins which are not essential for the infectious cycle of adenovirus in vitro, i.e. in cell culture. However, they play a crucial role in the survival of the virus during an acute and/or latent infection in vivo as they have, among others, immune regulatory and apoptotic function(s) (Marshall S. Horwitz, Virologie, 279, 1-8, 2001; Russell, supra). It could be shown that a protein having a size of about 11.6 kDa induces cell death. This protein was, due to its function, named ADP—for the english term adenovirus death protein—(Tollefson, J. Virology, 70, 2296-2306, 1996). The protein is predominantly formed in the late phase of the infectious cycle. Furthermore, the overexpression of the protein results in a better lysis of the infected cells (Doronin et al., J. Virology, 74, 6147-6155, 2000).

Furthermore, it is known to the present inventor that E1A-deleted viruses, i.e. particularly those viruses which neither express any 12S E1A protein nor any 13S E1A protein, may replicate very efficiently at higher MOIs (Nevins J. R., Cell 26, 213-220, 1981), which, however, cannot be realised in clinical applications. This phenomenon is referred to as "E1A-like activity" in literature. Furthermore it was known that of the 5 proteins encoded by E1A, two proteins, namely the 12S and the 13S protein, control and induce, respectively, the expression of the other adenoviral genes (Nevins, J. R., Cell 26, 213-220, 1981; Boulanger, P. and Blair, E.; Biochem. J. 275, 281-299, 1991). It became evident that particularly the CR3 region of the 13S protein is exhibiting the transactivating function (Wong H K and Ziff E B., J. Virol., 68, 4910-20, 1994). Adenoviruses having distinct deletions in the CR1 and/or CR2 region and/or CR3 region of the 13 S protein are essentially replication-defective, however are still transactivating in other cell lines the viral genes and promoters, and in particular the E2 region (Wong H K, Ziff E B., J. Virol. 68, 4910-20, 1994; Mymryk, J. S, and Bayley, S. T., Virus Research 33, 89-97, 1994).

After infection of a cell, typically a tumor cell, with a wildtype adenovirus, YB-1 is induced into the nucleus by means of E1A, E1B-55K and E4orf6 and co-localised with E1B-55K in the viral inclusion bodies within the nucleus which allows an effective replication of the virus in the cellular nucleus both in vitro and in vivo. It has been found already earlier that E4orf6 also binds to E1B-55K (Weigel, s. and Dobbelstein, M. J. Virology, 74, 764-772, 2000; Keith N. Leppard, Seminars in Virology, 8, 301-307, 1998) and thus mediates the transport and distribution of E1B-55K into the nucleus which ensures an optimum virus production and adenoviral replication, respectively. By the co-operation of E1A, E1B-55K and YB-1, and by the complex consisting of E1B-55K/E4orf6 and YB-1, respectively, and the co-localisation of YB-1 and E1B-55K in the nucleus in the so-called viral inclusion bodies, an efficient replication of the virus in accordance with the invention is possible and thus the use of the viruses described herein for replication in cells which are YB-1 nucleus-positive, preferably cells which contain YB-1 in the nucleus independent of the cell cycle, and/or cells which comprise or exhibit deregulated YB-1, and/or for the manufacture of a medicament, respectively, for the treatment of diseases, in which YB-1 nucleus-positive cells, preferably cells which contain YB-1 in the nucleus independent of the cell cycle, and/or cells which comprise or exhibit deregulated YB-1, are involved. The replication which is therefore possible in this cellular background, results in lysis of the cell, release of the virus and infection and lysis of adjacent cells so that in case of infection of a tumor cell and a tumor, respectively, finally lysis of the tumor, i.e. oncolysis, occurs.

YB-1 belongs to a group of highly conserved factors which bind to an inverted CAAT sequence which is referred to as Y-box. They may act in a regulatory manner both at the level of transcription and translation (Wolffe, A. P. *Trends in Cell Biology* 8, 318-323, 1998). There are more and more Y-box dependent regulation pathways found in the activation but also in the inhibition of growth and apoptosis associated genes (Swamynathan, S. K. et al., FASEB J. 12, 515-522, 1998). For example, YB-1 interacts directly with p53 (Okamoto, T. et al., Oncogene 19, 6194-6202, 2000), plays an essential role in the expression of the Fas gene (Lasham, A. et al., Gene 252, 1-13, 2000), in gene expression of MDR and MRP (Stein, U. et al., JBC 276, 28562-69, 2001; Bargou, R. C. et al., Nature Medicine 3, 447-450, 1997) and in the activation of topoisomerases and metalloproteinases (Mertens, P. R. et al., JBC 272, 22905-22912, 1997; Shibao, K. et al., Int. J. Cancer 83, 732-737, 1999). Also, YB-1 is involved in the regulation of mRNA stability (Chen, C-Y. et al., Genes & Development 14, 1236-1248, 2000) and in repair processes (Ohga, T. et al., Cancer Res. 56, 4224-4228, 1996; Izumi H. et al., Nucleic Acid Research 2001, 29, 1200-1207; Ise T. et al., Cancer Res., 1999, 59, 342-346).

The nuclear localisation of YB-1 in tumor cells either by YB-1 being present in the nucleus independent of the cell cycle, or by deregulated YB-1 present in the cytoplasm having been translocated into the nucleus by group I adenoviruses and/or group II adenoviruses, results in E1A-independent viral replication during which especially neither any 12S E1A protein nor any 13S E1A protein is expressed and used, respectively (Holm, P. S. et al. JBC 277, 10427-10434, 2002), and results in a multidrug resistance in case of overexpression of the protein YB-1. Additionally, it is known that the adenoviral proteins such as, e.g., E4orf6 and E1B-55K have a positive impact on viral replication (Goodrum, F. D. and Ornelles, D. A., J. Virology 73, 7474-7488, 1999), whereby a functional E1A protein is responsible for the activation of the other viral gene products (such as E4orf6, E3ADP and E1B-55K) (Nevins J. R., Cell 26, 213-220, 1981). This, however, does not happen with the E1A-minus adenoviruses known in the art in which the 13S E1A protein is not present. Nuclear localisation of YB-1 in multidrug resistant cells which have YB-1 in the nucleus, allows for the replication and particle formation, respectively, of such E1A-minus viruses. In connection therewith, however, the efficiency of viral replication and particle formation is reduced compared to the wildtype Ad5 by a multiple. Compared to this, a combination of YB-1 allows for a very efficient viral replication and particle formation mediated by YB-1 and thus oncolysis, whereby the YB-1 is either already contained in the nucleus of the tumor cell which may result from YB-1 being located in the nucleus in a cell cycle independent manner, or whereby the deregulated YB-1 present in the cytoplasm is translocated into the nucleus by group I adenoviruses and/or group II adenoviruses, or is induced into the cellular nucleus by exogenous factors (e.g. application of cytostatics or irradiation or hyperthermia), i.e. is induced to be present in the nucleus, particularly independent of the cell cycle, or whereby YB-1 is introduced as a transgene by a vector with a system, preferably an adenoviral system, which switches on the adenoviral genes but does not show viral replication. This applies also to the adenoviruses in accordance with the invention, i.e. group I adenoviruses, which are capable of efficiently replicating due to their specific design and using the effect that an E1B protein, preferably the E1B55K protein, and/or an E4 protein, preferably the E4orf6 protein, provide(s) for an effective mobilisation of YB-1, preferably in the nucleus. Suitable cytostatics which may be used together with the adenoviruses disclosed herein in connection with the various aspects of the present invention are, for example, those belonging to the following groups: anthracyclines such as for example daunomycin and adriamycin; alkylating agents such as for example cyclophosphamide; alkaloides such as etoposide; vin-alkaloides such as for example vincristine and vinblastine; anti-metabolites such as for example 5-fluorouracil and methothrexat; platin-derivatives such as for example cis-platin; topoisomerase inhibitors such as for example camphothecine, CPT-11; taxanes such as for example taxole, paclitaxel, histone-deacetylase inhibitors such as for example FR901228, MS-27-275, trichostatine A, MDR modulators such as for example MS-209, VX-710 and geldanamycine derivatives such as for example 17-AAG. The adenoviruses disclosed herein, in particular recombinant adenoviruses, which are only capable of replicating in cells which are YB-1 nucleus-positive, and cells which contain regulated YB-1, preferably in the cytoplasm, are limited in their ability to transactivate the viral genes E1B-55K, E4orf6, E4orf3 and E3ADP compared to the respective transactivating abilities of wildtype adenoviruses, in particular wildtype Ad5. The present inventor has surprisingly found that this limited transactivating ability can be overcome by expressing the corresponding genes, and in particular E1B-55K and E4orf6, in combination with the nuclear localisation of YB-1. As shown in the examples herein, viral replication and particle formation is increased under such conditions to a level comparable to the replication activity and particle formation activity, respectively, of wildtype adenoviruses.

The medicament in connection with which or for the manufacture of which the adenoviruses disclosed herein are used in accordance with the present invention, is intended to be applied, usually, in a systemic manner, although it is also within the present invention to apply or deliver it locally. The application is intended to infect particularly those cells with adenoviruses and it is intended that adenoviral replication particularly occurs therein, which are involved, preferably in a causal manner, in the formation of a condition, typically a disease, for the diagnosis and/or prevention and/or treatment of which the inventive medicament is used.

Such a medicament is preferably for the treatment of malignant diseases, tumor diseases, cancer diseases, cancer and tumors, whereby these terms are used herein in an essentially synonymous manner if not indicated to the contrary. The tumor diseases are preferably those where YB-1 is, due to the mechanism underlying the tumor disease, in particular due to the underlying pathological mechanism, already located in the nucleus, preferably independent of the cell cycle, or where the presence of YB-1 in the cellular nucleus is caused by exogenous measures whereby such exogenous measures are suitable to transfer YB-1 into the cellular nucleus or to induce or to express it there. The term tumor or tumor disease shall comprise herein both malignant as well as benign tumors, each both solid and diffuse tumors, and respective diseases. In an embodiment the medicament comprises at least one further pharmaceutically active compound. The nature and the amount of such further pharmaceutically active compound will depend on the kind of indication for which the medicament is used. In case the medicament is used for the treatment and/or prevention of tumor diseases, typically cytostatics such as cis-platin and taxole, daunoblastin, daunorubicin, adriamycin and/or mitoxantrone or others of the cytostatics or groups of cytostatics described herein, are used, preferably those as described in connection with the cytostatic mediated nuclear localisation of YB-1.

The medicament in accordance with the invention can be present in various formulations, preferably in a liquid form. Furthermore, the medicament will contain adjuvants such as stabilisers, buffers, preservatives and the like which are known to the one skilled in the art of formulations.

The present inventor has furthermore surprisingly found that the efficacy of the viruses described herein and in particular the viruses used in accordance with the present invention can be increased by using them in combination with at least two agents whereby each of the at least two agents is individually and independently selected from the group comprising cytostatics.

As used herein in a preferred embodiment, cytostatics are in particular chemical or biological compounds which, during or after the administration to a cell or an organism containing a or such cell, result in the cell no longer growing and/or no longer dividing or slowing down cell division and/or cell growth. Cytostatics also comprise compounds which turn into a cytostatic in the afore-described sense only in the cell or in an organism containing such cell. Insofar, the term cytostatics also comprises pre-cytostatics.

Cytostatics are grouped according to their mode of action. The following groups are distinguished which, in principle, can all be used within the present invention:

Alkylating agents, i.e. chemical compounds which cause their cytotoxic effect by alkylating phosphate, amino, sulphydryl, carboxy and hydroxy groups of the nucleic acid as well as proteins. Such compounds are often cancerogenic themselves. Typical examples of this group of cytostatics are cis-platin and platin derivatives, cyclophosphamide, dacarbazine, mitomycin, procarbazine.

Antimetabolites, i.e. compounds which, due to their structural similarity or ability for binding block a metabolic process or affect the same. Within the group of antimetabolites it is distinguished between structurally similar antimetabolites, structure changing antimetabolites and the indirectly acting antimetabolites. The structurally similar antimetabolites compete due to chemical similarity with the metabolite without exerting the function thereof. Structure changing antimetabolites bind to the metabolites which impedes its function or resorption or chemically modifies the metabolite. Indirectly acting antimetabolites interfere with the function of the metabolite, for example by the binding of ions. Typical examples of this group are folic acid antagonists such as methotrexate, pyrimidine analogues such as fluorouracil, purine analogues such as azathioprine and mercaptopurine.

Mitosis inhibitors, i.e. compounds which inhibit cell division. Within the group of mitosis inhibitors it is distinguished between cell division toxins, spindle toxins and chromosome toxins. Typical examples of this group are taxanes and vinca alkaloids. The taxanes in turn can be divided into the two major groups of taxoles and taxoters, whereby a particularly preferred taxole is paclitaxel, and a particularly preferred taxoter is docetaxel.

Antibiotics having an inhibitory effect on the DNA-dependent RNA polymerase. Typical examples are the anthracyclines, such as, e.g., bleomycin, daunorubicin, doxorubicin and mitomycin.

Topoisomerase inhibitors, in particular topoisomerase I inhibitors. Topoisomerase inhibitors are chemical compounds which determine the tertiary structure of the DNA by catalysing the change of the DNA twist number in a three stage process. Essentially, two forms of topoisomerases are distinguished. Topoisomerases of type I cleave only a DNA strand and are ATP-independent, whereas topoisomerase of type II cleave both strands of a DNA, whereby they are ATP-dependent. Typical examples for topoisomerase I inhibitors are irinotecan and topotecan, and for topoisomerase II inhibitors etoposid and daunorubicin.

Within the present invention at least one and preferably two agents are selected from the aforementioned group. It is, however, also within the invention that in particular also three, four or five different agents are selected. The following comments are made for the embodiment of the present invention where only two agents are used together with the virus. These considerations are basically also applicable to embodiments where more than two agents are used.

Preferably the agents differ from each other such that they address or target different target molecules or are described in the literature as targeting different molecules. It is within the present invention that the agent also comprises two or more different agents which bind to the same target molecule. It is also within the present invention that one agent binds to a first site of the target molecule, whereas the second agent binds to a second site of the target molecule.

It is also within the present invention that at least two of the agents are active using different modes of action. Active means in a preferred embodiment that the cell growth and/or cell division inhibiting or retarding effect of the chemical compound is mediated through a different mode of action. In a particularly preferred embodiment the term active means that the replication efficiency of a virus, in particular the virus in accordance with the present invention, of the viruses described herein and of the viruses to be used in accordance with the present invention, is increased compared to a scenario where one and/or both of the agents are not used. As a measure for the efficiency of viral replication preferably the number of viruses required for cell lysis is used, preferably expressed as pfu/cell.

In a particularly preferred embodiment at least one of the at least two agents is one which increases the infectability of the cell in which the replication of the virus is to occur, preferably is to occur in a selective manner, preferably with the virus described herein and/or the virus to be used in accordance with the present invention. This can, e.g., be performed by increasing the uptake of the virus by the cell. The uptake of the virus, in particular of adenovirus, is, for example, mediated by the coxsackievirus-adenovirus receptor (CAR) (Mizuguchi and Hayakawa, GENE 285, 69-77, 2002). An increased expression of CAR is, for example, caused by trichostatin A (Vigushin et al., Clinical Cancer Research, 7, 971-976, 2001).

In a further embodiment one of the at least two agents is one which increases the availability of a component within the cell, whereby the component is one which increases the replication of the virus, preferably the virus described herein and/or the virus to be used in accordance with the present invention.

In a further embodiment one of the at least two agents is one which mediates the transport of YB-1 into the nucleus. Such an agent can be selected from the group comprising topoisomerase inhibitors, alkylating agents, antimetabolites and mitosis inhibitors. Preferred topoisomerase inhibitors are camptothecin, irinotecan, etoposide and their respective analogues. Preferred mitosis inhibitors are daunorubicin, doxorubicin, paclitaxel and docetaxel. Preferred alkylating agents are cis-platin and their analogues. Preferred antimetabolites are fluorouracil and methotrexat.

In a particularly preferred embodiment one of the at least two agents is one which increases the infectability of the cell, in particular the expression of CAR, and the second of the at least two agents is one which increases the transport of YB-1 into the nucleus, whereby preferably as chemical compound a compound is used which exhibits the respective required characteristic as preferably described above.

In a further embodiment the one of the at least two agents is a histone deacylase inhibitor. A preferred histone deacylase inhibitor is one which is selected from the group comprising trichostatin A, FR901228, MS-27-275, NVP-LAQ824 and PXD101. Trichostatin A is, for example, described in Vigushin et al., Clinical Cancer Research, 7, 971-976, 2001; FR901228 is, for example, described in Kitazono et al., Cancer Res., 61, 6328-6330, 2001; MS-27-275 is described in Jaboin et al., Cancer Res., 62, 6108-6115, 2002; PXD101 is described in Plumb et al., Mol. Cancer Ther., 8, 721-728, 2003; NVP-LAQ824 is described in Atadja et al., Cancer Res., 64, 689-695, 2004.

In a still further embodiment the one of the at least two agents is a topoisomerase inhibitor, preferably a topoisomerase I inhibitor. A preferred topoisomerase inhibitor is one which is selected from the group comprising camptothecin, irinotecan, topotecan, SN-38, 9-aminocamptothecin, 9-nitrocamptothecin, DX-895If and daunorubicin. Irinotecan and SN-38 are, for example, described in Gilbert et al., Clinical Cancer Res., 9, 2940-2949, 2003; DX-895IF is described in van Hattum et al., British Journal of Cancer, 87, 665-672, 2002; camptothecin is described in Avemann et al., Mol. Cell. Biol., 8, 3026-3034, 1988; 9-aminocamptothecin, 9-nitrocamptothecin are described in Rajendra et al., Cancer Res., 63, 3228-3233, 2003; daunorubicin is described in M. Binaschi et al., Mol. Pharmacol., 51, 1053-1059.

In a particularly preferred embodiment the one of the at least two agents is a histone deacylase inhibitor and the other one of the at least two agents is a topoisomerase inhibitor.

In an embodiment the means according to the present invention and/or the means prepared in accordance with the present invention contains the virus separate from one or several of the at least two agents which are combined with the virus in accordance with the present invention. It is preferred that the virus is separate from any agent which is combined with the virus. Preferably the separation is a spatial separation. The spatial separation can be such that the virus is present in a different package than the agent. Preferably the package is a single dose unit, i.e. the virus and the agent are packed as single dosages or doses. The single dose units may in turn be combined to form a package. However, it is also within the present invention that the single dosages of the virus are combined with one or several single dosages of one or several of the agents or are packed therewith.

The kind of package depends on the way of administration as known to the one skilled in the art. Preferably the virus will be present in a lyophilized form or in a suitable liquid phase. Preferably, the agents will be present in solid form, e.g. as tablets or capsules, however, are not limited thereto. Alternatively, also the agents can be present in liquid form.

It is within the present invention that the virus is systemically or locally administered. It is also within the present invention that the agents combined with the virus are systemically or locally administered individually and independently from each other or together. Other modes of administration are known to the ones skilled in the art.

It is also within the present invention that the virus and the agents combined with it, are administered in a chronologically separate manner or at the same time. In connection with a chronologically separate manner it is preferred that the agents are administered prior to the administration of the virus. How long the agent is administered prior to the virus depends on the kind of the agent used and is obvious for the one skilled in the art from the mode of action of the agent used. Also the administration of the at least two agents can occur at the same or at different points in time. In connection with a chronologically different administration the points of time again result from the modes of action underlying the agents and can, based thereon, be determined by the ones skilled in the art.

The above considerations, given in connection with the medicaments according to the present invention which are also disclosed and referred to herein as pharmaceutical compositions, are roughly also applicable to any composition, including compositions as used for the replication of viruses, preferably for the in vitro replication of viruses in accordance with the present invention. The above considerations are also applicable to the kit in accordance with the present invention and the kit to be used in accordance with the present invention, respectively, which may apart from the viruses described herein and the viruses to be used in accordance with the invention, also comprise one agent or a combination of agents as described herein. Such kits comprise the virus and/or one or several agents in a form ready for use, and preferably instructions for use. Furthermore, the above embodiments apply also to the nucleic acids as disclosed herein, and the nucleic acids used in accordance with the present invention, and the replication systems in accordance with the present invention and the nucleic acids coding therefor, and, respectively, the replication systems used in accordance with the present invention and the nucleic acids coding therefor used in accordance with the present invention.

The present inventor has surprisingly found that the inventive use of the viruses described herein, preferably the use of group I adenoviruses and/or group II adenoviruses can be practised with a very high rate of success in connection with such tumors and that they can be used for the manufacture of medicaments for the treatment of such tumors, which have YB-1 in the cellular nucleus independent of the cell cycle. Normally, YB-1 is located in the cytoplasm, in particular in the perinuclear plasm. In the G1/S phase of the cell cycle YB-1 can be found in the nucleus of both normal as well as tumor cells, whereby part of the YB-1 remains in the cytoplasm [Jürchott K et al., JBC 2003, 278, 27988-27996]. This, however, is not sufficient in order to provide for viral oncolysis using such modified adenoviruses. The comparatively low efficacy of such attenuated adenoviruses as described in the prior art, is ultimately based on their wrong application. In other words, such adenoviral systems may be particularly used with a higher efficiency in case where the molecular biological prerequisites for viral oncolysis is given using these attenuated or modified adenoviruses as described herein, preferably using the group I adenoviruses and/or group II adenoviruses. In case of the adenoviruses described herein to be used in accordance with the present invention, such as AdΔ24, dl922-947, E1Ad/01/07, CB016, dl520 and the recombinant adenoviruses described in European patent EP 0 931 830, the prerequisites are given in such tumors the cells of which show a cell cycle independent nuclear localisation of YB-1. This kind of nuclear localisation may be caused by the nature of the tumor itself or by the measures or inventive agents according to the invention as described herein. The present invention thus defines a new group of tumors and tumor diseases and thus also of patients which may still be efficiently treated using the viruses according to the invention as, preferably group I adenoviruses and/or group II viruses, but also using attenuated or modified adenoviruses already described in the prior art.

A further group of patients which may be treated in accordance with the invention using group I adenoviruses and/or group II adenoviruses or the adenoviruses to be used in accordance with the present invention which are, as such, already known in the prior art, or using the adenoviruses described herein for the very first time, and preferably using such adenoviruses which have a mutation and deletion, respectively, in the E1A protein which does not interfere with the binding of Rb/E2f or which are not replicating in YB-1 nucleus-negative cells or which show a strongly reduced replication as defined herein, and/or which have and/or show a deleted oncoprotein, in particular E1A, such as, for example, in case of the viruses AdΔ24, dl922-947, E1Ad/01/07, CB106 and the adenoviruses described in European patent EP 0 931 830, are those patients in which it is ensured that by applying or realising specific conditions that YB-1 migrates into the nucleus or is induced or transported there, or that deregulated YB-1 is present. The use of group I adenoviruses and/or group II adenoviruses in connection with this group of patients is based on the finding that the induction of viral replication is based on nuclear localisation of YB-1 with subsequent binding of YB-1 to the E2-late promoter. Because of this finding disclosed herein, adenoviruses such as AdΔ24, dl922-947, E1Ad/01/07, CB106 and/or the adenoviruses described in European patent EP 0 931 830 may also replicate in such cells which are YB-1 nucleus-positive and/or in cells in which YB-1 is present in a deregulated manner in the meaning of the present invention. Insofar these adenoviruses can be used for the treatment of diseases and patient groups in accordance with the present invention which/who comprise cells having these characteristics, particularly if these cells are involved in the generation of the respective disease to be treated. This is the basis for the success of AdΔ24, dl922-947, E1Ad/01/07, CB106, of the adenoviruses described in patent EP 0 931 830 and of the group I adenoviruses and/or group II adenoviruses in the treatment according to the invention of such tumors which contain YB-1 in the nucleus independent of the cell cycle or which contain deregulated YB-1 in the meaning of the present disclosure. A further group of patients which may be treated in accordance with the present invention using the viruses described herein as to be used in accordance with the present invention and using the viruses described herein for the very first time, particularly adenoviruses and group I and/or group II adenoviruses, respectively, are those which are YB-1 nucleus-positive and/or YB-1 nucleus-positive as a result of any of the treatments in the following, and/or such patients which will undergo one of the following measures, preferably in the sense of a treatment, prior to the administration of the adenoviruses, concomitant with the application of the respective viruses or after the administration of adenoviruses. It is within the present invention that YB-1 nucleus-positive patients are patients who in particular have YB-1 in the nucleus in a number of the tumor forming cells independent of the cell cycle, and/or have deregulated YB-1 in such cells. One of these measures is the administration of cytostatics as described herein as a whole and/or as used in connection with tumor therapy. Furthermore, irradiation belongs to this group of measures, particularly irradiation as applied in the tumor therapy. Irradiation particularly means the irradiation with high energy radiation, preferably radioactive radiation, preferably as used in tumor therapy. A further measure is hyperthermia and the application of hyperthermia, respectively, preferably hyperthermia as used in tumor therapy. In a particularly preferred embodiment hyperthermia is applied locally. Finally, a further measure is hormone treatment, particularly hormone treatment as applied in tumor therapy. In the course of such hormone therapy anti-estrogens and/or anti-androgens are used. In connection therewith, anti-estrogens such as tamoxifen, are particularly used in the treatment of breast cancer, and anti-endrogens, such as for example flutamide or cyproteronacetate, are particularly used in the therapy of prostate cancer.

The adenoviruses disclosed herein may also be used for the treatment of tumors, whereby the tumor is selected from the group comprising primary tumors, secondary tumors, tertiary tumors and metastatic tumors. In connection therewith it is preferred that the tumors exhibit at least one of the following features, namely that they have YB-1 in the nucleus independent of the cell cycle, irrespective of what the reason for this is, and/or that they contain deregulated YB-1.

It is within the present invention that the cells and the tumors, respectively, comprising such cells in which the adenoviruses in accordance with the invention replicate or are capable of replicating, are those which have one or several of the features described herein, particularly the feature that they have YB-1 in the nucleus independent of the cell cycle, regardless of the reason therefor, and/or the feature that they have deregulated YB-1, and that these cells and tumors, respectively, may be treated using the group I adenoviruses and/or group II adenoviruses in accordance with the present invention, and that the adenoviruses may be used for the manufacture of a medicament for the treatment of them, whereby the adenoviruses express a YB-1 coding nucleic acid. Therefore, there are preferably three categories of cells and thus of tumors in which the group I adenoviruses and group II adenoviruses in accordance with the present invention may replicate and which may be treated and preferably lysed using these adenoviruses, respectively:

Group A: Cells which have YB-1 in the nucleus independent of the cell cycle;
Group B: Cells which do not have YB-1 in the nucleus, particularly not independent of the cell cycle, but comprise deregulated YB-1; and
Group C: Cells which do not have YB-1 in the nucleus, particularly not independent of the cell cycle, and which do not comprise deregulated YB-1.

For the cells of group A the adenoviruses in accordance with the present invention, particularly group I adenoviruses, which do not express additional YB-1, may be used for replication or lysis. However, it is also possible that such adenoviruses in accordance with the present invention, in particular group I adenoviruses which express additional YB-1, are used for replication and lysis. This applies also to group B. Without wishing to be bound thereto, the reason seems to be that due to the effect of the E1B protein, in particular the E1B55K protein, and/or the E4 protein, particularly the E4orf6 protein, an efficient replication is ensured by localisation of YB-1 in the nucleus and the transfer of the same to the nucleus, respectively. YB-1 additionally expressed by the adenoviruses, supports this process.

In case of group C, preferably those adenoviruses in accordance with the invention, particularly group I adenoviruses will be used for replication or lysis which additionally express YB-1. The reason for this seems to be, again without wishing to be bound thereto, that the above processes of viral replication are not active in the particular cellular background such that an efficient replication may occur. Only by providing YB-1 and expressing YB-1, respectively, an efficient replication may occur, whereby the underlying mechanism seems to be such that the overexpression of YB-1 results in nuclear localisation of YB-1 as also described by Bargou [Bargout R. C. et al., Nature Medicine 1997, 3, 447-450) and Jürchott [Jürchott K. et al., JBC 2003, 278, 27988-27966].

It is within the present invention that some of the tumor forming cells which either inherently contain YB-1 in the nucleus or do so or after induction and active introduction into the nucleus or which comprise deregulated YB-1 in the meaning of the present disclosure. Preferably about 5% or any percentage higher than that, i.e. 6%, 7%, 8% etc., of the tumor forming cells are such YB-1 nucleus-positive cells or cells in which deregulated YB-1 is present. For other tumors such as breast tumor, osteosarcoma, ovarian carcinoma, synovial carcinoma or lung carcinoma the percentage of tumor cells which comprise deregulated YB-1 or which show nuclear localisation of YB-1 independent of the cell cycle, may be about 30 to 50% [Kohno K. et al., BioEssays 2003, 25, 691-698]. Such tumors may preferably be treated using the adenoviruses in accordance with the present invention. Nuclear localisation of YB-1 may be induced by outside stress and locally applied stress, respectively. This induction may occur through irradiation, particularly UV-irradiation, application of cytostatics as, among others, also disclosed herein, and hyperthermia. In connection with hyperthermia it is important that it may be realized in a very specific manner, particularly a local manner, and that thus also a specific nuclear transport of YB-1 into the nucleus may be caused and, because of this, the prerequisites for replication of the adenovirus and thus of cell and tumor lysis are given, which preferably is locally limited (Stein U, Jurchott K, Walther W, Bergmann, S, Schlag P M, Royer H D. J Biol Chem. 2001, 276(30):28562-9; Hu Z, Jin S, Scotto K W. J Biol Chem. 2000 Jan. 28; 275(4):2979-85; Ohga T, Uchiumi T, Makino Y, Koike K, Wada M, Kuwano M, Kohno K. J Biol Chem. 1998, 273(11):5997-6000).

The medicament of the invention would thus also be administered to patients and groups of patients or would be designed for them, where by appropriate pre- or post-treatment or concomitant treatment a transport of YB-1, particularly in the respective tumor cells, is caused and deregulated YB-1 is generated in the cell, respectively.

Based on the technical teaching provided herein, it is within the skills of the one of the art to suitably modify particularly E1A which may, for example, comprise the generation of deletions or point mutations in order to thus generate different embodiments of the adenoviruses which may be applied in the use in accordance with the present invention.

As already mentioned, group I and/or group II adenoviruses are capable of replicating in such cells and cellular systems, which have YB-1 in the nucleus. For the question whether also these adenoviruses used in accordance with the invention are capable of replicating and are thus capable of tumor lysis, the status of the cells with regard to the presence or absence of Rb, i.e. the retinoblastome tumor suppressor product, is irrelevant. Furthermore, for the use of said adenoviruses in accordance with the present invention, it is not necessary to take into account the p53 status of the infected cells, of the cells to be infected or of the cells to be treated as, when using the adenoviral systems disclosed herein in connection with YB-1 nucleus-positive cells, i.e. cells having YB-1 in the nucleus independent of the cell status, the p53 status as well as the Rb status does not have any impact on the replication of the adenovirus for the practising the technical teaching disclosed herein.

The transactivating oncogene and oncogene protein, respectively, in particular E1A, preferably of the group II adenoviruses, can be either under the control of the proprietary natural adenoviral promoters and/or be controlled through a tumor-specific or tissue-specific promoter. Suitable non-adenoviral promoters can be selected from the group comprising cytomegalovirus promoter, RSV (rous sarcoma virus) promoter, adenovirus-based promoter Va I and the non-viral YB-1 promoter (Makino Y. et al., Nucleic Acids Res. 1996, 15, 1873-1878). Further promoters which may be used in connection with any aspect of the invention disclosed herein, are the telomerase promoter, the alpha-fetoprotein (AFP) promoter, the carcinoembryonic antigen promoter (CEA) (Cao, G., Kuriyama, S., Gao, J., Mitoro, A., Cui, L., Nakatani, T., Zhang, X., Kikukawa, M., Pan, X., Fukui, H., Qi, Z. Int. J. Cancer, 78, 242-247, 1998), the L-plastin promoter (Chung, I., Schwartz, P E., Crystal, R C., Pizzorno, G, Leavitt, J., Deisseroth, A B. Cancer Gene Therapy, 6, 99-106, 1999), argenine vasopressin promoter (Coulson, J M, Staley, J., Woll, P J. British J. Cancer, 80, 1935-1944, 1999), E2f promoter (Tsukada et al., Cancer Res., 62, 3428-3477, 2002), uroplakin II promoter (Zhang et al., Cancer Res., 62, 3743-3750, 2002) and the PSA promoter (Hallenbeck P L, Chang, Y N, Hay, C, Golightly, D., Stewart, D., Lin, J., Phipps, S., Chiang, Y L. Human Gene Therapy, 10, 1721-1733, 1999), tyrosinase promoter (Nettelbeck, D M. Anti-Cancer Drugs, 14, 577-584, 2003), cyclooxygenase 2 promoter (Nettelbeck, D M., Rivera, A A, Davydova, J., Dieckmann, D., Yamamoto, M., Curiel, D T. Melanoma Res., 13, 287-292, 2003) and inducing systems such as tetracycline (Xu, X L., Mizuguchi, H., Mayumi, T., Hayakawa, T. Gene, 309, 145-151, 2003). Furthermore, the YB-1 dependent E2 late promoter of adenoviruses as described in German patent application DE 101 50 984.7 is a promoter which may be used in connection with the present invention.

About the telomerase promoter it is known that it is of crucial importance in human cells. Accordingly, telomerase activity is regulated through transcriptional control of the telomerase reverse transcriptase gene (hTERT) which is a catalytic subunit of the enzyme. Expression of the telomerase is active in 85% of the human tumor cells. In contrast thereto it is inactive in most normal cells. Except therefrom are germ cells and embryonic tissue (Braunstein, I. et al., Cancer Research, 61, 5529-5536, 2001; Majumdar, A. S. et al., Gene Therapy 8, 568-578, 2001). Detailed studies of the hTERT promoter have shown that the fragments of the promoter separated from the initiation codon 283 by and 82 bp, respectively, are sufficient for specific expression in tumor cells (Braunstein I. et al.; Majumdar A S et al., supra). Therefore, this promoter and the specific fragments, respectively, are suitable for specific expression in tumor cells of a gene and in particular of a transgene, preferably one of the transgenes disclosed herein. The promoter is to allow for the expression of the modified oncogene, preferably the E1A oncogene protein, in tumor cells only. Also, in an embodiment the expression of a transgene in an adenoviral vector under the control of these promoters is contemplated, preferably of a transgene which is selected from the group comprising E4orf6, E1B55 kD, ADP and YB-1. It is also within the present invention that the reading frame of the transactivating oncogene protein, in particular the E1A protein is in frame with one or several gene products of the adenoviral system. The reading frame of the transactivating E1A protein, however, may also be independent therefrom.

The various transgenes, thus also E1B55 kD, E4orf6, ADP and the like, in particular if they are viral genes, can, in principle, be cloned from any respective virus, preferably adenovirus. In the prior art furthermore a multitude of plasmids is described which contain respective genes and from which these may subsequently be taken and introduced into the adenoviruses of the present invention as well as into the viruses used in accordance with the present invention. An example for such a plasmid which expresses E1B55 kD, is, for example, described by Dobbelstein, M. et al., EMBO Journal, 16, 4276-4284, 1997. The coding region of the E1B55K gene can be excised together with the 3' non-translating region for example from this gene by Bam HI from plasmid pDCRE1B. The corresponding fragment comprising the E1B55kD gene as well as the 3' non-coding region corresponds to nucleotides 2019-4107 of adenovirus type 5. It is, however, also within the present invention that the E1B55kD gene is excised by means of restriction enzyme Bam HI and BfrI from said plasmid and is subsequently cloned into the adenovirus.

It is within the present invention that, if not indicated to the contrary, in case it is referred to viruses of the present invention it is referred to both the nucleic acid coding therefore as well as the adenoviral particles, preferably including the respective nucleic acid. The respective nucleic acid may also be present as being integrated in a different vector.

It is within the present invention that the various promoters described above are also used in connection with the various embodiments of the adenoviruses in accordance with the invention, preferably the group I adenoviruses, particularly in case a promoter is to be used which is different from the one which controls the expression of the respective protein or expression product in wildtype adenoviruses. The aforementioned promoters are thus suitable heterologous promoters in the meaning of the present invention. In preferred embodiments of the adenoviruses in accordance with the invention, particularly the group I adenoviruses, it is contemplated that when applying the adenoviruses for cells of group A and B as defined above, this occurs such that the expression of the E1B protein and/or the E4 protein starts from such heterologous promoters, whereby preferably, but not exclusively, the expression of the E1A protein is controlled by YB-1. The expression of the E1A protein is in this and other embodiments under the control of a YB-1 controllable promoter such as for example the adenoviral E2-late promoter. This is also true in that case where the E1B protein and/or the E4 protein is/are expressed in an expression cassette.

In preferred embodiments of the adenoviruses in accordance with the invention, particularly the group I adenoviruses, it is contemplated that when applying the adenoviruses in connection with cells of group C the promoter is each and independently a tumor-specific, organ-specific or tissue-specific promoter. In connection therewith it is sufficient when at least one of the promoters which control the expression of the E1B protein, the E4 protein and/or the E1A protein, is such a specific promoter. By this tumor, organ and tissue specificity, it is ensured that replication of the adenoviruses in accordance with the invention happens only in cells of the respective tumor, organ or tissue and that, apart from that, no further tissue is damaged by the replication of the adenoviruses such as, for example, is lysed. Preferably, still a second and more preferably all three proteins are controlled by such tumor-specific, organ-specific or tissue-specific promoters. Using such adenoviruses it is possible to lyse also those cells which do not form a tumor or which cannot develop into such tumor, but which are for other reasons such as medicinal reasons to be destroyed or to be removed from the organism, preferably a mammalian and more preferably a human organism, for example because they produce an undesired factor or produce such factor at a too high level.

It is contemplated that, in an embodiment, the cells for the lysis of which the described adenoviruses in accordance with the invention are used, are resistant, preferably show a multiple resistance.

Resistances as referred to herein and which are characteristic for the tumors and patients to be treated, are those which are mediated by the following genes, however, are not limited thereto: MDR, MRP, topoisomerase, BCL2, glutathione-2-transferase (GST), protein kinase C (PKC). As the effect of cytostatics is based, among others, on the induction of apoptosis, the expression of apoptosis-relevant genes plays a crucial role in the generation of any resistance so that the following factors are also relevant with regard thereto, namely Fas, the BCL2 family, HSP 70 and EGFR [Kim et al., Cancer Chemther. Pharmacol. 2002, 50, 343-352].

It has been described by Levenson et al. [Levenson, V. V. et al., Cancer Res., 2000, 60, 5027-5030] that the expression of YB-1 is strongly increased in resistant tumor cells compared to non-resistant tumor cells.

Resistance as used herein, preferably refers to a resistance against the cytostatics described herein. This multiple resistance preferably goes along with the expression, preferably an overexpression, of the membrane bound transporter protein P glycoprotein which may be used as a marker for determining respective cells and thus also of tumors exhibiting such marker and respective patient groups. The term resistance as used herein also comprises both the resistance which is referred to as classical resistance mediated through P glycoprotein, as well as the resistance referred to as atypical resistance which is mediated by MRP or other, non-P-glycoprotein mediated resistances. A further marker which correlates with the expression of YB-1 is topoisomerase II alpha. Insofar topoisomerase II alpha may be used in a screening method instead of or in addition to determining YB-1 in the nucleus in order to decide whether a patient may be treated in accordance with the invention using the adenoviruses with an expectation of success. A marker which, in principle, may be similarly used as the P glycoprotein, is MRP. A further marker, at least to the extent that colorectal carcinoma cells or patients having colorectal carcinoma are concerned, is PCNA (proliferating cell nuclear antigen) (Hasan S. et al., Nature, 15, 387-391, 2001), as, for example, described by Shibao K. et al. (Shibao K et al., Int. Cancer, 83, 732-737, 1999). Finally, at least in the field of breast cancer and osteosarcoma cells, the expression of MDR (multiple drug resistance) is a marker in the afore-described meaning (Oda Y et al., Clin. Cancer Res., 4, 2273-2277, 1998). A further potential marker which may be used in accordance with the invention is p73 (Kamiya, M., Nakazatp, Y., J Neurooncology 59, 143-149 (2002); Stiewe et al., J. Biol. Chem., 278, 14230-14236, 2003).

Finally, it shall also be referred to YB-1 as a prognostic marker in breast cancer which may be used in the present invention. Only in patients having increased expression of YB-1 in the primary tumor, a recurrence occurs after surgery and chemotherapy [Janz M. et al. Int. J. Cancer 2002, 97, 278-282].

It is a particular advantage of the present invention that also those patients may be subject to treatment using in accordance with the invention the adenoviruses described herein, which otherwise cannot be treated anymore in the medicinal-clinical sense and where thus a further treatment of the tumor diseases using the methods of the prior art is no longer possible with an expectation of success, in particular where the use of cytostatics and irradiation is no longer reasonably possible and cannot be successfully carried out any longer in the sense of influencing or reducing the tumor. Herein the term tumor refers in general also to any tumor or cancer disease which either inherently contains YB-1 in the cellular nucleus, preferably independent of the cell cycle, or does so by applying exogenous measures, as disclosed herein, and/or which contains deregulated YB-1.

Additionally, the viruses described herein can, in principle, be used for the treatment of tumors.

The tumours which can in particular be treated by the viruses described herein are preferably those tumours which are selected from the group comprising tumours of the nervous system, ocular tumours, tumours of the skin, tumours of the soft tissue, gastrointestinal tumours, tumours of the respiratory system, tumour of the skeleton, tumours of the endocrine system, tumours of the female genital system, tumours of a mammary gland, tumours of the male genital system, tumours of the urinary outflow system, tumours of the haematopoietic system including mixed and embryonic tumours. It is within the present invention that these tumours are in particular resistant tumours as in particular defined herein.

The group of tumors of the nervous system preferably comprises:
1. Tumors of the skull as well as of the brain (intracranial), preferably astrocytoma, oligodendroglioma, meningioma, neuroblastoma, ganglioneuroma, ependymoma, schwannoglioma, neurofibroma, haemangioblastoma, lipoma, craniopharyngioma, teratoma and chordoma;
2. Tumors of the spinal cord and of the vertebral canal, preferably glioblastoma, meningioma, neuroblastoma, neurofibroma, osteosarcoma, chondrosarcoma, haemangiosarcoma, fibrosarcoma and multiple myeloma; and
3. Tumors of the peripheral nerves, preferably schwannoglioma, neurofibroma, neurofibrosarcoma and perineural fibroblastoma.

The group of the ocular tumors preferably comprises:
1. Tumors of the eyelids and of the lid glands, preferably adenoma, adenocarcinoma, papilloma, histiocytoma, mast cell tumor, basal-cell tumor, melanoma, squamous-cell carcinoma, fibroma and fibrosarcoma;
2. Tumors of the conjunctiva and of the nictitating membrane, preferably squamous-cell carcinoma, haemangioma, haemangiosarcoma, adenoma, adenocarcinoma, fibrosarcoma, melanoma and papilloma; and
3. Tumors of the orbita, the optic nerve and of the eyeball, preferably retinoblastoma, osteosarcoma, mast cell tumor, meningioma, reticular cell tumor, glioma, schwannoglioma, chondroma, adenocarcinoma, squamous-cell carcinoma, plasma cell tumor, lymphoma, rhabdomyosarcoma and melanoma.

The group of skin tumors preferably comprises:
Tumors of the histiocytoma, lipoma, fibrosarcoma, fibroma, mast cell tumor, malignant melanoma, papilloma, basal-cell tumor, keratoacanthoma, haemangiopericytoma, tumors of the hair follicles, tumors of the sweat glands, tumors of the sebaceous glands, haemangioma, haemangiosarcoma, lipoma, liposarcoma, malignant fibrous histiocytoma, plasmacytoma and lymphangioma.

The group of tumors of the soft-tissues preferably comprises:
Tumors of the alveolar soft-tissue sarcoma, epithelioid cell sarcoma, chondrosarcoma of the soft-tissue, osteosarcoma of the soft-tissues, Ewing's sarcoma of the soft-tissues, primitive neuroectodermal tumors (PNET), fibrosarcoma, fibroma, leiomyosarcoma, leiomyoma, liposarcoma, malignant fibrous histiocytoma, malignant haemangiopericytoma, haemangioma, haemangiosarcoma, malignant mesenchymoma, malignant peripheral nerve sheath tumor (MPNST, malignant schwannoglioma, malignant melanocytic schwannoglioma, rhabdomyosarcoma, synovial sarcoma, lymphangioma and lymphangiosarcoma.

The group of gastrointestinal tumors preferably comprises:
1. Tumors of the oral cavity and of the tongue, preferably squamous-cell carcinoma, fibrosarcoma, Merkel cell tumor, inductive fibroameloblastoma, fibroma, fibrosarcoma, viral papillomatosis, idiopathic papillomatosis, nasopharyngeal polyps, leiomyosarcoma, myoblastoma and mast cell tumor;
2. Tumors of the salivary glands, preferably adenocarcinoma;
3. Tumors of the oesophagus, preferably squamous-cell carcinoma, leiomyosarcoma, fibrosarcoma, osteosarcoma, Barrett carcinoma and paraoesophageal tumors;
4. Tumors of the exocrine pancreas, preferably adenocarcinoma; and
5. Tumors of the stomach, preferably adenocarcinoma, leiomyoma, leiomyosarcoma and fibrosarcoma.

The group of the tumors of the respiratory system preferably comprises:
1. Tumors of the nose and nasal cavity, of the larynx and of the trachea, preferably squamous-cell carcinoma, fibrosarcoma, fibroma, lymphosarcoma, lymphoma, haemangioma, haemangiosarcoma, melanoma, mast cell tumor, osteosarcoma, chondrosarcoma, oncocytoma (rhabdomyoma), adenocarcinoma and myoblastoma; and
2. Tumors of the lung, preferably squamous-cell carcinoma, fibrosarcoma, fibroma, lymphosarcoma, lymphoma, haemangioma, haemangiosarcoma, melanoma, mast cell tumor, osteosarcoma, chondrosarcoma, oncocytoma (rhabdomyoma), adenocarcinoma, myoblastoma, small-cell carcinoma, non-small cell carcinoma, bronchial adenocarcinoma, bronchoalveolar adenocarcinoma and alveolar adenocarcinoma.

The group of the skeleton tumors preferably comprises:
osteosarcoma, chondrosarcoma, parosteal osteosarcoma, haemangiosarcoma, synovial cell sarcoma, haemangiosarcoma, fibrosarcoma, malignant mesenchymoma, giant-cell tumor, osteoma and multilobular osteoma.

The group of the tumors of the endocrine system preferably comprises:
1. Tumors of the thyroid gland/parathyroid, preferably adenoma and adenocarcinoma;
2. Tumors of the suprarenal gland, preferably adenoma, adenocarcinoma and pheochromocytoma (medullosuprarenoma);
3. Tumors of the hypothalamus/hypophysis, preferably adenoma and adenocarcinoma;
4. Tumors of the endocrine pancreas, preferably insulinoma (beta cell tumor, APUDom) and Zollinger-Ellison syndrome (gastrin secernent tumor of the delta cells of the pancreas); and
5. as well as multiple endocrine neoplasias (MEN) and chemodectoma.

The group of the tumors of the female sexual system tumors preferably comprises:
1. Tumors of the ovaries, preferably adenoma, adenocarcinoma, cystadenoma, and undifferentiated carcinoma;
2. Tumors of the uterine, preferably leiomyoma, leiomyosarcoma, adenoma, adenocarcinoma, fibroma, fibrosarcoma and lipoma;
3. Tumors of the cervix, preferably adenocarcinoma, adenoma, leiomyosarcoma and leiomyoma;
4. Tumors of the vagina and vulva, preferably leiomyoma, leiomyosarcoma, fibroleiomyoma, fibroma, fibrosarcoma, polyps and squamous-cell carcinoma.

The group of tumors of the mammary glands preferably comprises:
fibroadenoma, adenoma, adenocarcinoma, mesenchymal tumora, carcinoma, carcinosarcoma.

The group of the tumors of the male sexual system preferably comprises:
1. Tumors of the testicles, preferably seminoma, interstitial-cell tumor and Sertoli cell tumor;
2. Tumors of the prostate, preferably adenocarcinoma, undifferentiated carcinoma, squamous-cell carcinoma, leiomyosarcoma and transitional cell carcinoma; and
3. Tumors of the penis and the external genitals, preferably mast cell tumor and squamous-cell carcinoma.

The group of tumors of the urinary outflow system preferably comprises:
1. Tumors of the kidney, preferably adenocarcinoma, transitional cell carcinoma (epithelial tumors), fibrosarcoma, chondrosarcoma (mesenchymal tumors), Wilm's tumor, nephroblastoma and embryonal nephroma (embryonal pluripotent blastoma);
2. Tumors of the ureter, preferably leiomyoma, leiomyosarcoma, fibropapilloma, transitional cell carcinoma;
3. Tumors of the urinary bladder, preferably transitional cell carcinoma, squamous-cell carcinoma, adenocarcinoma, botryoid (embryonal rhabdomyosarcoma), fibroma, fibrosarcoma, leiomyoma, leiomyosarcoma, papilloma and haemangiosarcoma; and
4. Tumors of the urethra, preferably transitional cell carcinoma, squamous-cell carcinoma and leiomyosarcoma.

The group of tumors of the haematopoietic system preferably comprises:
1. Lymphoma, lymphatic leukemia, non-lymphatic leukemia, myeloproliferative leukemia, Hodgkin's lymphoma, Non-Hodgkin's lymphoma.

The group of the mixed and embryonal tumors preferably comprises:
Haemangiosarcoma, thymoma and mesothelioma.

In a particularly preferred embodiment these tumors are selected from the group comprising breast cancer, ovary carcinoma, prostate carcinoma, osteosarcoma, glioblastoma, melanoma, small-cell lung carcinoma and colorectal carcinoma. Further tumors are those which are resistant as described herein, preferably those which are multiple resistant, particularly also those tumors of the group described above. Especially preferred tumors are also those selected from the group comprising breast tumors, bone tumors, stomach tumors, intestinal tumors, gallbladder tumors, pancreatic tumors, liver tumors, kidney tumors, brain tumors, ovary tumors, tumors of the skin and of cutaneous appendages, head/neck tumors, uterus tumors, synovial tumors, larynx tumors, oesophageal tumors, tongue tumors and prostate tumors. It is preferred that these tumors are those which are, regarding their manifestations, disclosed herein altogether.

The adenoviruses of the invention, preferably the group I adenoviruses and the adenoviruses to be used in accordance with the invention, preferably the group II adenoviruses.

The use of the adenoviruses disclosed herein, particularly group I adenoviruses and/or group II adenoviruses as medicaments and in particular in connection for systemic administration can be improved by a suitable targeting of the adenoviruses. The infection of tumor cells by adenoviruses depends, among others, to a certain extent on the presence of the coxackievirus-adenovirus receptor CAR and distinct integrins. As soon as they are strongly expressed in cells, preferably tumor cells, an infection is possible already at very low titers (pfu/cell). Various strategies have been tried to date in order to reach a so-called re-targeting of recombinant adenoviruses, for example by inserting heterologous sequences in the fiber knob region, using bi-specific antibodies, coating of the adenoviruses with polymers, introducing ligands in the Ad fiber, substituting the serotype 5 knob and serotype 5 fiber shaft and knop by the serotype 3 knob and Ad 35 fiber shaft and knob, and modification of the penton base, respectively (Nicklin S. A. et al., Molecular Therapy 2001, 4, 534-542; Magnusson, M. K. et al., J. of Virology 2001, 75, 7280-7289; Barnett B. G. et al., Biochimica et Biophysica Acta 2002, 1575, 1-14). The realisation in connection with the various aspects of the present invention of such further embodiments and features, respectively, in the adenoviruses in accordance with the invention and the adenoviruses used in accordance with the invention, particularly in group I adenoviruses and group II adenoviruses, is within the present invention.

The invention is related in a further aspect to a method for the screening of patients which may be treated using a modified adenovirus, i.e. an adenovirus as used in accordance with the invention, such as, for example, AdΔ24, dl922-947, E1Ad/01/07, CB016 or the viruses described in European patent EP 0 931 830, and/or a group I adenovirus and/or group II adenovirus, whereby the method comprises the following steps:

Analysing a sample of the tumor tissue and
Determining whether YB-1 is localised in the nucleus independent of the cell cycle, or whether the cells contain deregulated YB-1.

Instead of or in addition to YB-1 also the presence of the afore-described markers can be assessed.

In case that the tumor tissue or a part thereof comprises YB-1 in the nucleus, preferably independent of the cell cycle, or comprises deregulated YB-1, the adenoviruses as disclosed herein, particularly group I adenoviruses and/or group II adenoviruses may be used in accordance with the present invention.

In an embodiment of the method according to the invention it is contemplated that the analysis of the tumor tissue occurs by means of an agent which is selected from the group comprising antibodies against YB-1, aptamers against YB-1, spiegelmers against YB-1 as well as anticalines against YB-1. In principle, the same kind of agents can also be made and used, respectively, for the respective markers. The manufacture of antibodies, in particular monoclonal antibodies, is known to the ones skilled in the art. A further agent for specific detection of YB-1 or the markers are peptides which bind with a high affinity to their target structures, in the present case YB-1 or said markers. In the prior art methods are known such as, for example, phage-display, in order to generate such peptides. For such purpose, it is started from a peptide library whereby the individual peptides have a length of about 8 to 20 amino acids and the size of the library is about $10^2$ to $10^{18}$, preferably $10^8$ to $10^{15}$ different peptides. A particular form of target molecule binding polypeptides are the so-called anticalines which are, for example, described in German patent application DE 197 42 706.

A further agent for specifically binding to YB-1 or the corresponding markers disclosed herein and thus for the detection of a cell cycle independent localisation of YB-1 in the nucleus, are the so-called aptamers, i.e. D-nucleic acids, which, based on RNA or DNA, are present as either a single strand or a double strand and specifically bind to a target molecule. The generation of aptamers is, for example, described in European patent EP 0 533 838. A special embodiment of aptamers are the so-called aptazymes which, for example, are described by Piganeau, N. et al. (2000), Angew. Chem. Int. Ed., 39, no. 29, pages 4369-4373. They are a particular embodiment of aptamers insofar as they comprise apart from the aptamer moiety a ribozyme moiety and, upon binding or release of the target molecule binding to the aptamer moiety, the ribozyme moiety becomes catalytically active and cleaves a nucleic acid substrate which goes along with generation of a signal.

A further form of the aptamers are the so-called spiegelmers, i.e. target molecule binding nucleic acids which consist of L-nucleic acids. The method for the generation of such spiegelmers is, for example, described in WO 98/08856.

The sample of the tumor tissue can be obtained by punctuation or surgery. The assessment whether YB-1 is located in the nucleus independent of the cell cycle is frequently done by the use of microscopic techniques and/or immunohistoanalysis, typically using the antibody or any of the further agents described above. Further methods for the detection of YB-1 in the nucleus and that its localisation there is independent of the cell cycle, are known to the one skilled in the art. For example, localisation of YB-1 can easily be detected when scanning tissue slices stained against YB-1. The frequency of YB-1 being in the nucleus is already an indication that the localisation in the nucleus is independent of the cell cycle. A further possibility for cell cycle independent detection of YB-1 in the nucleus is the staining against YB-1 and assessment whether YB-1 is localised in the nucleus and determining the phase of the cells. This and the detection of YB-1, respectively, however, can also be performed using the afore-mentioned agents directed against YB-1. The detection of the agents is done by procedures known to the one skilled in the art. Because said agents are specifically directed against YB-1 and insofar do not bind to other structures within the sample to be analysed, particularly other structures of the cells, both the localisation of said agents by means of a suitable labelling of the agents and due to their specific binding to YB-1, also the localisation of YB-1 can be detected and assessed accordingly. Methods for the labelling of the agents are known to the ones skilled in the art. The same techniques may also be used in order to determine whether and if so how many of the cells of the sample contain deregulated YB-1. As deregulated YB-1 also shows an overexpression compared to non-deregulated YB-1, the relative expression of YB-1 compared to a reference sample may be used in order to determine whether YB-1 is deregulated in the analysed cell.

It is within the present invention that the viruses described herein, whether they are the viruses of the present invention or whether they are the viruses to be used in accordance with the present invention, are also used in connection with diseases, preferably tumor diseases and more preferably tumor diseases where at least a part of the tumor cells exhibits a multiple resistance, in particular a multi-drug resistance, in which YB1 is deregulated. This applies also to each and any other aspect as described herein in connection with the cells and tumors to the extent that it refers to cells and diseases where YB1 is present in the nucleus, preferably independent of the cell cycle.

The present invention shall now be further illustrated using the figures and examples, whereby novel features, embodiments and advantages of the invention may be taken therefrom. In connection therewith FIG. 1 shows the structural design of the adenoviral vectors referred to therein as AdE1/E3-minus adenoviral vectors which are E1/E3-deleted adenoviruses, of wildtype adenovirus and of adenovirus dl520;

FIG. 7 shows the structural design of the E1A protein of wildtype adenovirus, of adenovirus dl520 and of adenovirus dl1119/1131;

FIG. 16 shows the structural design of wildtype adenovirus and the adenoviral vector AdXVir03;

Figure 19:
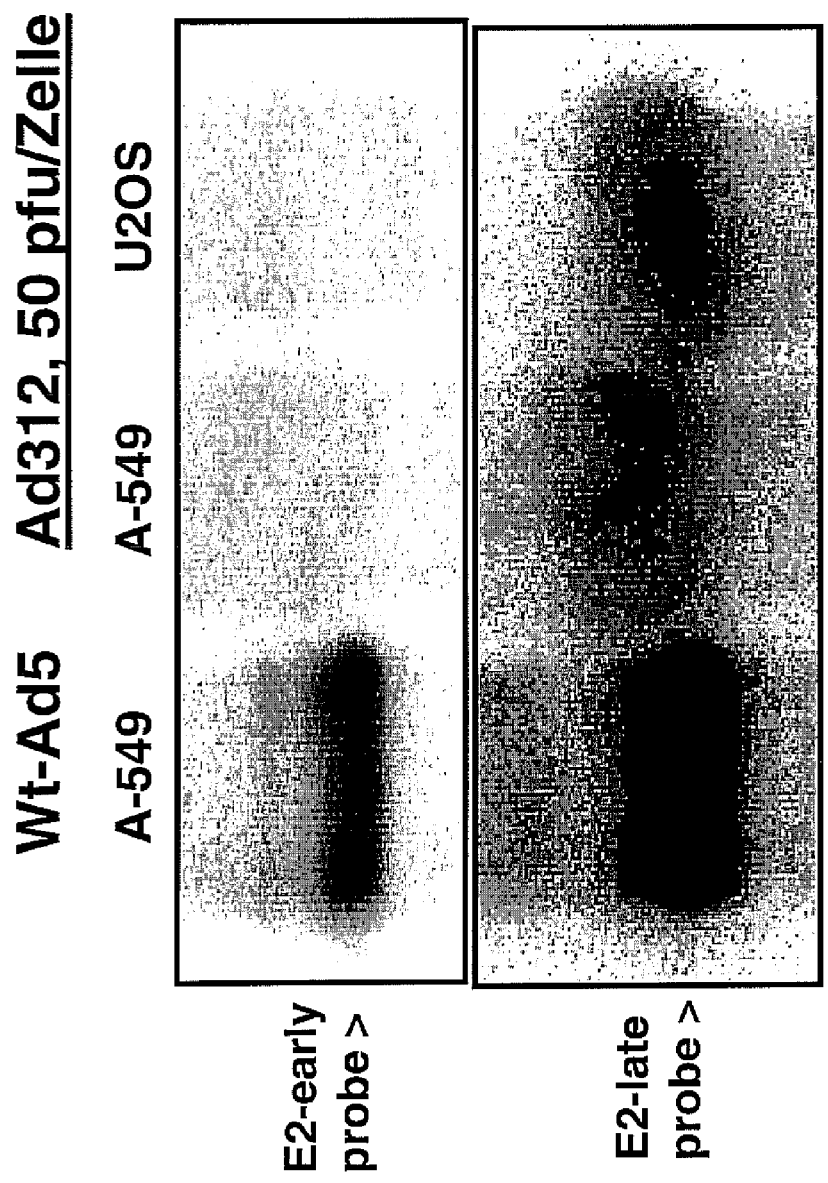
Figure 20:
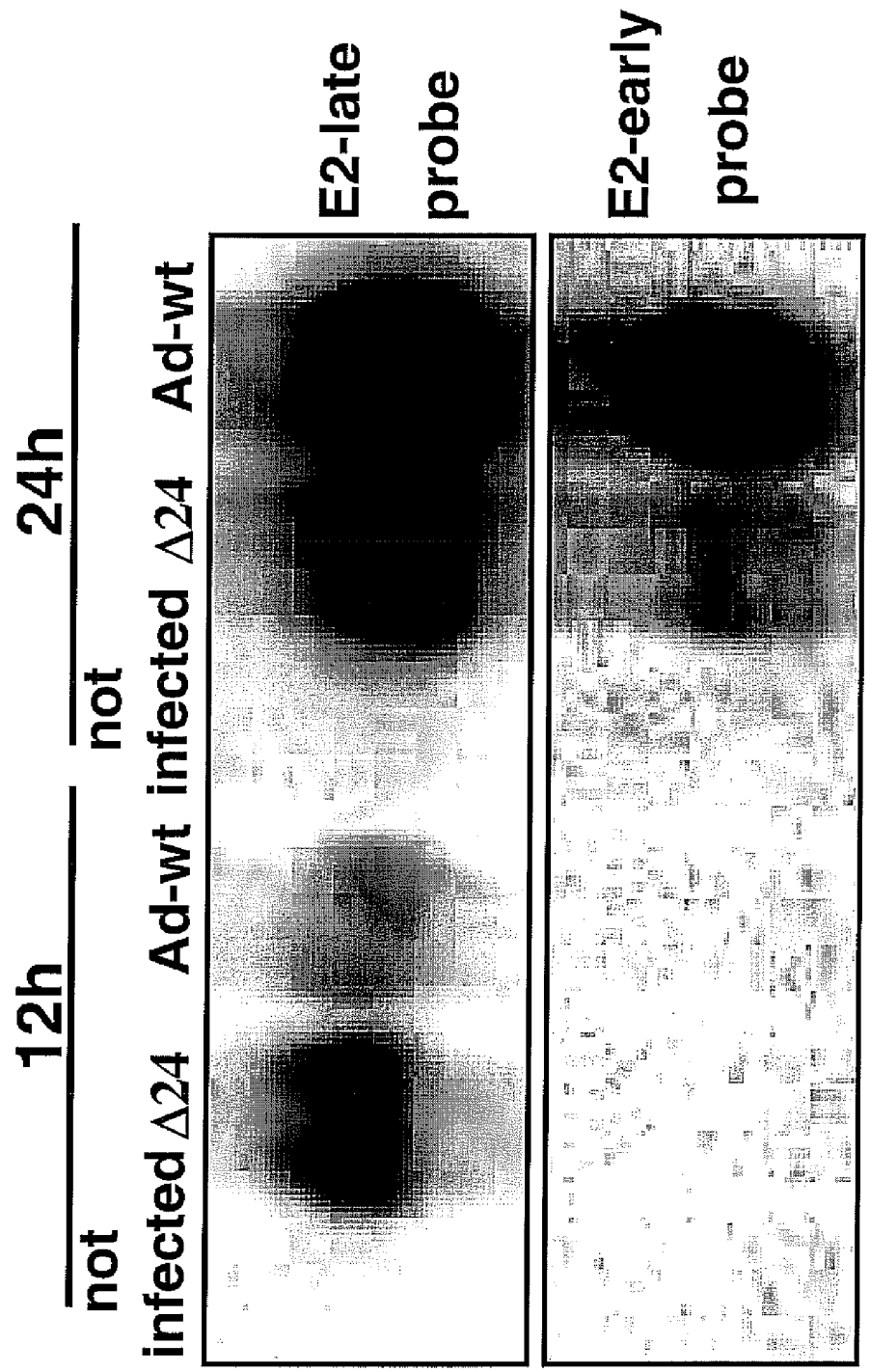
Figure 21:
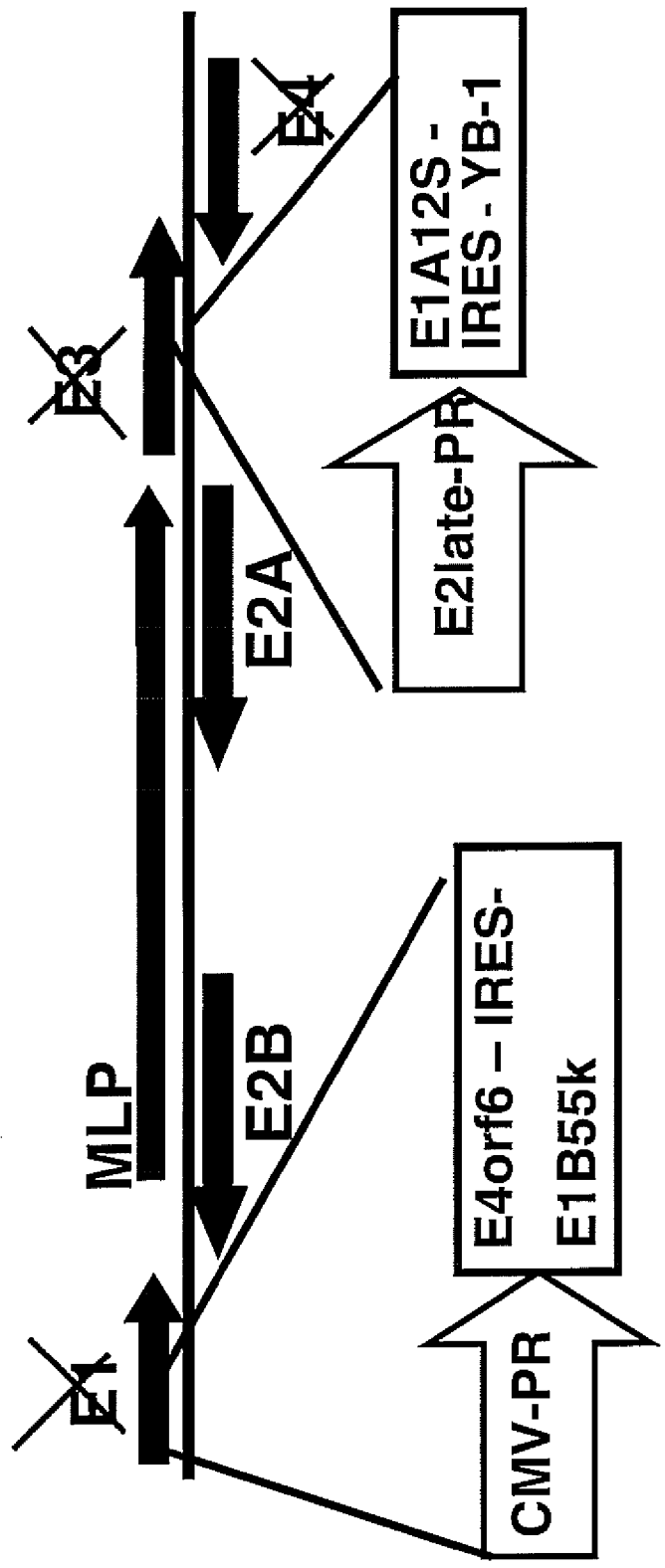
Figure 22:
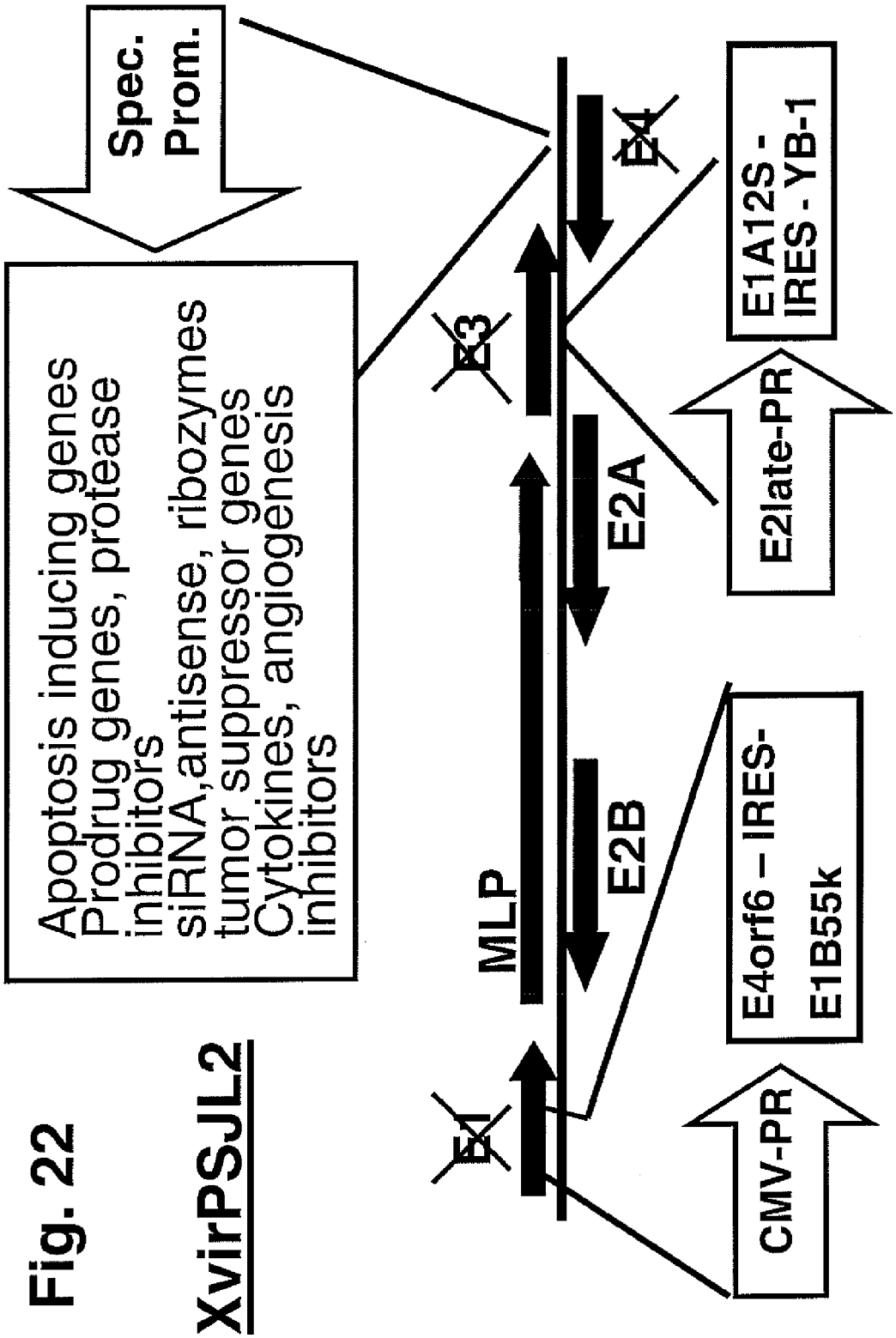
Figure 23:
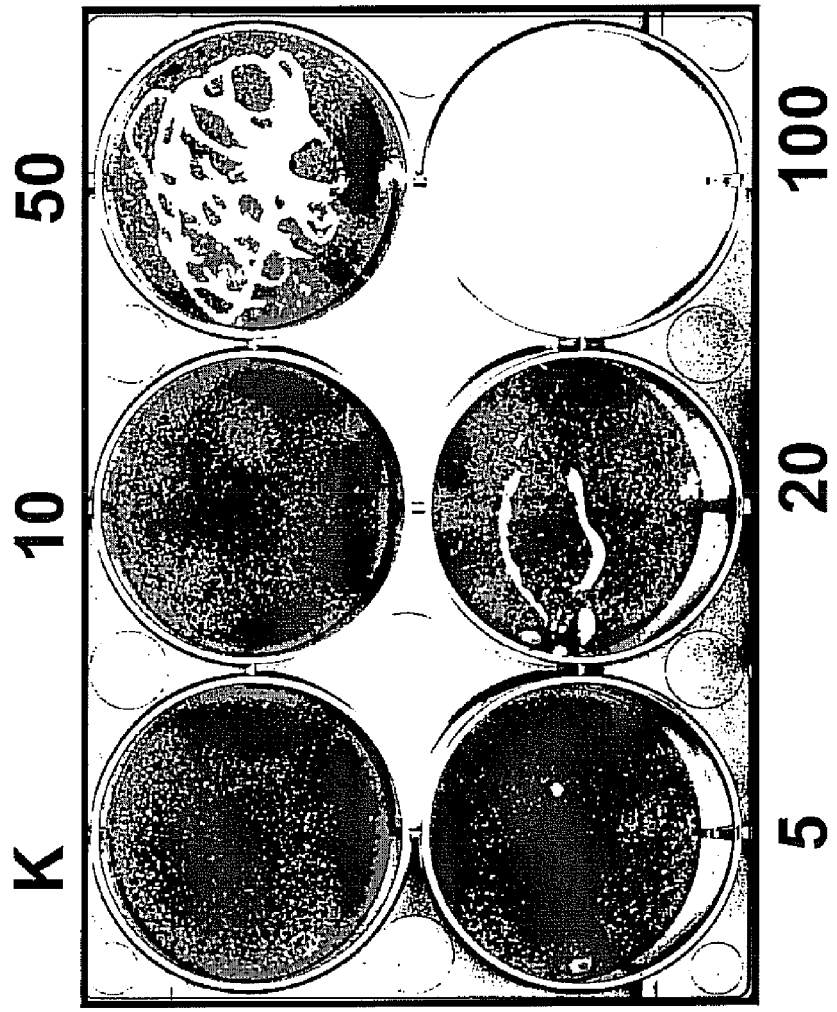
Figure 24:
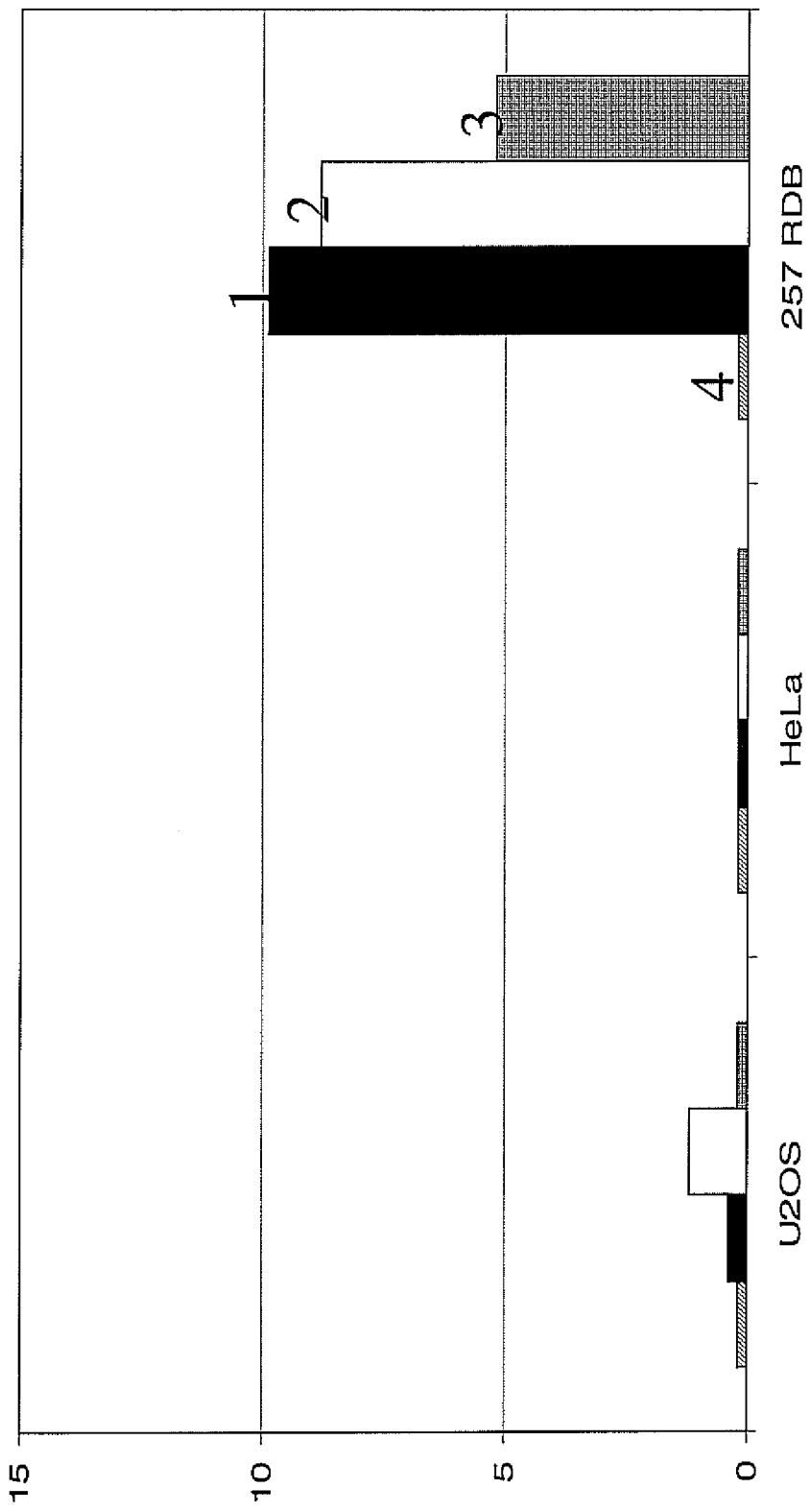
Figure 25:
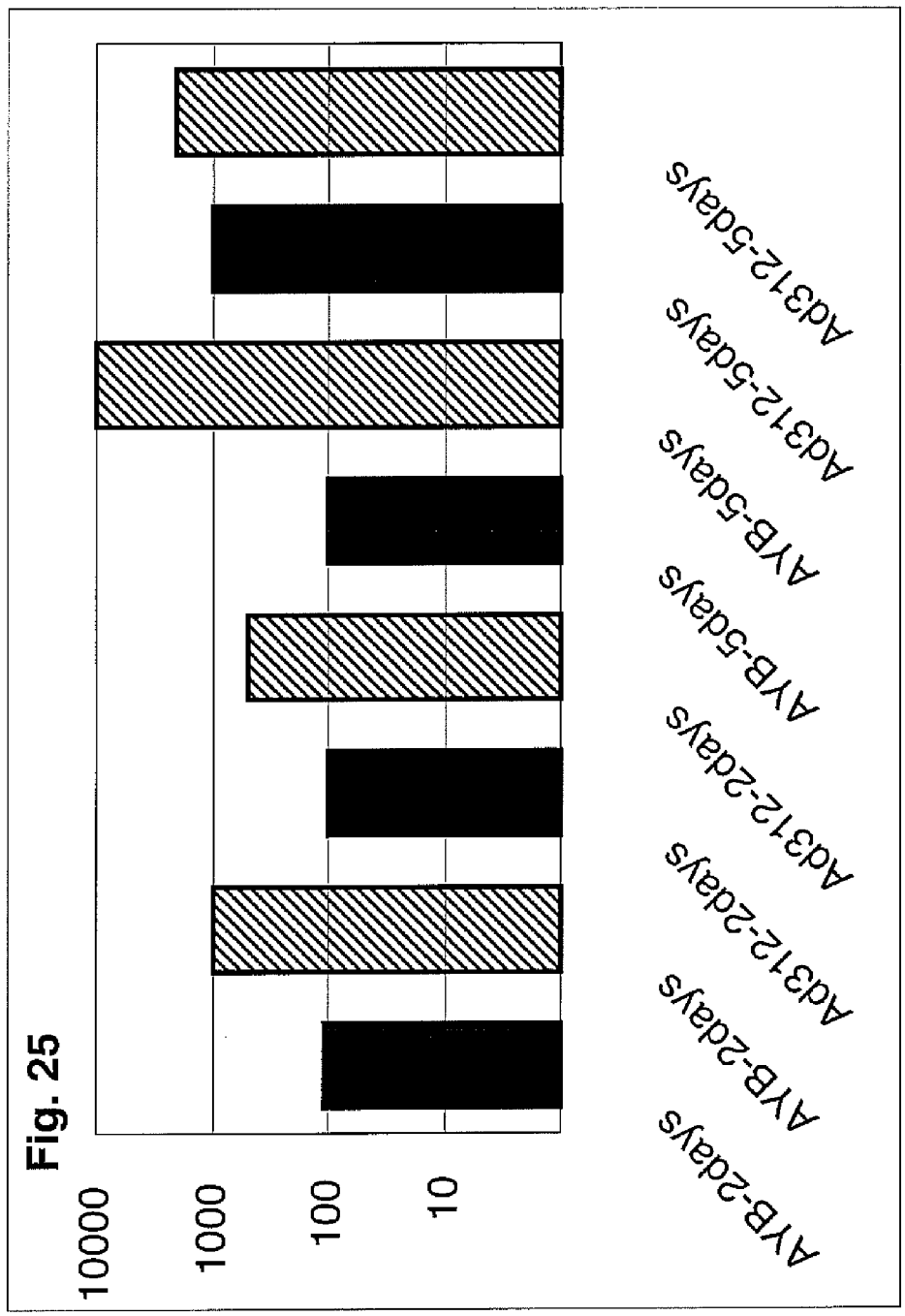
Figure 26:
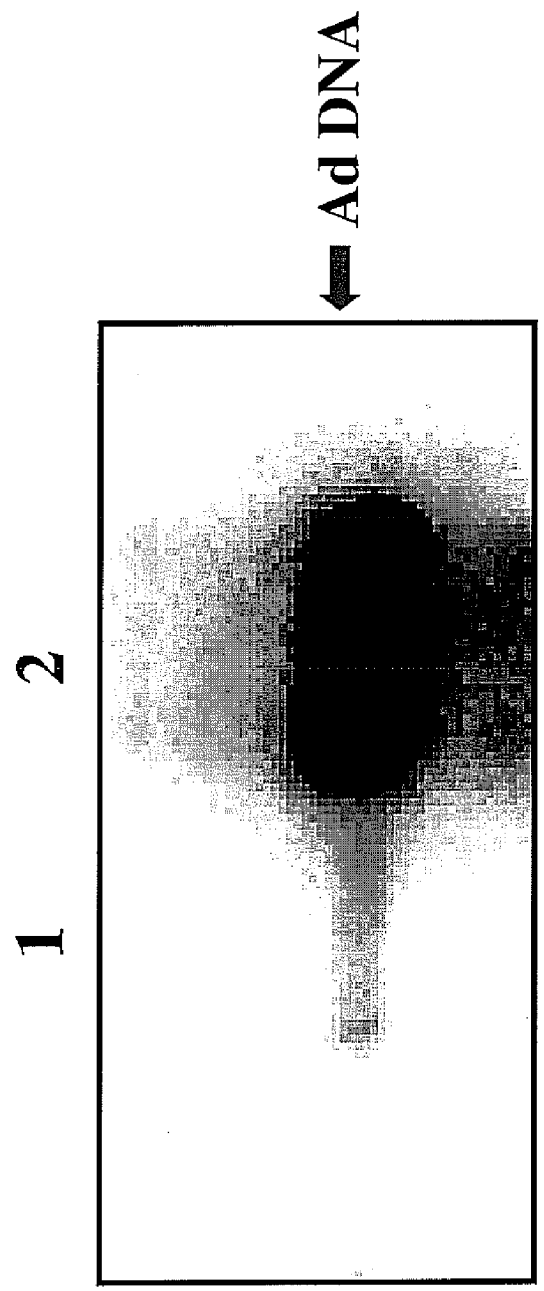
Figure 27:
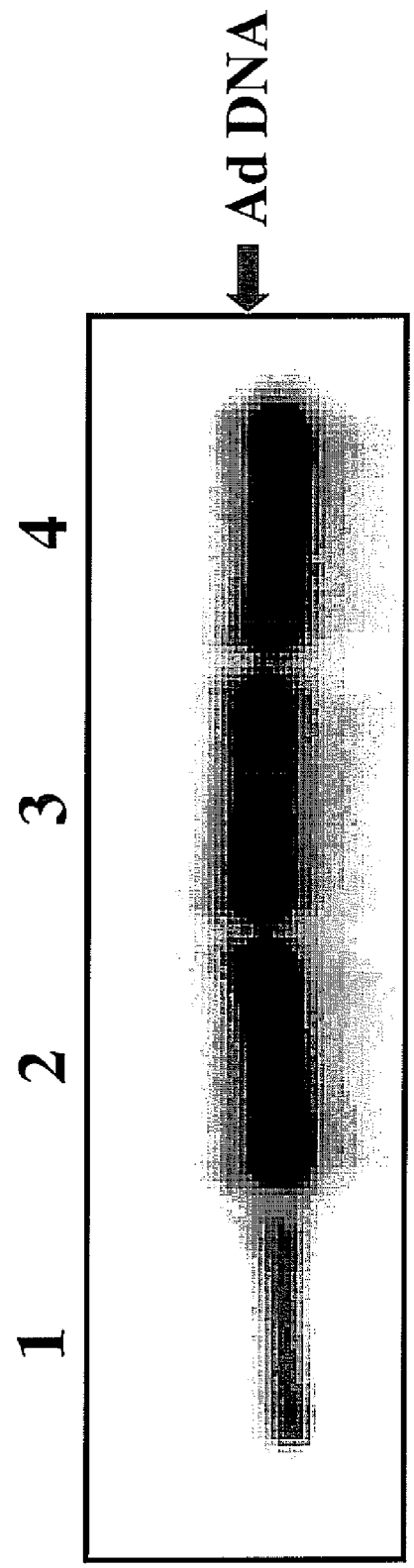
Figure 28:
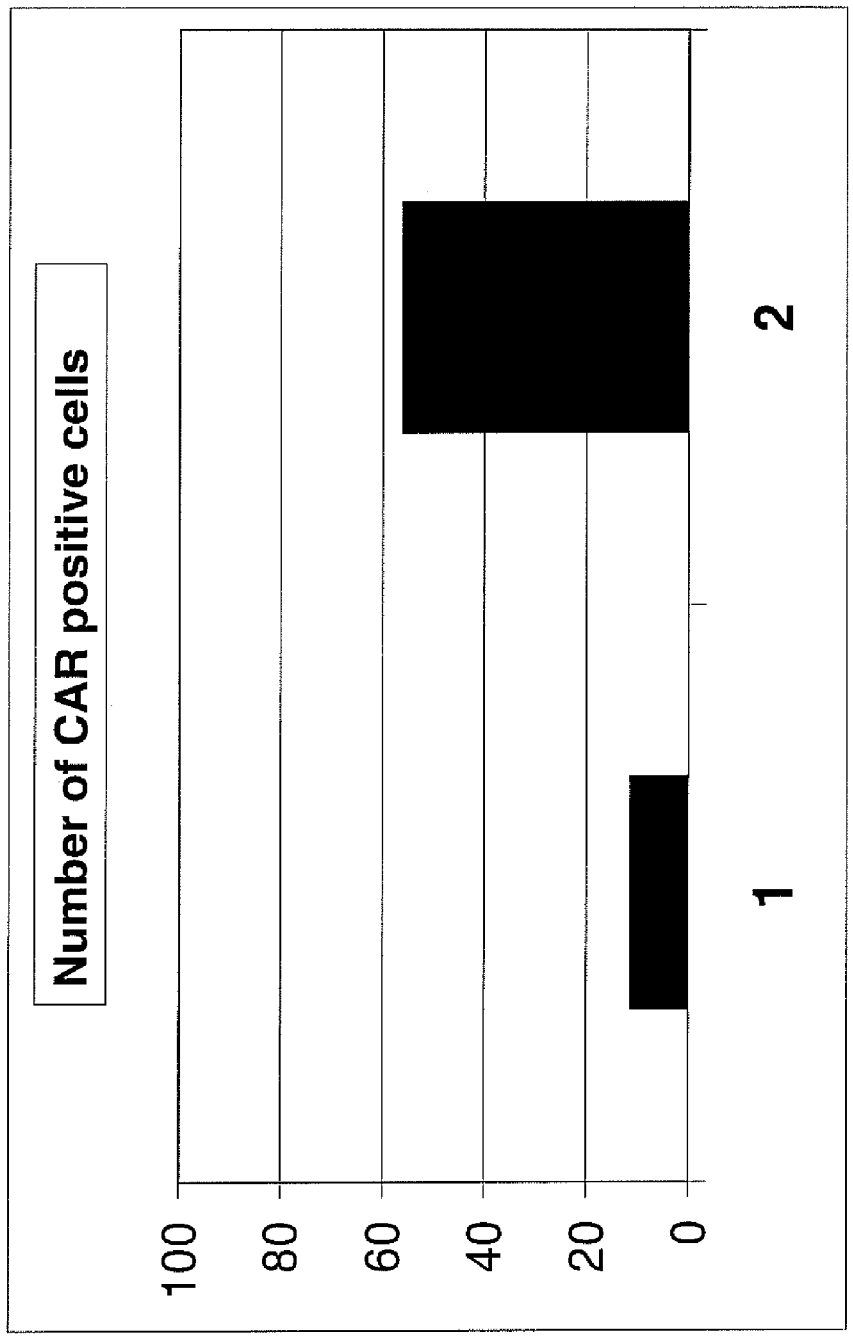
Figure 29:
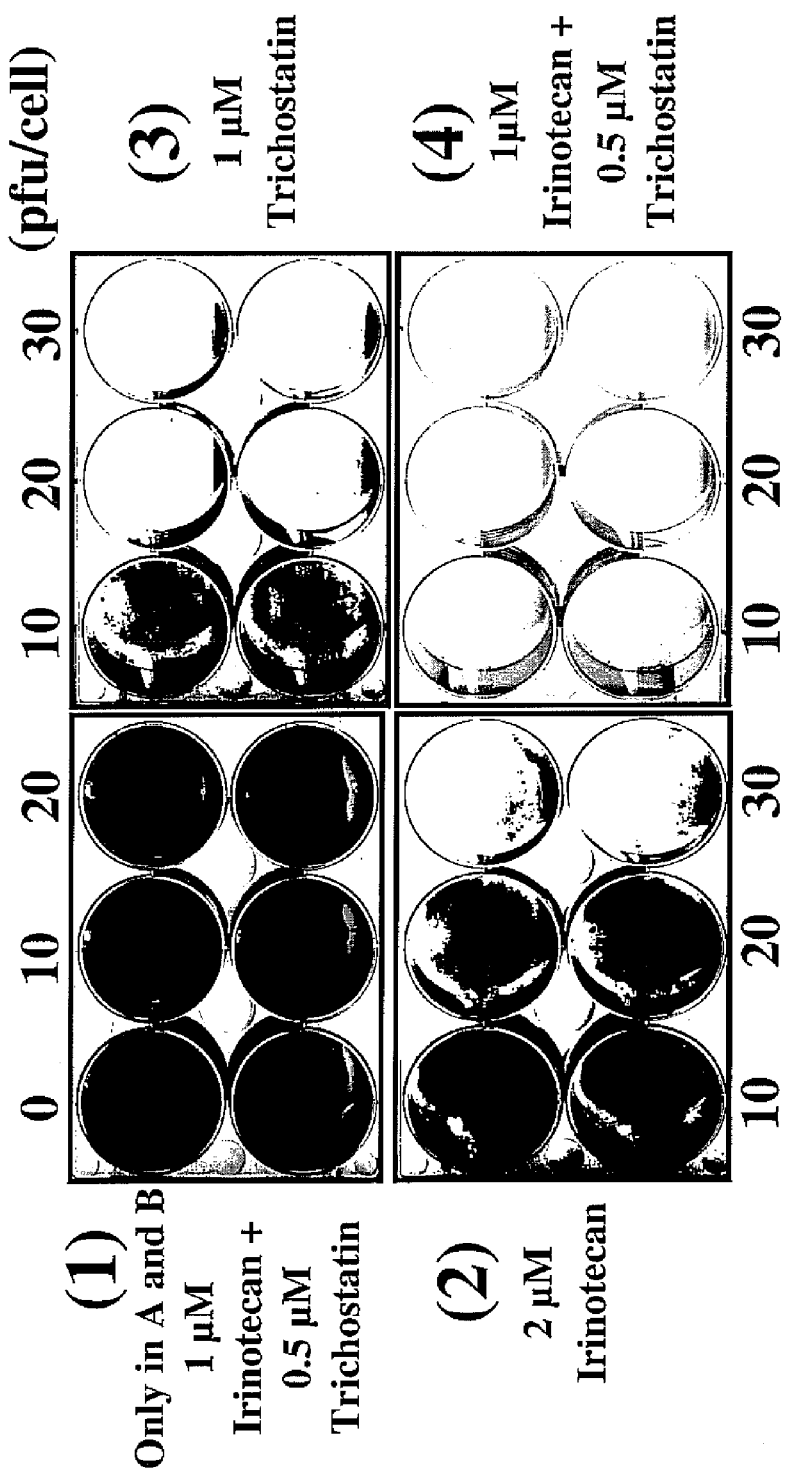
Figure 30:
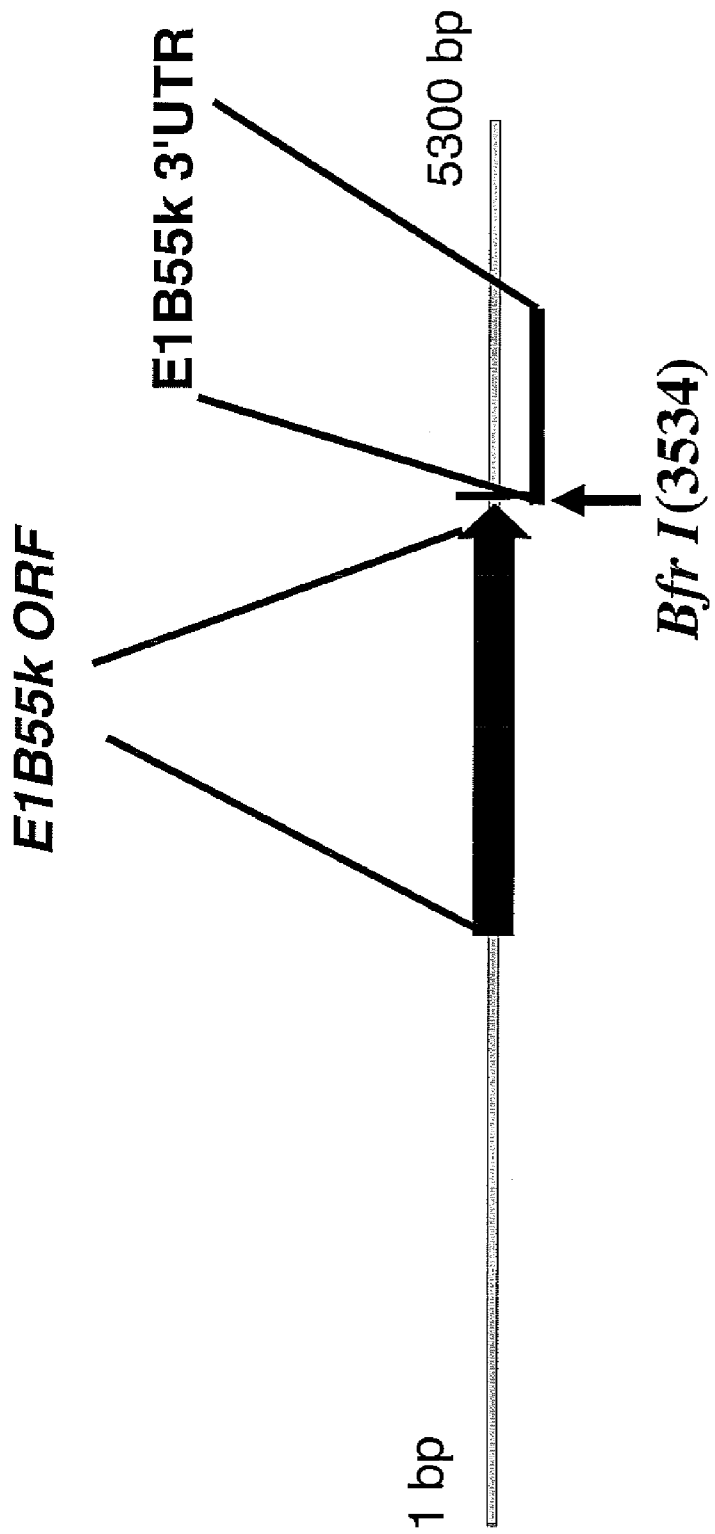
Figure 32:
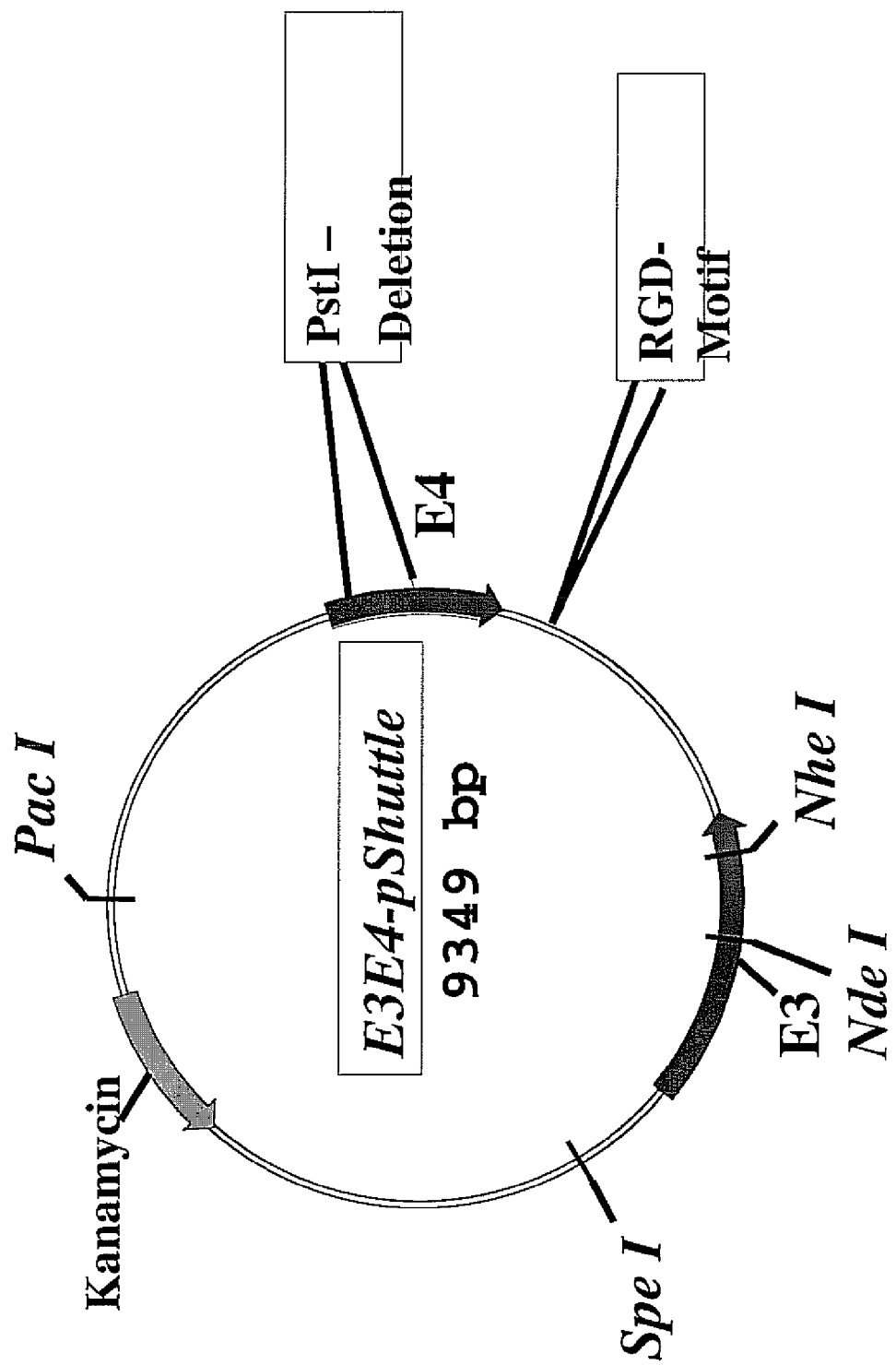

FIG. 18A/B shows wells having grown 18RDB cells (FIG. 18A) and 272RDB cells (FIG. 18B) after crystal violet staining and infection with Ad312 (20 pfu/cell), Xvir03 (5 pfu/cell) and control (non-infected), whereby crystal violet staining was performed five days after infection;

FIG. 19 shows the result of a Northern blot analysis of the expression of the E2 gene in A549 cells and U2OS cells after infection with wildtype adenovirus Ad5 and adenovirus Ad312;

FIG. 20 shows the result of a Northern blot analysis of the expression of the E2 gene in U2OS cells after infection with wildtype adenovirus and adenovirus delta24 after 12 and 24 hours;

FIG. 21 shows the structural design of the adenoviral vector XvirPSJL1;

FIG. 22 shows the structural design of the adenoviral vector XvirPSJL2;

FIG. 23 shows wells with HeLa cells grown therein after crystal violet staining and infection with adenovirus dl520 using different pfu/cells;

FIG. 24 shows a bar graph indicating the activity of luciferase in U2OS cells, HeLa cells and 257RDB cells upon usage of different promoter fragments of the adenoviral E2-late promoter;

FIG. 25 shows a bar graph indicating the number of viral particles after infection of U2OS cells with a YB-1 expressing adenovirus and virus Ad312 after two and five days, whereby a distinction is made between intracellularly remaining viral particles (represented in black) and released extracellular viral particles (horizontally striped);

FIG. 26 shows the result of a Southern Blot analysis of the replication behaviour of Adenovirus dl 520 in U373 cells with and without treatment of the cells with irinotecan;

FIG. 27 shows the result of a Southern Blot analysis of the replication behaviour of adenovirus dl 520 in U 373 cells with and without treatment of the cells with trichostatin A;

FIG. 28 shows the result of a FACS analysis of U 373 cells treated with trichostatin for the expression of Coxsackievirus-Adenovirus receptor (CAR), expressed as percentage of CAR-positive cells;

FIG. 29 shows four different panels of cell layer for the illustration of the effect of replicating adenovirus dl520 and irinotecan and trichostatin in different combinations;

FIG. 30 shows a schematic representation of the ORF of E1B55K with the 3'UTR fragment and the restriction site BfrI at position 3532;

FIG. 31 shows the sequence of the E1B55k-3'UTR region corresponding sequence position 3507 to 4107 of wildtype Ad5 (SEQ. ID.NO. 8); and FIG. 32 shows a schematic representation of a universal shuttle plasmid for the generation of E3/E4 modified recombinant adenoviruses having the RGD motif.

EXAMPLE 1

Figure 1:
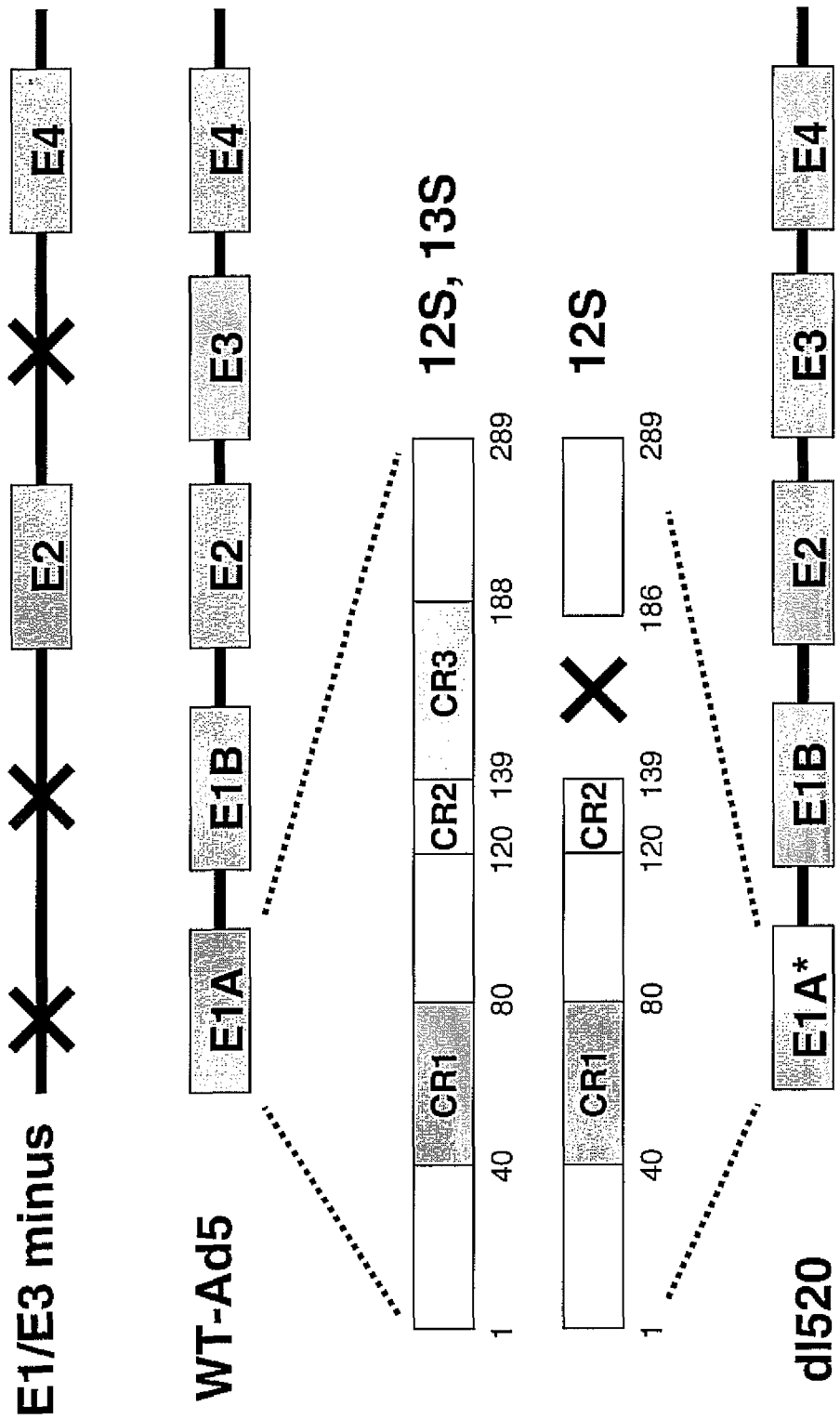

Types of E1A Modifications as May be Comprised by the Adenoviruses which are Used in Accordance with the Invention FIG. 1 shows the structural design of adenoviral vectors AdE1/E3-minus, i.e. E1/E3-deleted adenoviruses, wildtype adenovirus and adenovirus dl520.

Adenovirus AdE1/E3-minus does not have a region coding for a functional E1A or a functional E1B or E3 and is used in the present experiments as a control for toxicity.

Wildtype E1A gene codes for a total of 5 proteins which are generated through alternative splicing of the E1A RNA. Among others, two different proteins are generated, namely a 289 amino acid protein and a 243 amino acid protein. dl520 does not code for the 289 amino acid protein as it has a deletion in the CR3 stretch of the E1A gene which results in the lack of the 13S gene product. The adenovirus dl520 which may be used in accordance with the invention is referred to as 12S-E1A virus by those skilled in the art. Adenovirus dl347 (Wong and Ziff, J. Virol., 68, 4910-4920, 1994) known in the prior art is also a 12S-E1A virus which can be used in accordance with the present invention.

Within the 289 amino acid protein which is encoded by the 13S-E1A mRNA, there are 3 regions which are conserved among various adenoviral subtypes. These are referred to as CR1, CR2 and CR3. While CR1 and CR2 are present in both E1A proteins (E1A 12S and E1A 13S), i.e. in both the 289 amino acid and the 243 amino acid protein, the CR3 region is only present in the bigger one of the two aforementioned proteins.

The CR3 region is required for the activation of viral genes, in particular of E1B, E2, E3 and E4. Viruses which only comprise the smaller, i.e. 243 amino acid protein are only very weakly transactivating the viral genes and do not promote adenoviral replication in those cells which do not have YB-1 in the nucleus. As YB-1 is present in the nucleus only in tumor cells and can be detected only there, this vector is suitable to induce tumor-specific replication.

Due to the deletion of CR3 in dl520 this adenovirus cannot translocate cellular YB-1 into the cell's nucleus which is also referred to herein as translocation, and is thus not in a position to replicate in cells which are YB-1 nucleus-negative and is thus a virus which can be used in accordance with the present invention, whereby this virus comprises the transactivation required in accordance with the present invention.

EXAMPLE 2

Mode of Action of Adenoviruses in Depending on the Rb Status of Cells

Figure 2:
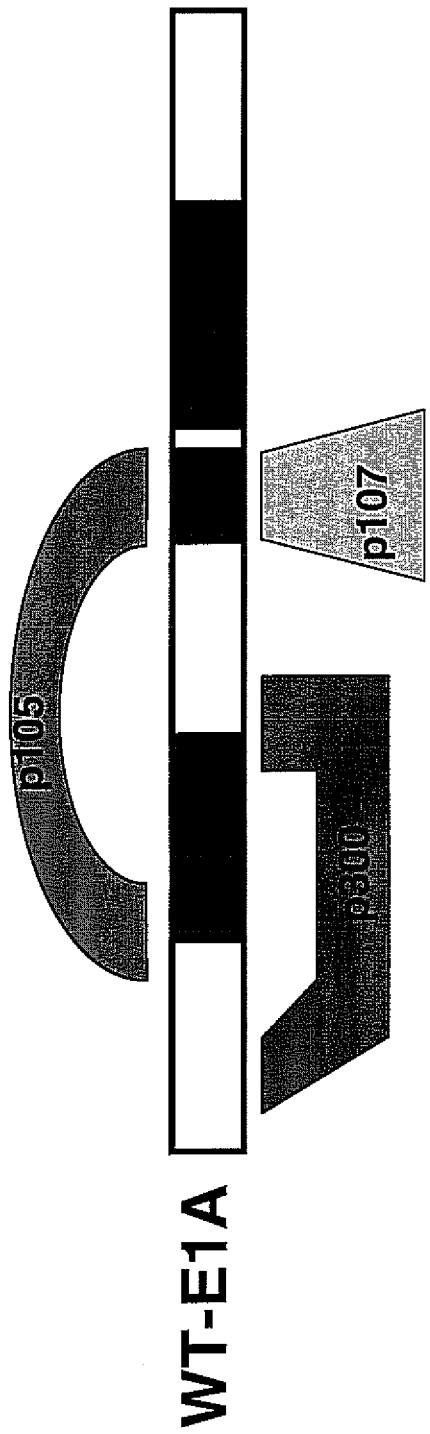
FIG. 2 shows the binding domains of the E1A proteins with respect to the binding of p300, p107 and p105.

FIG. 2 shows the binding domains of the E1A protein with regard to the binding of p300, p107 and p105. P300, as well as p107, is a cellular binding protein. The binding of the retinoblastoma protein (pRb), a tumor suppressor protein, is mediated through CR1 and CR2. Studies have shown that pRb and p107/p300 are in combination with the cellular transcription factor E2F effective in regulating transcription. The wildtype E1A protein interferes with the binding of E2F to Rb. The thus released E2F binds to the E2 early promoter and induces adenoviral replication thereby.

It is known from the prior art that certain deletions in the E1A oncoprotein may result in recombinant adenoviral vectors such as those mentioned in the following, which are capable of replicating predominantly in Rb-negative cells and can be used in accordance with the present invention. For example, the adenoviral vector dl922-947 comprises a deletion in the CR2 region (amino acid positions 122-129) and the vector CB016 has deletions in the CR1 region (amino acid positions 27-80) and CR2 region (amino acid positions 122-129). The vector E1Ad/01/07 comprises a deletion in the CR2 region (amino acid positions 111-123). Additionally, because of an additional deletion at the N-terminus (amino acid positions 4-25), additionally, there is no binding to protein p300. The adenoviral vector AdΔ24 comprises a deletion in the CR2 region (amino acid positions 120-127). The adenoviral vector described in patent EP 0 931 830 comprises deletions in the CR1 region and CR2 region.

The binding mechanism of E2F/RB and the release of E2F mediated through E1A is fundamentally different from the mechanism underlying the present invention. Unlike assumed in the prior art it is not the release of E2F from the Rb protein which is essential, not to say critical for viral replication, but it is the nuclear localisation of the human transcription factor YB-1. This transcription factor is, in normal cells, only present in the cytoplasm over most of the cell cycle. After infection with an adenovirus it is induced into the nucleus under certain circumstances or is already present in the nucleus in distinct cellular systems, such as distinct tumor diseases including, for example, but not limited thereto, breast cancer, ovary carcinoma, prostate carcinoma, osteosarcoma, glioblastoma, melanoma, small cell lung carcinoma and colorectal carcinoma.

EXAMPLE 3

Figure 3:
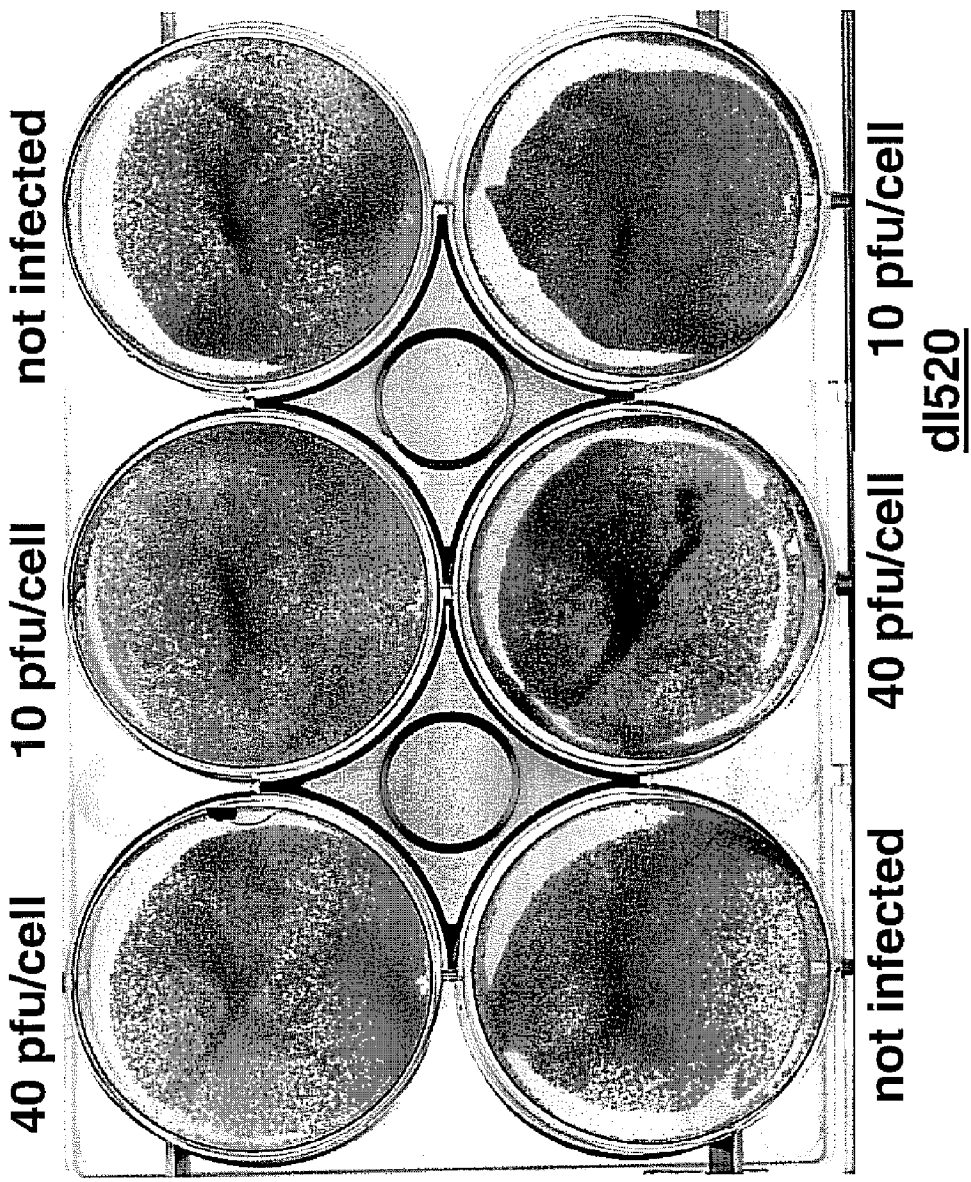
FIG. 3 shows U2OS cells which do not have YB-1 in the nucleus, after infection with the E1/E3-deleted adenovirus Ad5 referred to therein as E1/E3-minus Ad5, and dl520.

Infection of U2OS Cells 100,000 U2OS cells were plated per well. On the next day the cells were infected with the various adenoviruses as depicted in FIG. 3. The infection was performed in 500 µl serum free DMEM medium at 37° C. for 1 h. Subsequently, the infection medium was removed and replaced by 2 ml complete medium (10% FCS/DMEM). The analysis was performed after 3 days using crystal violet staining.

As may be taken from FIG. 3, the U2OS cells which do not have YB-1 in the nucleus, show no lysis as illustrated by crystal violet staining after infection with two different adenoviruses, namely the E1/E3-deleted adenovirus referred to as E1/E3-minus, and adenovirus dl520, which can be used in accordance with the present invention. In connection therewith, first, the medium is removed. Subsequently, the cells are overlaid with crystal violet (50% ETOH, 3% formaldehyde, 5% acetic acid, 1% crystal violet) and incubated at room temperature for 5-10 min. Subsequently, the plates having 6 wells are thoroughly rinsed with water and dried at room temperature.

This confirms the finding underlying the present invention that the presence of YB-1 is required in order to induce the viruses used in accordance with the present invention, to lyse the infected cells.

EXAMPLE 4

Figure 4:
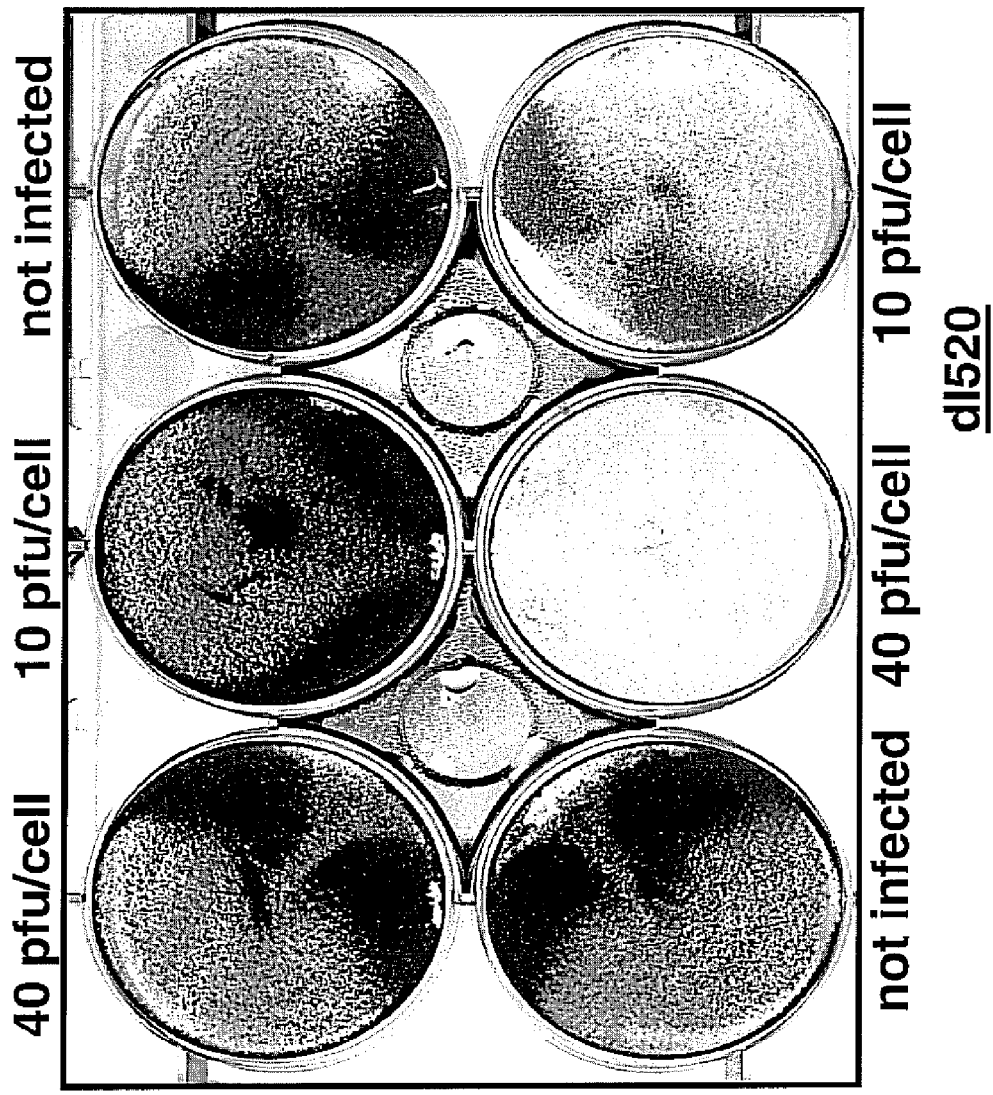
FIG. 4 shows 257RDB cells which contain YB-1 in the nucleus, after infection with the E1/E3-deleted adenovirus Ad5 referred to therein as E1/E3-minus Ad5, and adenovirus dl520.

Infection of 257RDB Cells 100,000 257RDB cells were plated per well. On the next day the cells were infected with the various adenoviruses as depicted in FIG. 4. The infection was performed in 500 µl serum free DMEM medium for 1 h at 37° C. Subsequently, the infection medium was removed and replaced by 2 ml complete medium (10% FCS/DMEM). The analysis was performed after three days using crystal violet staining.

The result of this experiment is depicted in FIG. 4. The adenovirus referred to as E1/E3-minus Ad5 which is E1/E3-deleted, did not show any lysis at low MOIs (pfu/cell) upon infection of 257RDB cells which have YB-1 in the nucleus. In contrast thereto, dl520 which, as shown in example 3, does not replicate in YB-1 nucleus-negative cells and at the same time codes with E1A for a transactivating oncogene protein in accordance with the present invention, results in a factually complete lysis at an MOI (multiplicity of infection) of 40 pfu per cell and a still predominant lysis at an MOI of 10 pfu per cell. It can be concluded therefrom that dl520 and similar viruses such as described herein by dl1119/1131 or AdXvir 03, require an MOI which is reduced by about 1 magnitude (factor of ten) compared to E1-deleted or an E1/E3-deleted adenovirus which justifies their clinical use.

As depicted in FIG. 7, the protein E1A of dl520 is characterised in that the CR3 region thereof is deleted which results in the transactivation required for the use in accordance with the present invention and replication in YB-1 nucleus-positive cells.

EXAMPLE 5

Infection of 257RDB and U2OS Cells with dl1119/1131

Figure 5:
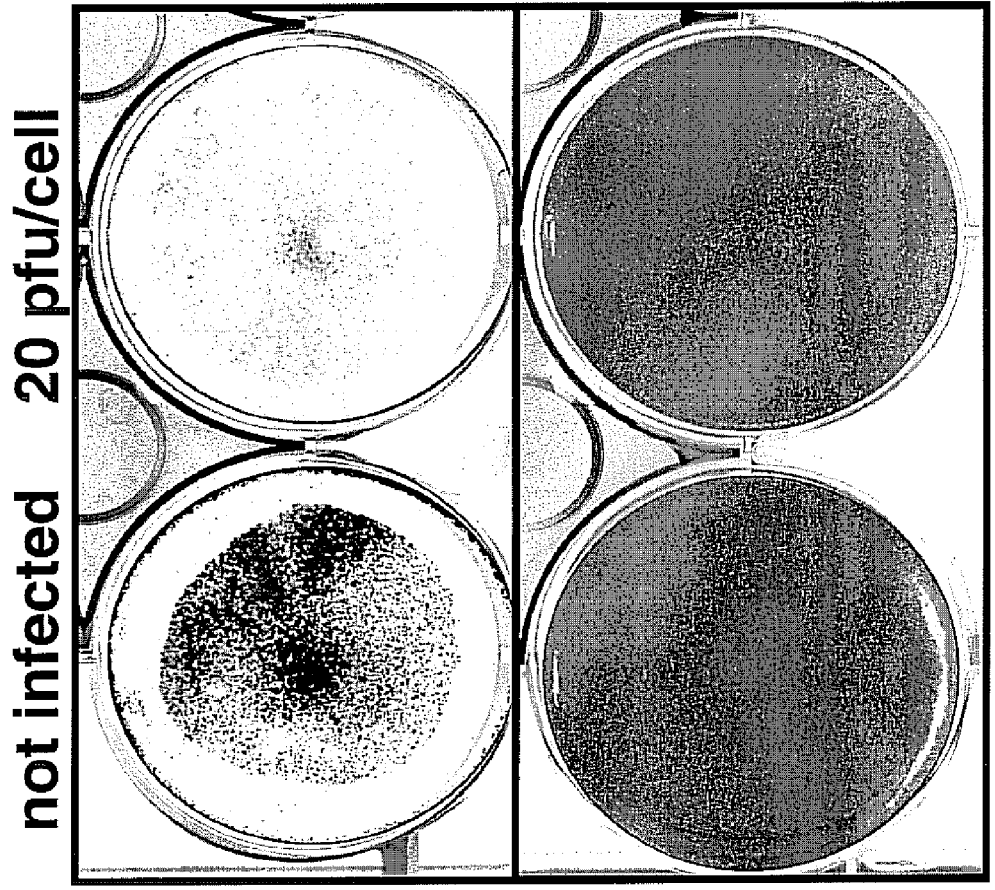
FIG. 5 shows 257RDB cells and U2OS cells after infection with adenovirus dl1119/1131.

As depicted in FIG. 5, there is no lysis at an MOI of 20 pfu per cell upon infection of YB-1 nucleus-negative U2OS cells with adenovirus dl1119/1131 which exhibits a deletion of amino acids 4-138 of the E1A protein and the nucleic acid coding therefor, and further comprises a stop codon after amino acid 218, whereby the expressed truncated E1A protein comprises the CR3 region of the complete E1A protein. As a negative control a non-infected cell layer was used.

In contrast thereto, there was factually a complete lysis of the cell layer at an MOI of 20 pfu per cell under the influence of adenovirus dl1119/1131 in a cellular system such as 257RDB which contains YB-1 in the nucleus, i.e. is YB-1 nucleus-positive. Insofar this example is another proof that a modified E1A oncogene protein which, as depicted in FIG. 7, comprises, for example, only the CR3 region and which is lacking the CR1 region and CR2 region, provides for the required transactivation in YB-1 nucleus-positive cells which is required for the replication of adenoviruses in accordance with the present invention, which results in viral replication. The adenovirus dl1119/1131 is thus a further adenovirus which can be used in accordance with the present invention. It is within the present invention that also viruses can be used which are designed similar to dl1119/1131 with regard to the CR3 region, but, in contrast thereto, have the CR1 region and/or CR2 region.

EXAMPLE 6

Detection of Nuclear YB-1 in Multidrug Resistant Cells

The example is based on the consideration that nuclear YB-1 should bind as a transcription factor to the Y-box (CAAT sequence) within the mdr1 promoter (engl. multiple drug resistance promoter). In order to detect this, a so-called EMSA analysis (electrophoretic mobility shift assay) was performed. In connection therewith, nuclear protein is isolated and subsequently 1-10 µg protein is incubated together with a short DNA fragment (oligo) at 37° C. In order to determine nuclear YB-1, the following oligonucleotide was used: mdr1 promoter in contrast to U2O3 (Position-86 to -67): TGAGGCTGATTGGCTGGGCA (SEQ. ID. NO. 9) (the X-box is underlined).

This DNA fragment is radioactively labelled at the 5' end with $^{32}$P prior to that. Subsequently, separation is performed in a native polyacryl amide gel. In case the protein YB-1 is binding to a sequence in the oligonucleotide, this can be detected as any non-bound oligonucleotide is migrating faster in the gel than bound oligonucleotide (Holm, P. S. et al., JBC 277, 10427-10434, 2002; Bargou, R. C. et al., Nature Medicine 3, 447-450, 1997).

Figure 6:
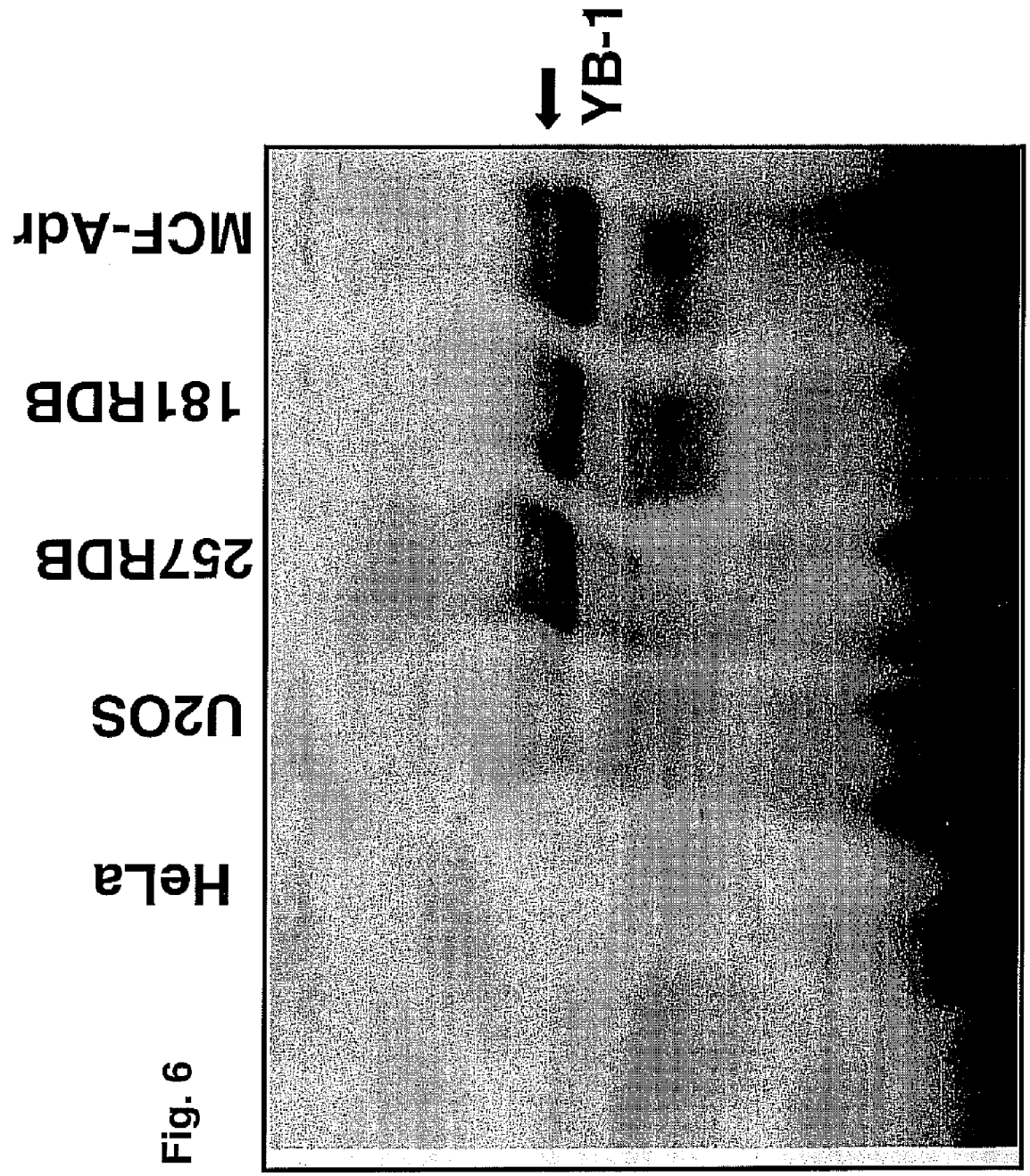
FIG. 6 shows the result of an EMSA analysis which confirms that YB-1 is present in the cellular nucleus in multi-resistant cells and in cell lines 257RDB, 181 RDB, MCF-7Ad, whereas YB-1 is not present in the nucleus of US2OS and HeLa cells.

As depicted in FIG. 6, it could be shown with the EMSA analysis that YB-1 is present in the nucleus of multidrug resistant cells 257RDB, 181RDB and MCF-7Ad cells in contrast to cell lines U2OS and HeLa cells.

The results shown in example 4 and 5 confirm that the adenoviruses dl520 and dl1119/1131 replicate in YB-1 nucleus-positive cells such as, e.g., 257RDB in contrast to U2O5, and induce lysis thereof. This confirms the finding about the use of the adenoviruses in accordance with the present invention. Additionally, the results confirm that already a, compared to wildtype adenovirus, weak transactivation of viral genes in YB-1 nucleus-positive cells through modified or deleted E1A gene products results in successful replication and lysis of such cells in the presence of YB-1 in the nucleus, including, for example, multidrug resistant cells and that the adenoviruses as described herein, can thus be used in the lysis of such tumors.

EXAMPLE 7

Increase of Replication Efficiency of E1-Minus Adenoviruses

This example shows that the early viral genes E1B-55K and E4orf6 can be substituted through transfection with the plasmid pE4orf6 and infection with the E1/E3-deleted adenovirus Ad-55K. Ad-55K is an E1/E3 deleted virus, whereby E1B-55K is cloned into E1 and is under the control of CMV. This substitution is necessary with regard to the fact that AdYB-1, i.e. an adenovirus which expresses YB-1, does not express these early genes and that the present inventor has recognised that a substitution of these early genes in a replication system which contains YB-1 in the nucleus, is capable of increasing replication efficiency and particle formation efficiency, respectively, to an extent comparable to the one of wildtype adenoviruses of type Ad5.

The following was done:

Transfection of each $10^5$ U2OS cells with the plasmid pE4orf6 using lipofectamine. The plasmid pE4orf6 carries the DNA sequence coding for the early viral gene E4orf6 under the control of CMV.

24 h after transfection with the plasmid pE4orf6 the cells were infected with the YB-1 expressing E1/E3-deleted adenovirus AdYB-1 (50 pfu/cell) and the E1/E3-deleted E1B-55K adenovirus Ad-55K (50 pfu/cell). Ad-55K is an E1/E3-deleted virus which carries as transgene the viral gene E1B-55K under CMV control.

Subsequently, the cells were removed from the medium (2 ml) 5 days after infection (=post infectionem). The release of the viral particles from the isolated cells was done by alternating freezing and thawing for three times (thaw/freeze).

Figure 8:
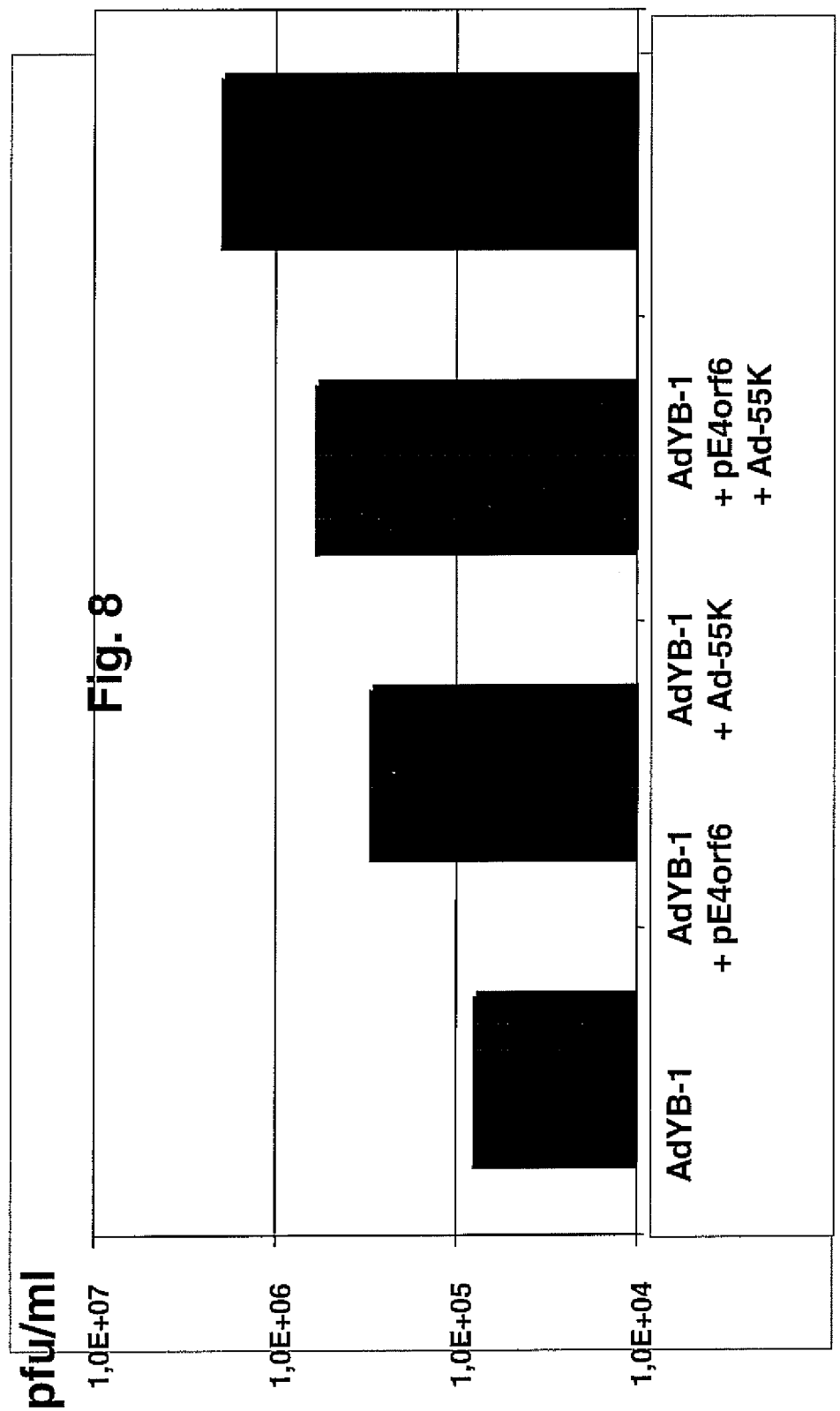
FIG. 8 shows a bar graph indicating replication efficiency of adenovirus in the presence of additionally expressed viral proteins in absolute figures.
Figure 9:
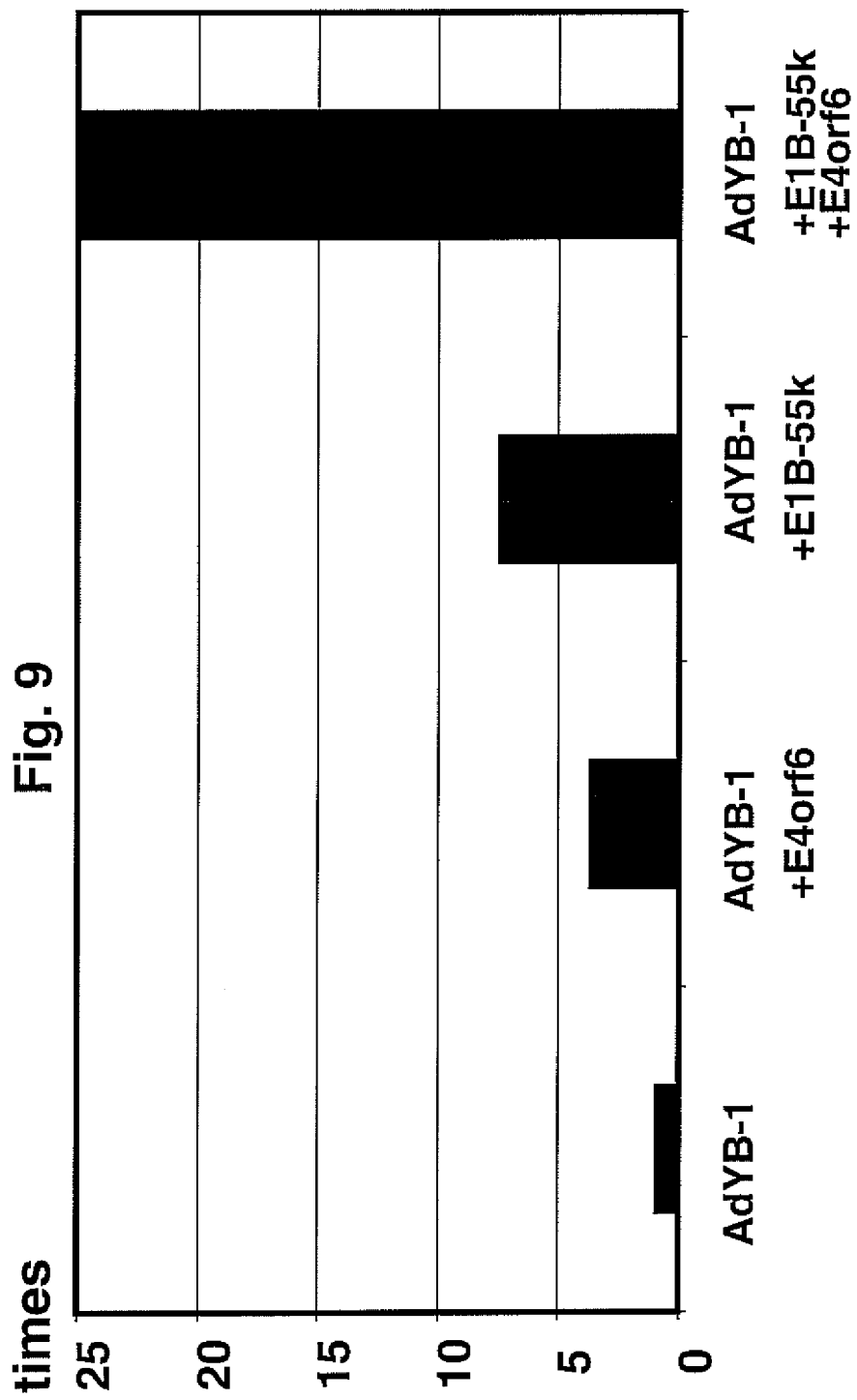
FIG. 9 shows a bar graph indicating the increase in replication efficiency of adenoviruses in the presence of additionally expressed viral proteins.

Subsequently, a plaque assay was performed on 293 cells for determining the generated infectious particles (plaque forming units per ml (pfu/ml)). The result is depicted in FIGS. 8 and 9. FIG. 8 shows the result of the plaque assay, represented in absolute figures. The most significant difference compared to infection with AdYB-1 alone is shown by transfection with the plasmid pE4orf6 and co-infection with the two viruses AdYB-1 and Ad-55K. FIG. 9 shows the result of FIG. 8, whereby the increase of the replication efficiency is represented as multifold of the replication determined for AdYB-1. The cells infected with plasmid pE4orf6 and subsequently with AdYB-1 and E1B-55K (Ad-55K) produced up to 25 times more pfu/ml.

Based on these results it can be concluded that the substitution of E1B-55K and E4orf6 increases the number of viruses formed (pfu/ml) after infection with the E1/E3-deleted adenovirus AdYB-1 by a factor of up to 25. The additive effects of E1B-55K and E4orf6 on the production of plaque forming units (pfu) is significantly higher compared to the effects of each of the two gene products.

Control experiments with one plasmid which expresses EGFP, clearly showed that in the experimental approach chosen only 10% of the cells were successfully transfected with plasmid pE4orf6. The number of the particles formed in the cells which express both E1B-55K and E4orf6 is comparable to the one of human adenovirus type 5 (wildtype). This confirms the finding underlying the present invention that the expression of E4orf6 and E1B-55K is, in combination with the nuclear localisation of YB-1, able to provide for adenoviral replication and particle formation, in particular of E1A-deleted adenoviruses, which is comparable to the one of wildtype Ad5.

EXAMPLE 8

Increased Replication of Adenoviruses which are not Replicating in YB-1 Nucleus-negative Cells, in YB-1 Nucleus-positive Cells Upon Administration of Cytostatics It is known in the prior art that the addition of different cytostatics induces nuclear localisation of the human transcription factor YB-1. As has been found by the present inventor, YB-1 localised in the nucleus controls adenoviral replication by means of activation of the adenoviral E2-late promoter. The combination of both effects can be used in order to provide for specific tumor lysis.

In the practising of the oncolytic assays the following procedure was followed: 200,000 cells (HeLa and U2OS, respectively) were plated into each well of a 6 well plate. On the next day 40 ng/ml (final concentration) of daunorubicine were added. After 3 hours of incubation the cells were infected with 10 and 30 pfu dl520/cell, respectively. Subsequently, the cells were incubated in cytostatic free medium. After 3-5 days the cells were stained using crystal violet.

Figure 10:
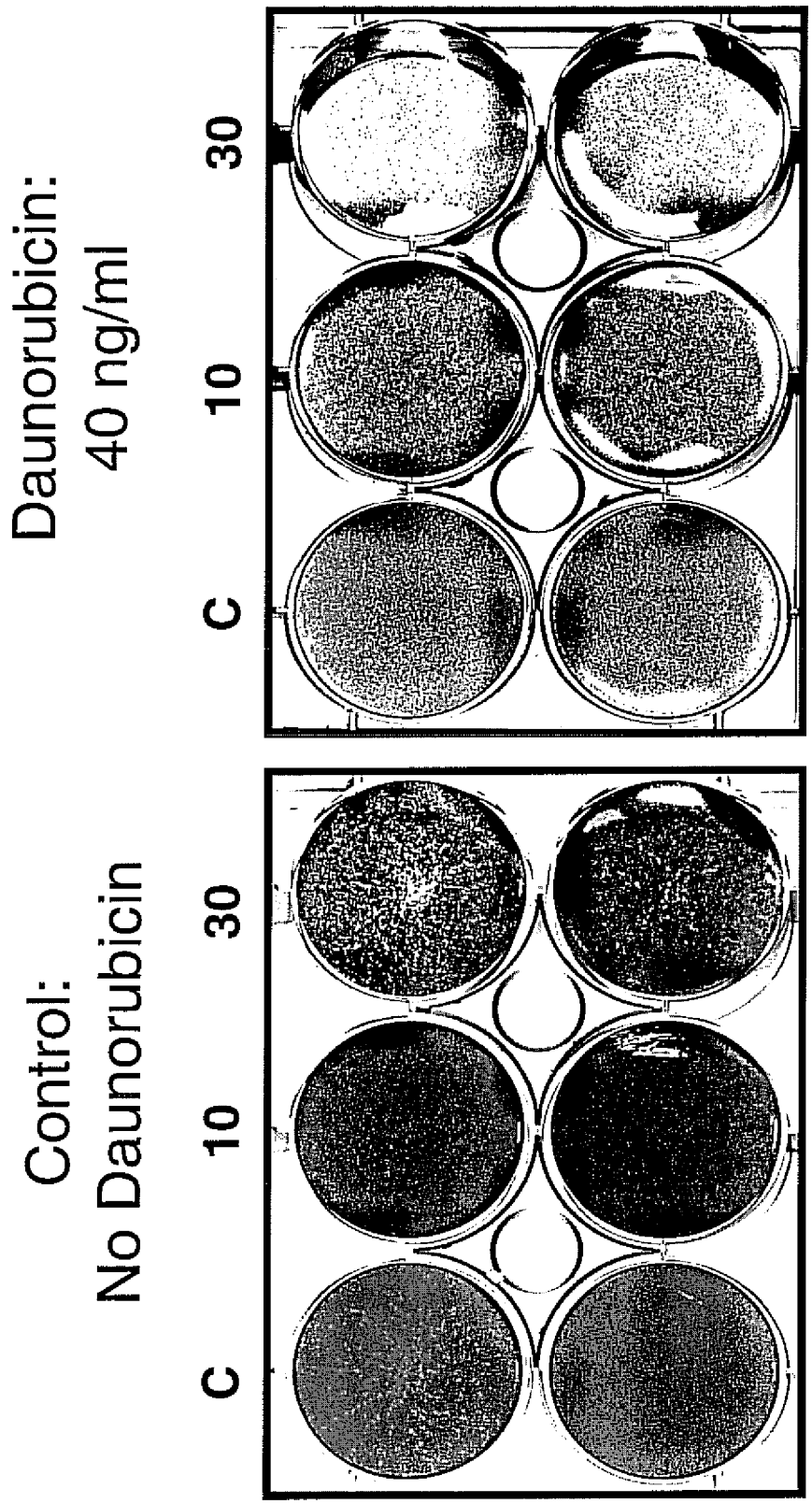
FIG. 10 shows wells with U2OS cells grown therein after crystal violet staining and infection with dl520 with 10 and 30 pfu/cell and control (K), respectively, without administration of daunorubicin and with administration of 40 ng daunorubicin per ml.
Figure 11:
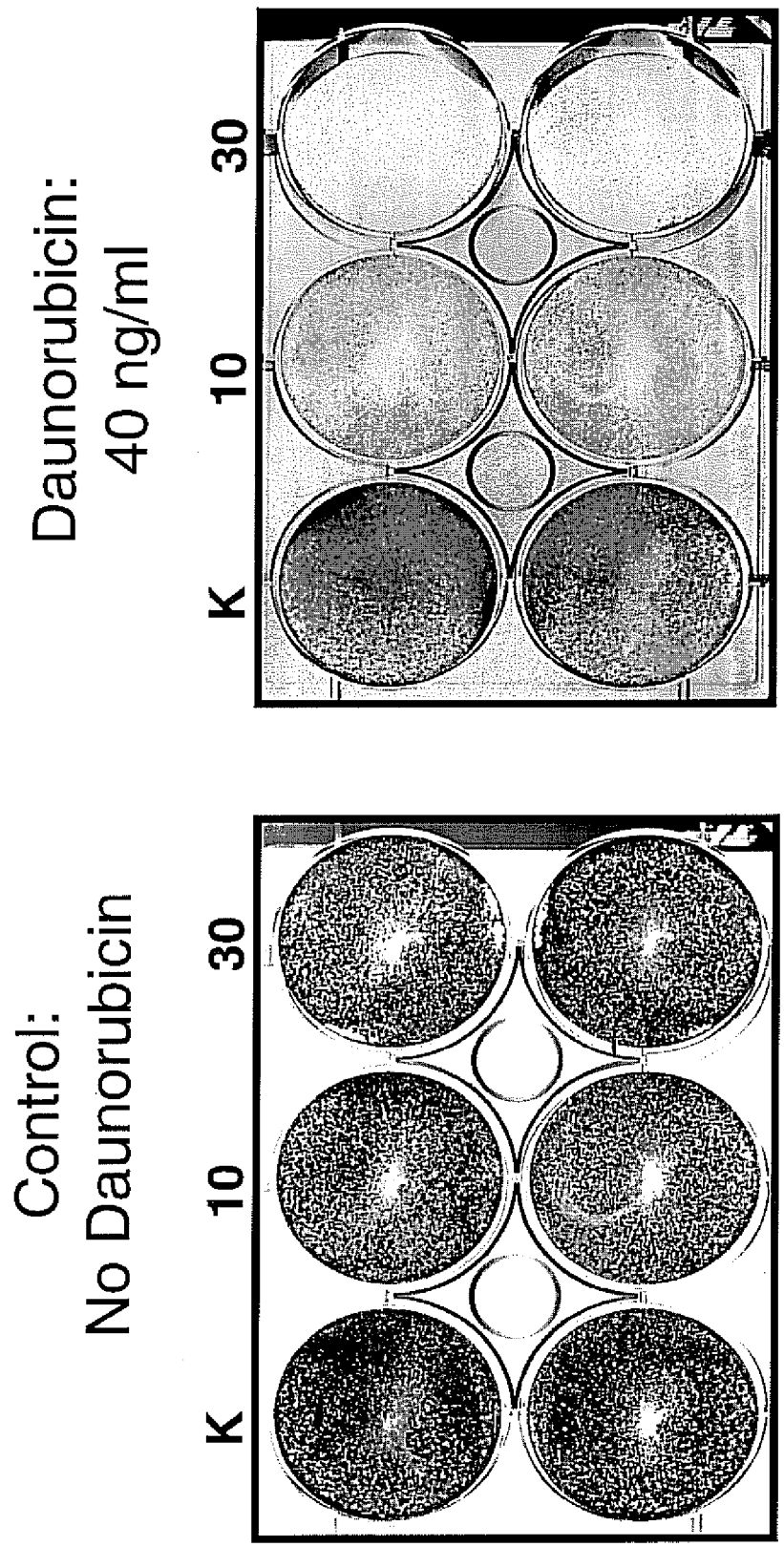
FIG. 11 shows wells having HeLa cells grown therein after crystal violet staining and infection with dl520 with 10 and 30 pfu/cell and control (K), respectively, without administration of daunorubicin and with administration of 40 ng daunorubicin per ml.

As may be taken from FIGS. 10 and 11, the addition of daunorubicine induces the replication of dl520 through nuclear localisation of YB-1. Thus, dl520 creates a bigger tumorlytic effect in combination with the cytostatic daunorubicine compared to daunorubicine alone.

EXAMPLE 9

In vivo Tumor Lysis by dl520

The HeLa (YB-1 nucleus-negative) and 257RDB (YB-1 nucleus-positive) cells used in this in vivo study, were expanded under sterile cell culture conditions. Prior to the injection of the cells into mice (strain CD1NuNu) in order to generate a subcutaneous tumor, the cells are harvested by trypsinisation, taken up in DMEM medium (10% FCS), counted and washed with PBS one time. Subsequently, the cells are centrifuged, the PBS aspired and the cells are portioned in fresh PBS with the desired cell number. The cell number which was subcutaneously injected in this study, was each $5\times10^6$ cells of both cell lines. The injection was performed subcutaneously into one flank of the animals, whereby HeLa cells were injected into the right side and 257RDB cells were injected into the left side for better distinction. The growth of the tumors was controlled twice a week and thereby the length and the width of the tumors was measured using vernier calipers. Based thereon, the tumor volume was calculated based on the following mathematical formula:

$$\frac{3}{4}\pi * a/2 * (b/2)^2 \quad a=\text{length}, b=\text{width}$$

Once the tumor has reached a volume of 200 to 520 mm³, the virus and PBS as negative control, respectively, were intratumorally applied. The volumes to be injected were identical and were 50 µl each time. This was repeated on 3 consecutive days. The overall dosage of applied viruses was $5\times10^8$ pfu. Subsequently, the tumor growth was continued to be documented twice a week and the volume was calculated. At the end of the study the mice were sacrificed and the tumors removed for further analysis.

Figure 12:
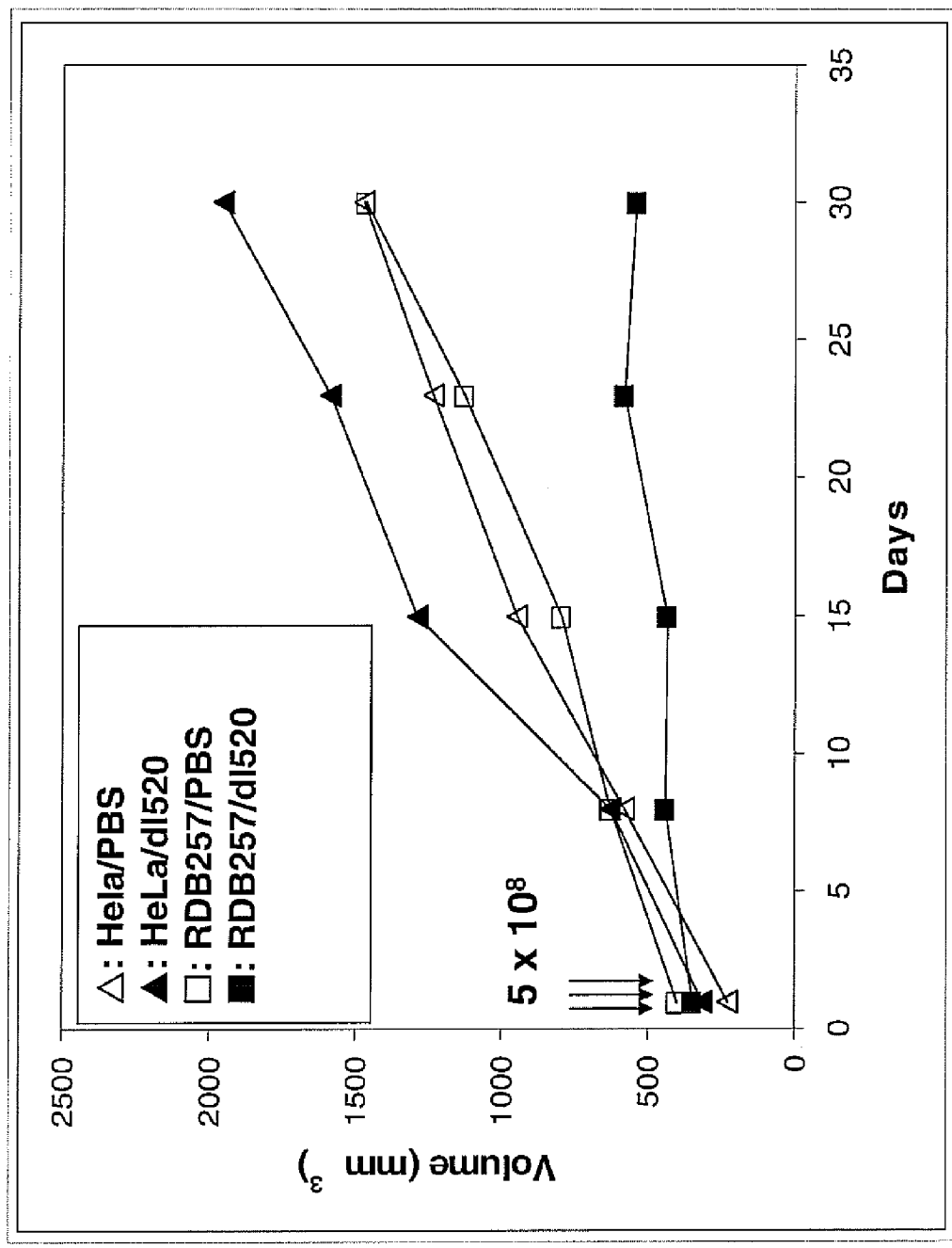
FIG. 12 shows a diagram of the tumor volume as a function of time of tumors of different origin (RDB257 and HeLa) after treatment with PBS and dl520, respectively.
Figure 13:
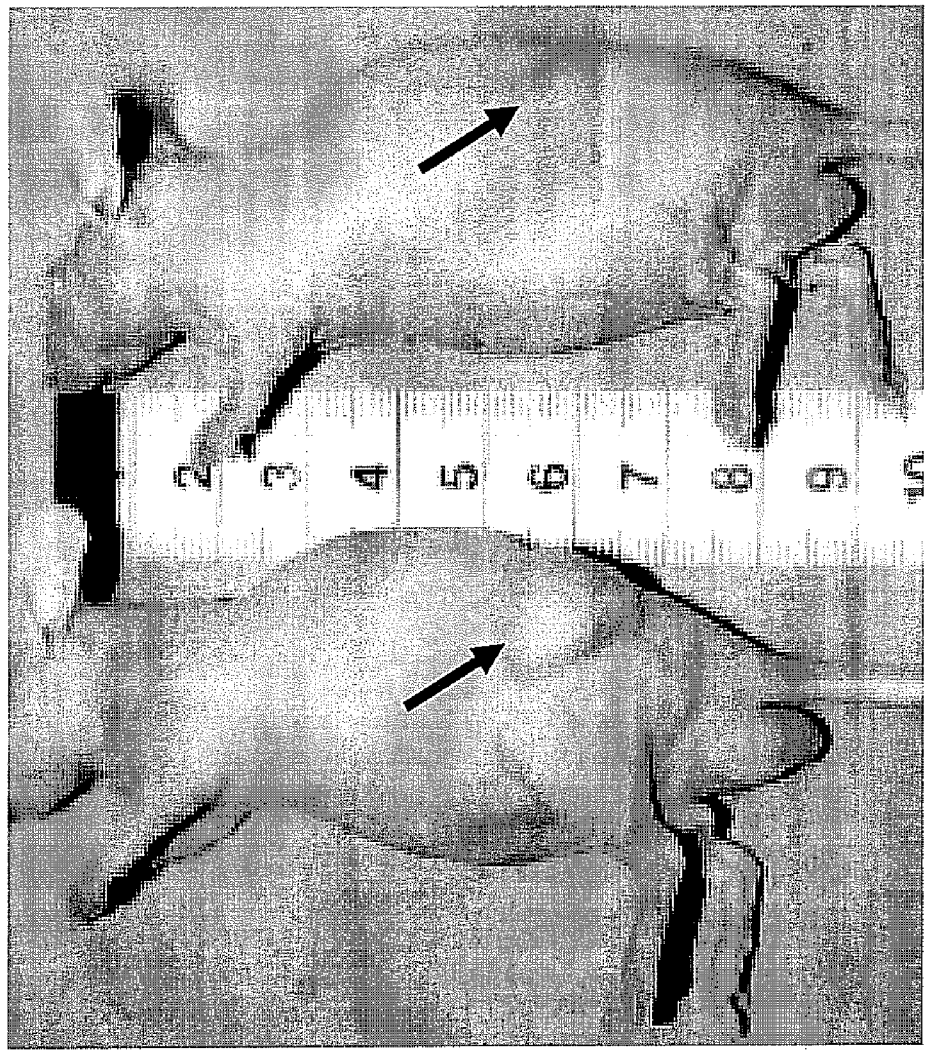
FIG. 13 shows pictures of sacrificed mice which developed a tumor based on RDB257 cells, after treatment with PBS and $5 \times 10^8$ pfu dl520, respectively.

The results are depicted in FIGS. 12 and 13.

FIG. 12 shows a diagram representing the tumor volume as a function of time and the various treatment schemes. In case the tumor was formed by RDB257, there was a significant growth of the tumor to about 438 mm³ to 1466 mm³ upon injection of PBS. Under the influence of the vector dl520 which was used in accordance with the invention, tumor growth could be reduced significantly. Starting from a mean tumor size of 344 mm³, the tumor size increased only by 21% to a total of 543 mm³.

In the present example the tumor consisting of HeLa cells was used as a control which upon administration of PBS behaved similarly to the RDB257 based tumor upon administration of PBS. Tumors based on HeLa cells and treated with dl520, however, still showed a significant increase in tumor growth starting from 311 mm³ and increasing to 1954 mm³.

FIG. 13 shows a picture of the sacrificed nude mice which had a tumor grown using RDB257. It can be clearly seen that after the application of adenovirus dl520 in accordance with the present invention a significant reduction of the tumor occurred. In the present case there was even a reduction in the tumor volume (day 1 after administration of virus dl520: 515 mm³; day 30 after administration of virus dl520: 350 mm³).

EXAMPLE 10

Southern Blot of Tumor DNA

DNA was extracted from a tumor sample which has been taken from the middle of the tumor developed in example 9. For isolation the Dneasy Tissue Kit of Qiagen is used. The DNA isolation is done in accordance with manufacturer's instructions. In accordance therewith, the DNA was released from the cells through alkaline lysis. Subsequently, the isolated DNA is purified over a column. Subsequently, the concentration of the isolated DNA is determined by photometry at 260 nm. The analysis was performed using 2 µg of the DNA samples which were digested with 10 units of restriction enzyme Kpn I. Subsequently, an electrophoretic separation of the samples was performed in a 0.8% agarose gel. Subsequently, the DNA was blotted onto a nylon membrane (performed according to the system of Schleicher & Schuell). The DNA blotted onto the membrane is hybridised against a specific 1501 by DNA probe. The 1501 by DNA probe specifically binds to the 3369 by Kpn I fragment within the E2A coding Ad5 sequence. The probe was prepared prior to that by PCR (primer: 5'-GTC GGA GAT CAG ATC CGC GT (SEQ. ID. No. 2), 5'-GAT CCT CGT CGT CTT CGC TT (SEQ. ID. No. 3)) and radioactively labelled using $^{32}$P. Subsequently, the membrane is washed and exposed to a film.

Figure 14:
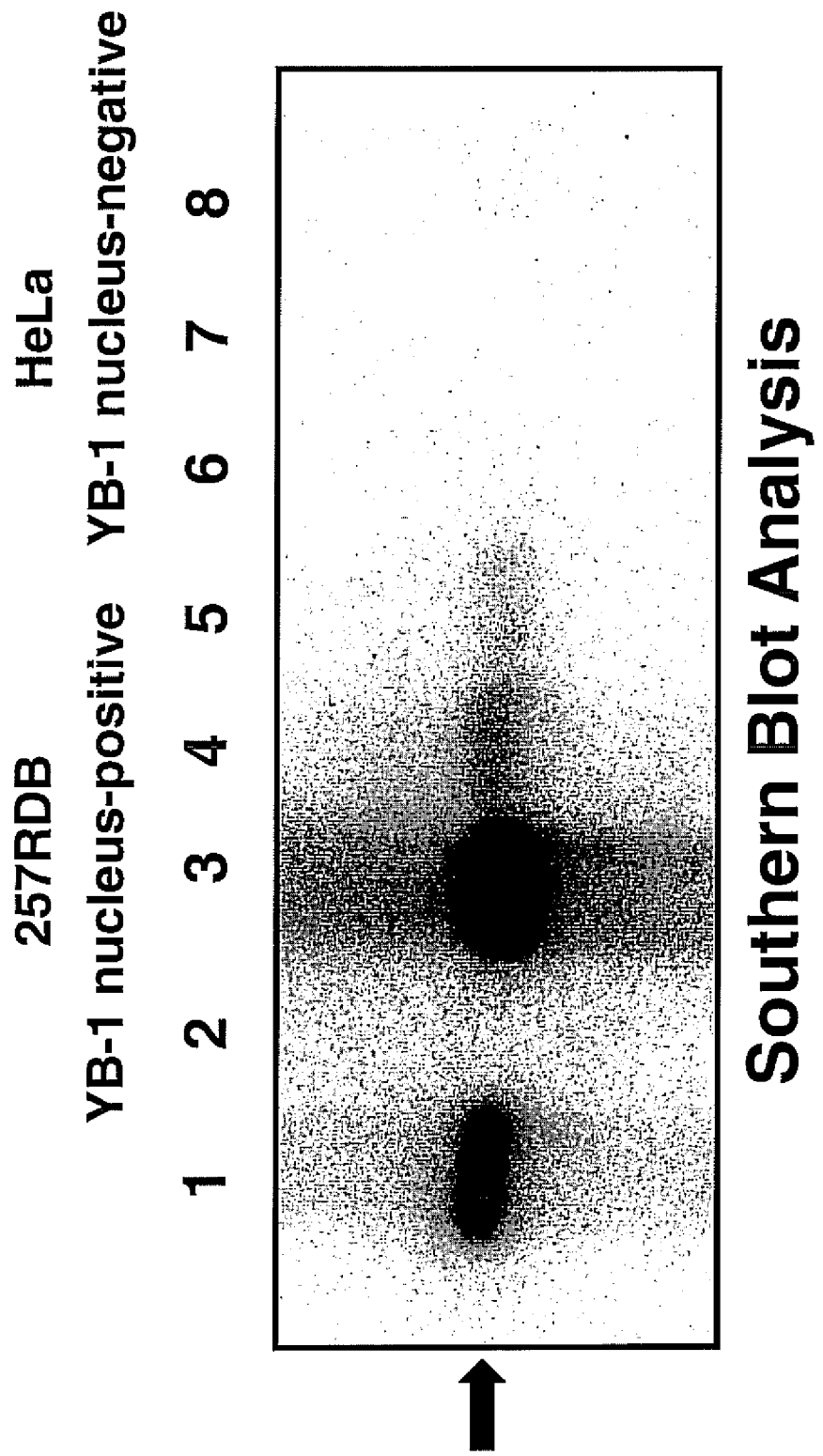
FIG. 14 shows the result of a Southern blot analysis of a cell extract (of subcutaneously grown tumors) of RDB257 cells and HeLa cells after infection with dl520.

The result of the Southern Blot of tumor DNA is depicted in FIG. 14. The analysis confirms that only dl520 replicates in vitro in resistant cells RDB257, as depicted in lanes 3, 4 and 5. Lane 1 shows as positive control Ad-5d, lane 6, 7 and 8 show DNA from HeLa cells which were infected with dl520. As HeLa cells are not YB-1 nucleus positive the virus dl520 did not replicate so that, in accordance therewith, the E2A sequence could not be detected.

Figure 15:
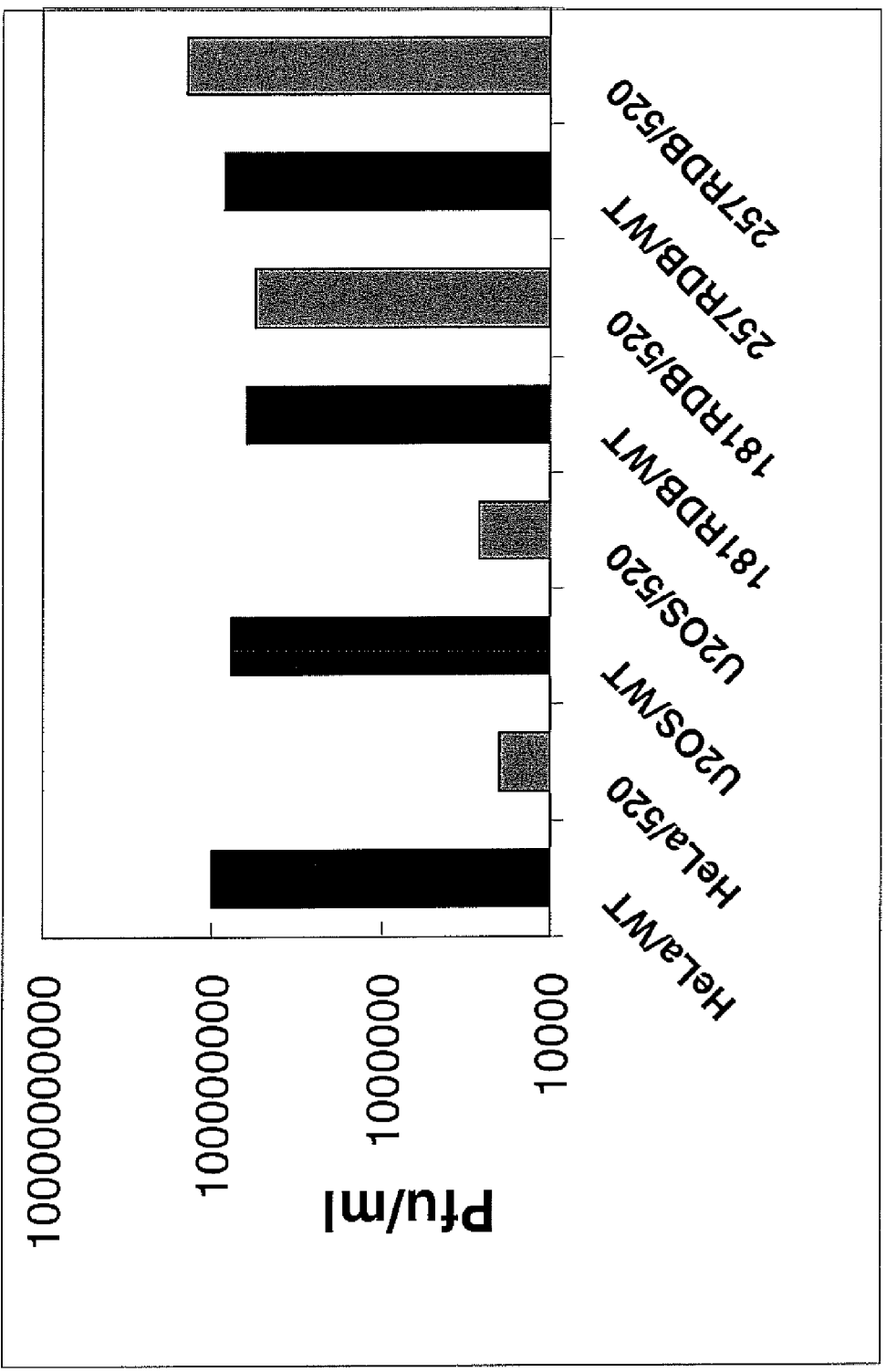
FIG. 15 shows a bar graph indicating replication efficiency and particle formation of dl520 and wildtype adenovirus in YB-1 nucleus-positive tumor cells (257RDB and 181RDB) and YB-1 nucleus-negative tumor cells (HeLa, U2OS)

A further result with dl520 is depicted in FIG. 15. Based on a plaque assay the particle formation (pfu/ml) was investigated after infection with dl520 and wildtype adenovirus. Various YB-1 nucleus-positive (257RDB and 181RDB) tumor cells and YB-1 nucleus-negative tumor cells were infected with dl520 and wildtype adenovirus.

The following procedure was practiced:

100,000-200,000 cells each were plated in so-called plates having 6 wells (engl. 6 well plates) in L 15 medium (resistant cells) and DMEM (non-resistant cells) having 10% FCS. After 24 h infection with dl520 and wildtype adenoviruses (10 pfu/cell) was performed. 3 days after infection (post infectionem) the viral particles were released from the cell suspension (3 ml) by alternating freezing and thawing for three times. Subsequently, a plaque assay was performed on 293 cells for determining the formed infectious particles (plaque forming units per ml (pfu/ml)). The result is depicted in FIG. 15. The result of the plaque assay shows that dl520 is replicating in YB-1 nucleus-positive cells (257RDB and 181RDB) similar to wildtype adenovirus. Insofar a replication efficiency can be observed similar to the one of wildtype adenoviruses when using, in accordance with the present invention, the adenoviruses described herein.

EXAMPLE 11

Structural Design of the Adenoviral Vector Xvir03

FIG. 16 shows the structural design of the adenoviral vector Xvir03. The adenovirus Xvir03 is a so-called E1/E3-deleted adenovirus. This means that no E1A, E1B (E1B55k and E1B19K proteins) and E3 proteins are manufactured which are functional in adenoviral replication. The deletion of the E1 region extends from 342-3528; the deletion of the E3 region of the base position 27865-30995. As used herein, the term "E1-deleted virus" means a virus in which E1 is no longer functionally active. This can be achieved by inactivation with an otherwise mostly intact nucleic acid and amino acid sequence, respectively, however, can also mean a deletion of the E1 region coding proteins having various sizes. Because of the lack of the E1A and E1B protein and the nucleic acids coding therefor, the E4 region, such as E4orf6, is only weakly expressed (about 1-5% compared to wildtype adenoviruses) or expressed not at all. The viral genes E1B55k and E4orf6 are expressed in the E1 region by means of the heterologous CMV promoter (Clontech: Plasmid pShuttle) introduced into Xvir03. Instead of the CMV promoter each and any of the promoters as disclosed herein in connection with the expression of E1A can be used. The open reading frames of both genes are linked with each other by means of a so-called IRES sequence (engl. internal ribosomal entry site) (Pelletier, J. and Sonenberg, N. Nature, 1988, 334, 320-325). This element (Novagen: pCITE) provides for the expression of 2 proteins from one mRNA.

The vector was manufactured as follows: System Adeno-X of the company Clontech

The plasmid E1B55k-pShuttle was created by cloning the open reading frame of E1B55k from pCGNE1B from M. Dobelstein (University of Marburg) with XbaI and BfrI into the pShuttle vector from Clontech. Alternatively, the BamH1 fragment from the pCGNE1B vector can, after having been made blunt ended, cloned into the correspondingly prepared pShuttle vector of Clontech. Subsequently, E1B55k in pShuttle was linearised with ApaI, the ends blunt ended and cut with NheI.

In a second vector, pcDNA3.1(+) (Invitrogen), subsequent to each other, the IRES element as a PCR product was cloned with pCITE-4a(+) of the company Novagen as template by means of TA cloning into the EcoRV cleaving site, and the E4orf6 from the plasmid pCMV-E4orf6 (M. Dobelstein, University of Marburg) was cloned by means of BamHI=IRES-E4orf6-pcDNA3.1(+). IRES-E4orf6 in pcDNA3.1(+) was linearised with NotI, the ends blunt ended and subsequently the fragment IRES-E4orf6 was cut out with NheI. The fragment IRES-E4orf6 was linked with the open vector E1B55k-pShuttle (blunt, NheI). The cassette was subsequently cloned from the E1B55k-IRES-E4orf6-pShuttle together with the CMV promoter and the bovine growth hormone (BGH)-PolyA into the ΔE1, ΔE3 Adeno-X-Plasmid (Clontech) with I-Ceu I and PI-SceI, and referred to as AdcmvE1B/IRES/E4orf6. Subsequently, the adenovirus was prepared in accordance with manufacturer's instructions (Clontech). The adeno plasmid which was linearised with PacI having the expression element CMV-E1B55k-IRES-E4orf6-BGH polyA was transfected into HEK293 cells and 11 days post transfectionem the ablating cells were removed together with the medium in order to release the generated adenoviruses through repeated freeze-thaw cycles.

It is within the present invention and feasible for the one skilled in the art with regard to the technical teaching provided herein, that other systems such as the system AdEasy of QBIOGENE and Microbix may be used for the manufacture of the adenoviruses according to the present invention, preferably the recombinant adenovirus, in particular those which contain, individually and/or together, the cassettes E4orf6-IRES-E1B55k and YB-1-IRES-E1A12S. Additionally, individual transgenes may be exchanged between the cassettes. It is within the present invention that also such adenoviruses can be manufactured and used in accordance with the present invention, where the cassette has the following design: E1B55k-IRES-E4orf6 and E1A12S-IRES-YB1.

In connection with the present invention a so called E1/E3 deleted recombinant adenovirus was used which contains the cassette E4orf6-IRES-E1B55k. It is, however, within an embodiment that the virus comprises only an E1-deletion, which means that the E3-region remains intact. Optionally, the E4-region may be partially and/or completely deleted.

In the manufacture of the vector using different systems it was proceeded as follows.

Manufacture of the adenovirus Ad-Xvir 3'UTR having an intact E3-region with the vector system according to Graham (company Microbix).

Cloning of the Vector CMV-E4ORF6-IRES-E1B55k 3'UTR-polyA in pDelta E1sp1A

For the plasmid E1B55k 3'UTR-pShuttle (Clontech) the open reading frame having the 3'-UTR was prepared by amplification from the DNA of adenovirus type 5 (E1B55k forward primer=5'-ATGGAGCGAAGAAACCC-3' (SEQ. ID. NO. 9) and E1B55k 3'UTR backward primer=5'-CACGTCCTGGAAAAAATACAC-3') (SEQ. ID. NO. 10) and introduced in the blunt ended NheI restriction site, which was provided with T-ends (TA-cloning) and cloned into the pShuttle plasmid of the company Clontech. Thus, the transgene was provided with a hCMV-promoter at the 5' end and with the bovine growth hormone polyadenylation signal at the 3' end.

Cloning of the Vector E4ORF6-IRES-pcDNA3.1(+)

The amplificates E4orf6 using the adenovirus type 5 DNA as template (E4orf6 forward primer 5'-CTTCAGGATCCAT-GACTACGTCCGGCG-3' (SEQ. ID. NO. 11), and E4 or f6 backward primer 5'-GAAGTGAATTCCTACATGGGGG-TAGAGTCATAATCGT-3' (SEQ. ID. NO. 12) and from the plasmid pCMVE4-34 kD which has been cut with Bam HI (Dobbelstein et al., EMBO, 16, 4276-4284, 1997), and the IRES element having the pCITE-4a(+) of the company Novagen as template (IRES forward primer=5'-TCCGGT-TATTTTCCACCATATTGC-3' (SEQ. ID. NO. 13), and IRES backward primer=5'-TTATCATCGTGTTTTTCAAAGG-3') (SEQ. ID. NO. 14) were subsequently cloned into the multiple cloning site of the pcDNA3.1(+)-vector. For such purpose, primers were used for the E4orf6 transgene which create a BamHI cleavage site at the 5'-end and a EcoRI cleavage site at the 3'-end of the open reading frame. The amplificate was digested with the respective restriction enzymes and the ends thereof were made compatible for the directed cloning into the vector which has been opened using BamHI and EcoRI. Subsequently, plasmid E4orf6 in pcDNA3.1(+) was linearized with EcoRV, the T-ends added and the amplificate cloned into the IRES element. After checking the correct orientation of the IRES element, the vector was used for further cloning.

The linkage of both transgenes with the IRES element resulted from a cloning of the E4orf6-IRES cassette into the previously generated plasmid CMV-E1B55k 3'UTR-polyA-pShuttle (Clontech) which was linearized with NotI, blunt ended and subsequently cut with XbaI. E4orf6-IRES in pcDNA3.1 (+) was linearized with NotI, the ends made blunt ended and further digested with NheI. By ligating the E4orf6-IRES insert with the CMV-E1B55k 3'UTR-polyA-pShuttle (Clontech) XVIR-3'UTR was generated in pShuttle (Clontech).

Generation of the Used Adenoviral Shuttle Vector

As the shuttle vector pΔE1sp1A, now used for the adenoviral generation system of the company Microbix, did neither contain a CMV promoter nor a bovine growth hormone polyadenylation signal, these elements were cloned into pΔE1sp1A. For such purpose, pΔE1sp1A was linearized with ClaI, made blunt ended and cut with EcoRI. The element CMV-MCS (multiple cloning site)-poly-A was linearized from pShuttle (Clontech) with MfeI, the ends made blunt ended and further cut with EcoRI. Subsequently, the cassette (Xvir-3'UTR pShuttle from Clontech) was cloned with PmeI into the CMV-MCS-poly-A pΔE1 sp1A vector which had also been cut with PmeI and subsequently dephosphorylated. The cloning product Xvir-3'UTR-pΔE1sp1A was used for virus generation.

Virus Generation

Xvir-3'UTR-pΔE1sp1A and pBHGE3 (from Microbix, contains the E3-region which corresponds to wildtype adenovirus type 5) was cotransfected into HEK 293 cells, whereupon virus Ad-Xvir-3'UTR E3 was generated due to recombination of homologous sequences of both vectors.

Generation of Adenovirus Ad-Xvir3'UTR-AdEASY E3 Using the AdEASY-system (Company Qbiogene)
Generation of the Used Adenoviral Shuttle Vector As, for the present used system, the vector pShuttle-AdEASY did neither contain a CMV-promoter nor the bovine growth hormone polyadenylation signal, these elements were cloned into pShuttle-AdEASY. For such purpose, the plasmid was digested with EcoRI, the ends made blunt ended by fling them up with T4-polymerase and dNTPs, the backbone was dephosphorylated and both of the generated digestion products ligated again. By doing so the restriction recognition site for EcoRI was eliminated. The thus resulting plasmid was referred to as pShuttle(-EcoRI)-AdEASY.

Subsequently, the cassette CMV-MCS-polyA from the pShuttle of Clontech was cut with MfeI and EcoRI, the ends made blunt ended and cloned into the vector pShuttle (-EcoRI)-AdEASY which was, for such purpose, linearized with XbaI, made blunt ended and dephosphorylated. Thus plasmid CMV-MCS-polyA-pShuttle-AdEASY was generated. The cassette E4Orf6-IBES-E1B55k-3'UTR was cloned into this plasmid using MluI and EcoRI. By doing so the plasmid Xvir-3'UTR in pShuttle AdEASY was generated. This was linearized with Bst1107I and MroI and introduced into BJ5183 (EC) bacteria together with rescue-plasmid pAdEASY by means of electroporation. By homologous recombination the adenoviral plasmid Ad-Xvir-3'UTR-pAdEASY was generated which resulted in virus production after transfection in HEK293 cells.

Introducing the wt E3 Region into pAdEASY

As the E3 region is substantially deleted in plasmid pAdEASY, the E3 region was cloned from plasmid pAdEASY with SpeI and PacI into plasmid CMV-MCS-polyA pShuttle (AdEASY) for reconstruction and thus the plasmid E3E4-pShuttle-AdEASY generated.

By restriction with NdeI and religation one out of two NdeI restriction sites was deleted and so was the multiple cloning site from the plasmid. By this procedure plasmid E3E4-pShuttle(-NdeI)-AdEASY was generated.

Subsequently the 4007 by wtE3-region fragment from wildtype adenovirus type 5 was excised by SpeI and NdeI and cloned into the E3E4-pShuttle (-NdeI)-AdEASY which was opened by SpeI and NdeI. The thus generated vector was referred to as wtE3E4-pShuttle (NdeI)-AdEASY.

Subsequently the wildtype E3E4-region from the E3E4-pShuttle (-NdeI)-AdEASY was cut with SpeI and PacI and cloned into the pAdEASY and cut with SpeI and PacI, whereby in plasmid pAdEASY the E3-region was re-established (pAdEASY-E3). XVir-3'UTR-pAdEASY-E3 was generated by homologous recombination upon transforming BJ5183 (EC) bacteria with plasmids Xvir-3'UTR in pShuttle AdEASY and pAdEASY-E3.

Manipulation of E4 for all of the Systems Mentioned

In order to provide space for therapeutic genes and transgenes and in order to avoid undesired homologous recombination the E4 region in plasmid E3E4-pShuttle (-NdeI)-AdEASY can be deleted specifically. For such purpose, the E4orf6 region is shortened by about 0.6 kB, preferably 634 bp, by excision with PstI and religation. This can, as described in FIG. 17, be performed in connection with Xvir03/01. Respective deletions are also feasible by the one skilled in the art in different systems for the generation of recombinant adenovirus.

Cloning of the RGD-motif in Ad-Xvir 3'UTR-AdEASY E3 in Particular (Also Applicable to Other Systems)

For increasing the infectivity the HI Loop of the fibre knob domain was modified following Dmitriev et al. 1998 (An Adenovirus Vector with Genetically Modified Fibers Demonstrates Expanded Tropism via Utilization of a Coxsackievirus and Adenovirus Receptor-Independent Cell Entry Mechanism): The respective region was amplified using the primers RGD-Hpa fw (5'-GAGgttaacCTAAGCACTGCCAAG-3') (SEQ. ID. NO. 15); RGD-EcoRV rev (5' CATAGAGTATG-CAGATATCGTTAGTGTTACAGGTTTAGTTTTG-3') (SEQ. ID. NO. 16) and RGD-EcoRV fw (5'-GTAACAC-TAACGATATCTGCATACTCTATGTCATTTTCATGG-3') (SEQ. ID. NO. 17), and RGD-Bfr rev (5'-CAGCGACAT-GAActtaagTGAGCTGC-3') (SEQ. ID. NO. 18), and thus an EcoRV restriction site generated. In this restriction site the paired oligonucleotides were cloned which code for an Arg-Gly-Asp (RGD)-peptide: RGD-oligo 1 (5'-CACAC-TAAACGGTACACAGGAAACAGGAGACA-CAACTTGTGACTGCCGCGGAGACT GTTTCTGCCC-3') (SEQ. ID. NO. 19), and RGD-oligo 2 (5'-GGGCAGAAACAGTCTCCGCGGCAGTCACAAG TTGTGTCTCCTGTTTCCTGTGT (SEQ. ID. NO. 20). Thus, the RGD motif is present in the HI Loop of the fibre knob domain.

The vector described above is in principle suitable as are the other viruses described herein for use in accordance with the present invention. In particular the afore-described vector is suitable to replicate and trigger lysis insofar, in cells which are YB-1 nucleus-positive cells as well as in cells where YB-1 is deregulated, i.e. is overexpressed compared to normal cells and non-tumor cells, respectively. The use of this vector particularly applies to those diseases and groups of patients or groups of patients which are disclosed in connection with the other adenoviruses which are described herein to be used in accordance with the present invention and the other adenoviruses of the present invention disclosed herein.

EXAMPLE 12

Structural Design of the Adenoviral Vector Xvir03/01

Figure 17:
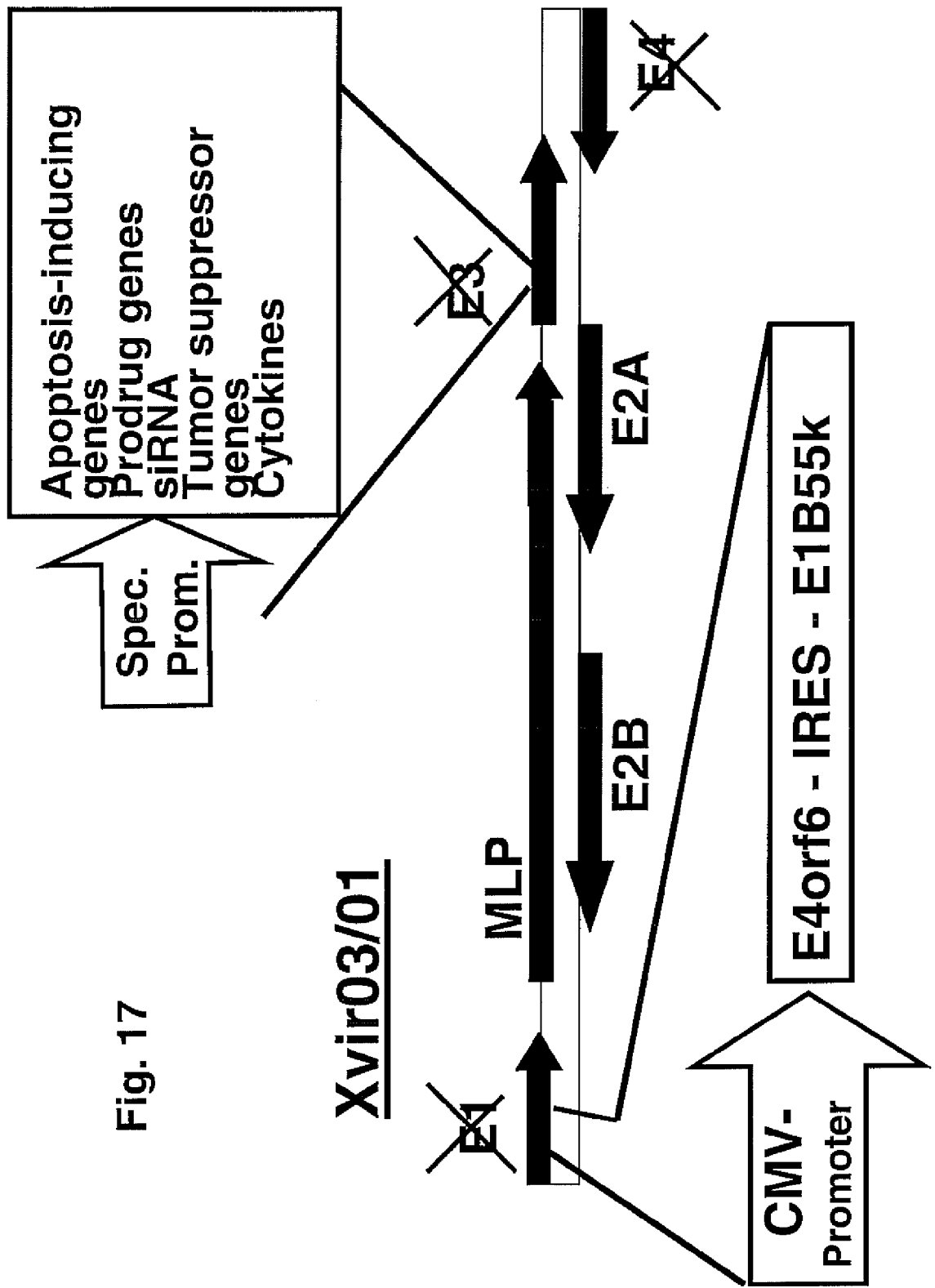
FIG. 17 shows the structural design of the adenoviral vector AdXVir03/01.

As may be taken from FIG. 17, Xvir03/01 is a further development of Xvir03. Therapeutic genes such as, for example, the genes described herein and the transgene can be cloned into the E3 region. Additionally, a deletion was introduced into the E4 region so as to avoid homologous recombination with the E4orf6 from the expression cassette of Xvir03. This allows that larger transgenes can be cloned in this construct. The deleted E3 region contains SacI, NdeI and NheI cleavage sites for introducing a cassette, into which, for example, the therapeutic transgenes can be cloned. However, the E3 region may also stay intact and the therapeutic genes may be clines into the E4 region. Thus, among others, the expression of the adenoviral death protein ADP is ensured.

Preparing a Plasmid for Cloning Therapeutic Genes into the E3 Region as Well as for Making Deletions in the E4 Region: System Adeno-X of Clontech The pAdenoX-Plasmid of Clontech has a restriction site for SfuI behind the 3' ITR region which is absent in wildtype adenovirus. The E3-E4 region was taken from pAdenoX (Clontech) with the SpeI (position 23644) and SfuI and transferred into pcDNA3.1(+) (Invitrogen)=pcDNA3.1-E3Δ27865-30995-E4. The bigger part of E4ORF6, namely 33241-33875 was removed by means of PstI=pcDNA3.1-E3Δ27865-30995,E4Δ33241-33875. For the further development of Xvir03 the deleted E3/E4 region from pcDNA3.1-E3Δ27865-30995,E4Δ33241-33875 was cloned by means of SfuI and SpeI into plasmid pAdenoX=pAdenoX E3Δ27865-30995,E4Δ33241-33875.

The expression cassette was subsequently, as described for Xvir03, cloned with I-Ceu I and PI-SceI from the E1B55k-

IRES-E4orf6-pShuttle together with the CMV promoter and the bovine growth hormone (BGH)-PolyA into pAdenoX E3Δ27865-30995,E4Δ33241-33875 and referred to as AdcmvE1B/IRES/E4orf6-ΔE4. Subsequently, the adenovirus was prepared in accordance with manufacturer's instructions (Clontech).

It is within the present invention and feasible for the one skilled in the art in the light of the present disclosure that other systems may be used for the manufacture of the adenoviruses in accordance with the present invention and in particular the recombinant adenoviruses, such as the systems of the companies QBIOGENE and Nicrobix.

The afore-described vector is in principle useful as are the other viruses described herein to be used in accordance with the present invention. In particular the afore-described vector is suitable to replicate in YB-1 nucleus-positive cells as well as cells in which YB-1 is deregulated, i.e. is overexpressed compared to normal cells and non-tumor cells, and to cause lysis insofar. This vector can also be used for those diseases and groups of patients and collectives of patients which are disclosed herein for the other adenoviruses to be used in accordance with the present invention and the adenoviruses in accordance with the present invention.

EXAMPLE 13

Oncolytic Effect of Xvir 03 in 257 RDB and 181 RDB Cells 100,000 cells (257RDB and 181RDB) were plated per well of a plate having six wells (engl.: 6 well plate). AT the next day the cells were, as depicted in FIG. 18, infected with Ad312 (20 pfu/cell) and Xvir03 (5 pfu/cell). The infection was performed in 500 µl serum free DMEM medium at 37° C. for 1 h. Subsequently, the infection medium was removed and replaced by 2 ml complete medium (10% FCS/DMEM). The analysis was done by means of crystal violet staining after 5 days. The result is depicted in FIGS. 18A and 18B.

As may be taken from FIGS. 18A and 18B, the multidrug resistant cells which have YB-1 in the nucleus, show lysis after infection with Ad312 and Xvir03 only in case of Xvir03 as represented by the crystal violet staining of the cells. In connection therewith, first the medium is removed. Subsequently the cells are covered with crystal violet (50% ETOH, 3% formaldehyde, 5% acetic acid, 1% crystal violet) and incubated at room temperature for 5-10 min. Subsequently, the six well plates are thoroughly rinsed with water and dried at room temperature.

It is known to the present inventor that E1A-deleted viruses (e.g. Ad312) which, however, are not transactivating adenoviruses in the sense of the present invention, may replicate very efficiently at higher MOIs (Nevins J. R., Cell 26, 213-220, 1981), which, however, cannot be realised in clinical application. This phenomenon is referred to in the literature as "E1A-like activity". The adenovirus Ad312 as used herein, is an E1A-deleted virus. At the titer used (20 pfu/cell), which is still above the clinically desirable titer, the early adenoviral genes such as E1B55k and E4orf6 are not expressed or expressed only to a very small extent (Nevins J. R., Cell 26, 213-220, 1981). As already described herein, these genes and proteins play an important role in viral replication. In contrast thereto, these genes and proteins, respectively, are expressed by adenovirus Xvir03 (FIG. 16). As may be taken from FIGS. 18A and 18B, the expression of the genes E1B55k and E4orf6 will result in an efficient viral replication and cell lysis at a concomitantly lower infection titer required (expressed as pfu/cell). This confirms the finding underlying the present invention, namely that the expression of E4orf6 and E1B-55K (and the absence of E1A) in combination with nuclear localisation of YB-1 is capable of inducing a very efficient adenoviral replication. The titer required therefor of only 1 to 5 pfu/cell now allows for clinical application.

This confirms the finding underlying the present invention, namely that the presence of YB-1 in the nucleus, particularly the presence independent from the cell cycle, is required in order to make the viruses which are to be used in accordance with the present invention, lyse infected cells.

EXAMPLE 14

Northern Blot Analysis of the E2 Gene Expression of Adenovirus Ad312

In each case 1 million A549 and U2OS cells were plated in 10 cm Petri dishes. At the next day the cells were infected with Ad312 (50 pfu/cell) and Adwt (which served as control, 5 pfu/cell). The high virus titer of Ad312 which was used resulted in an E1-independent replication in tumor cells. The infection was done in 1-2 ml serum-free DMEM medium for 1 h at 37° C. Subsequently, the infection medium was removed and replaced by 10 ml complete medium (10% FCS/DMEM). After 3 days the RNA was isolated. Subsequently, the concentration of the isolated RNA was measured in a photometer at 260 nm. Then the RNA samples were electrophoretically separated in a 0.8% formaldehyde agarose gel. Subsequently, the RNA was blotted on a nylon membrane (conducted according to the system of Schleicher & Schuell). The RNA blotted on the membrane is blotted against an "early probe" E2 and a "late probe" E2. The 1501 by "late probe" specifically binds behind the E2-late promoter. The probe was prepared prior to that by PCR (primer: 5'-GTC GGA GAT CAG ATC CGC GT (SEQ. ID. NO. 4), 5'-GAT CCT CGT CGT CTT CGC TT (SEQ. ID. NO. 5)) and radioactively labelled using $^{32}$P. In contrast, the early probe binds between the E2-early promoter and the E2-late promoter (position: 226791-227002) and was also generated by means of PCR (primer: 5'-AGCTGATCTTCGCTTTTG (SEQ. ID. NO. 6), 5'-GGATAGCAAGACTCTGAC AAAG (SEQ. ID. NO. 7)). Subsequently, the membrane was washed and exposed to a film.

The result is depicted in FIG. 19. Both the early as well as the late probe provided specific signals in the control infection with wildtype adenovirus, whereas tumor cells infected with Ad312 only provided a specific signal when the late probe was used. This confirms the finding underlying the present invention that the expression of E4orf6 and E1B55K and the absence of E1A transports overexpressed and deregulated YB-1, respectively, into the nucleus and thus induces E2 gene expression as a prerequisite for efficient adenoviral replication.

EXAMPLE 15

Northern Blot Analysis of the E2 Gene Expression of Adenovirus Addelta 24

In each 1 million U2OS cells were plated in 10 cm Petri dishes. At the next day the cells were infected with adenovirus delta 24 (Addelta24) (10 pfu/cell) and wildtype adenovirus (Adwt) (served as a control, 10 pfu/cell). The used recombinant adenovirus Addelta24 (Fueyo, J. et al., Oncogene 19, 2-12, 2000) has a specific deletion in the CR2 region of the E1A protein and is thus only capable of replicating in Rb-negative tumors. Additionally, the virus expresses the genes E1B55k and E4orf6 comparable to the wildtype adenovirus.

The infection occurred in 1-2 ml serum-free DMEM medium for 1 h at 37° C. Subsequently, the infection medium was removed and replaced by 10 ml complete medium (10% FCS/DMEM). The RNA was isolated after 12 h and 24 h. Subsequently, the concentration of the isolated RNA was determined in a photometer at 260 nm. Then the RNA samples were electrophoretically separated in a 0.8% formaldehyde agarose gel. Subsequently, the RNA was blotted on a nylon membrane (conducted according to the system of Schleicher & Schuell). The RNA blotted onto the membrane is hybridised against the "early probe" and against the "late probe". The "late probe" comprising 1501 bp, binds specifically behind the E2-late promoter. The probe was prepared prior to that by PCR (primer: 5'-GTC GGA GAT CAG ATC CGC GT (SEQ. ID. NO. 4), 5'-GAT CCT CGT CGT CTT CGC TT (SEQ. ID. NO. 5)) and radioactively labelled using $^{32}$P. The early probe, however, binds between the E2-early promoter and the E2-late promoter and was also prepared by PCR (primer: 5'-AGCTGATCTTCGCTTTTG (SEQ. ID. NO. 6), 5'-GGATAGCAAGACTCTGACAAAG (SEQ. ID. NO. 7)). Subsequently, the membrane was washed and exposed to a film.

The result is shown in FIG. 20.

After 12 h only the late probe provided for a specific signal. Only after 24 h also the early probe provided a signal in cells infected with Addelta24. Compared to wildtype adenoviruses, however, the signal is significantly weaker. Also this result confirms the finding underlying the present invention that the expression of E4orf6 and E1B-55K transports overexpressed and deregulated YB-1, respectively, into the nucleus which subsequently binds to the E2-late promoter and induces E2 gene expression.

EXAMPLE 16

Structural Design of the Adenoviral Vectors XvirPSJL1 and XvirPSJL2

Description of the vectors: The vectors of the XvirPSJL group which are embodiments of the viruses referred to herein as group I adenoviruses and which are exemplified by the vectors and adenoviruses, respectively, XvirPSJL1 and XvirPSJL2, are not only, like adenovirus dl520, capable of replicating in YB-1 nucleus-positive cells, in particular tumor cells, but also in tumor cells in which YB-1 is overexpressed and deregulated, respectively. While the viral genes E1B55k and E4orf6 are expressed only in dl520 infected YB-1 nucleus-positive cells under the influence of the E1B promoter and the E4 promoter, respectively, the expression of E1B55k and E4orf6 in XvirPSJL occurs by means of the cytomegalovirus (cmw) promoter. Instead of the cmw promoter, however, also other promoters, in particular tumor-specific, tissue-specific and organ-specific promoters and the natural E1A promoter, i.e. preferably the E1A promoter as present in wildtype adenovirus, preferably Ad5, may be used. Because of the expression of E1B55k and E4orf6 the overexpressed YB-1 and the deregulated YB-1, respectively, is transported into the nucleus and adenoviral replication is initiated. The adenoviral vectors of the XvirPSJL group as disclosed herein, thus combine various elements and thus functions of the adenoviral vectors dl520, Xvir03 and AdYB-1 in a single vector. Similar to the vector dl520 the XvirPSJL viruses contain the E1A12S gene. This gene and the corresponding gene product, respectively, is responsible for the induction of the S phase of the infected cell and promotes viral replication and the effect of chemotherapeutics and irradiation. Like Xvir03 the XvirPSJL viruses contain the expression cassette CMV-E4orf6/IRES/E1B55k, which is required for an efficient replication and indirectly or directly transports deregulated YB-1 into the nucleus which is preferably contained in tumor cells. Thus replication is possible only in cells, particularly tumor cells, where YB-1 is overexpressed or deregulated. Additionally, P53 is made subject to degradation by the E1B55k/E4orf6 complex. The sequence coding for human transcription factor YB-1 is taken from the virus AdYB-1. The endogenous, i.e. the YB-1 already present in the cell amplifies viral replication. The expression of both E1A12S and YB-1 is controlled by the YB-1-dependent adenoviral E2-late promoter. Also in connection therewith specific promoters may be used, in particular tumor-specific, tissue-specific or organ-specific promoters. A further feature of these viruses is that the E4 region is deleted. The vector contains restriction sites there by which, in case of the adenoviral vectors XvirPSJL1 and XvirPSJL2, various transgenes as disclosed in the specification such as ribozymes, antisense molecules, siRNA, apoptosis-inducing genes, cytokines and prodrug genes may be expressed. Their expression may also be controlled by tumor-specific, tissue-specific or organ-specific promoters as disclosed in the specification. The localisation of the expression cassettes is not fixed, particularly not with regard to or within the E1, E3 and E4 region, but can be arranged in any way. In connection therewith the non-required can be either deleted or can be intact. The vectors replicate independent of the p53 or Rb status of the tumor cells.

The structural designs of the recombinant adenoviruses XvirPSJL1 and XvirPSJL2 are presented in FIGS. 21 and 22:
Generation of the vector XvirPSJL according to the system of aden-X of Clontech.
Generation of the Cassette E2-late-YB1IRES/12S:

The pAdenoX plasmid of Clontech/BD Biosciences which is used as a starting material herein, comprises the genomic nucleic acid of adenovirus Ad5 and has a SfuI restriction site behind the 3' ITR region which is ABSENT in wildtype adenovirus. The E3-E4 region was transferred by SpeI (position 23644) and SfuI from pAdenoX (Clontech) into pcDNA3.1(+) (Invitrogen) and referred to as pcDNA3.1-E3Δ27865-30995-E4. The majority of the E4ORF6, namely the bases 33241-33875 were removed by means of PstI. The such obtained fragment was referred to as pcDNA3.1-E3Δ27865-30995, E4Δ33241-33875.

The E2-late promoter was excised from pGL3-EGFP (Holm et al., JBC 2002, 277, 10427-10434) with SacI and NheI and cloned into pcDNA3.1-E3Δ27865-30995, E4Δ33241-33875. In doing so, the E3 region was further deleted in the region of bases Δ27593-31509. The thus obtained fragment was referred to as E2-late-pcDNA3.1-E3Δ27593-31509, E4Δ33241-33875

The cDNA for the E1A-243AA product was generated by means of RT-PCR, isolated and the sequence checked and cloned into the pcDNA3.1(+) vector (Invitrogen) using BamHI and EcoRI. E1A-12S-pcDNA3.1+ was linearised with NheI and BamHI, made blunt-ended by T4 polymerase and provided with T overhangs by Taq polymerase and dTTPs. The IRES element was cloned as a PCR product (template=pCITE, Novagen) into the E1A-12S-pcDNA 3.1 (+) vector (TA cloning strategy).

The YB-1-EcoRI fragment was isolated from the vector pHVad2c (Holm et al., JBC 2002, 277, 10427-10434) and made blunt-ended. The vector pShuttle (commercially available from BD Biosciences) was linearised with XbaI, the ends made blunt-ended and dephosphorylated and ligated with the previously produced YB-1 coding nucleic acid. The vector thus obtained was referred to as YB-1-pShuttle. The cloning into the pShuttle vector provided the YB-1 fragment coding nucleic acid with an in-frame STOP codon. The YB-1 coding nucleic acid was cloned from the YB-1-pShuttle by means of NheI and BfrI into the vector IRES-E1A-12S in pcDNA3.1 (+). The thus obtained fragment was referred to as YB-1 (EcoRI-EcoRI with STOP codon)-IRES-E1A-12S-pcDNA3.1(+).

Subsequently, the cassette YB-1-IRES-E1A12S was excised with PmeI and cloned into the NheI linearised, blunt-ended and dephosphorylated vector E2late-pcDNA3.1 E3Δ27593-31509, E4Δ33241-33875. Thus the second cassette is in the deleted region of the E3 region.

The transgene cassette comprising the nucleic acid construct E2late-YB-1-IRES-E1A12S was cloned together with the remaining adenoviral sequences E3Δ27593-31509, E4Δ33241-33875 by means of SfuI and SpeI into the vector pAdenoX of Clontech (=AdenoX/E2late-YB-1-IRES-E1A12S/E3Δ27593-31509, E4Δ33241-33875).

The cassette CMV-E1B55k/IRES/E4orf6 was excised by means of I-CeuI and PI-SceI from the pShuttle described above in relation to Xvir03 and inserted into the vector AdenoX/E2late-YB-1-IRES-E1A12S/E3Δ27593-31509, E4Δ33241-33875.

Subsequently, the vector was linearised with Pac I, transfected into 293 cells and the recombinant adenovirus XvirPSJL1 and XvirPSJL 2, respectively, isolated without the transgenes indicated in the figure in accordance with manufacturer's instructions.

It is within the present invention and feasible for the one skilled in the art in the light of the present disclosure that other systems may be used, such as the system of the companies QBIOGENE and MICROBIX, for the generation of the adenoviruses in accordance with the present invention, preferably recombinant adenovirus and in particular those containing, separately and/or together, the cassettes E4orf6-IRES-E1B55k and E1A12S-IRES-YB-1, respectively. Additionally, the individual transgenes can be exchanged within the individual cassettes and in particular among the respective cassettes. Additionally, the cassette E1A12S-IRES-YB-1 may consist only of E1A12S and/or E1A12S can be linked to other relevant genes through IRES.

Generation of the Adenovirus AdPSJL-E2-late Promoter-12S-AdEASY with E1A12S in the Deleted E3-region with the AdEASY-system (Company Microbix).
Cloning of PSJL 12S First, the E2-late promoter was cloned into the HindIII and BglII cleavage site of the pGL3-enhancer plasmid (pGL3-E2-late) as paired oligonucleotides (upper primer 5'-TC-GAGCTCCGCATTTGGCGGGCGGGATTG-GTCTTCGTAGAACCTAATCTCGTGGG
CGTGGTAGTCCTCAGGTACAAAT-3'(SEQ. ID. NO. 21) and lower primer 5'-AGCTTATTTGTACCTGAGGAC-TACCACGCCCACGAGATTAGGTTCTAC-
GAAGACCAA TCCCGCCCGCCAAATGCGGAGC-3' (SEQ. ID. NO. 22).

Subsequently, the luciferase gene was excised using NcoI and XbaI, the ends made blunt ended and T-ends added. The transgene E1A 12S which was amplified by the primers E1A 12S forward primer 5- ATGGCCGCCAGTCTTTTG-3' (SEQ. ID. NO. 23) and E1A 12S backward primer 5'-TTATGGCCTGGGGCGTTTAC-3'(SEQ. ID. NO. 24), was introduced by TA-cloning into the thus opened site.

This cassette was excised using PvuI and ClaI, the ends made blunt ended and cloned into the blunt ended and dephosphorylated NheI-cleavage site in the E3-region of E3E4-pShuttle (-NdeI)-AdEASY. The cassette thus contains the E2-late promoter, the open reading frame E1a-12S and the SV-40 late polyadenylation signal. The resulting construct is E2-late-E1a-12S-E3E4-pShuttle(-NdeI)-AdEASY.

Subsequently the E2-late-E1a 12S-E3E4 was excised from the E2-late-E1a 12S-E3E4-pShuttle (-NdeI)-AdEASY using SpeI and PacI and cloned into the SpeI and PacI cut pAdEASY. The thus resulting construct was referred to as E2-late-E1a 12S-E3E4-pAdEASY.

AdPSJL-12S-AdEASY was generated by homologous recombination upon transforming BJ5183 (EC) bacteria with the plasmids Xvir-3'UTR in pShuttle AdEASY and E2-late-E1a 12S-E3E4-pAdEASY.

Generation of the Adenovirus AdPSJL-E2-late Promoter-12S-YB-1-AdEASY with E1A12S and YB-1 in the Deleted E3-region Using the AdEASY System (Company Microbix)
Cloning of the Vector E4ORF6-IRES-pcDNA3.1(+)

The amplificates E1a 12S (see above) and the IRES element (see above) were subsequently cloned into the multiple cloning site of the pcDNA3.1(+)-vector. For such purpose the E1a-12S amplificate was introduced into the blunt ended BamHI-cleavage site by TA-cloning. Subsequently, the plasmid E1a-12S in pcDNA3.1(+) was linearized with EcoRV, T-ends added and the amplificate cloned into the IRES element. The thus obtained plasmid was subsequently linearized with XhoI, the ends made blunt ended and the EcoRI-EcoRI-cleavage product of YB-1 which is devoid of a stop codon.

The thus created construct E1A-12S-IRES-pcDNA3.1(+) was linearized using NotI and the ends made blunt ended. Also, the YB-1-EcoRI-cleavage product was made blunt ended and introduced into the dephosphorylated vector E1A-12S-IRES-pcDNA3.1(+). The cassette E1A-12S-IRES-YB-1 was removed using PmeI and cloned into the above described plasmid pGL3-E2-late after removal of the luciferase gene with NcoI and XbaI and blunt ending and dephosphorylation.

The cassette E2-late-E1A-12S-IRES-YB-1 was excised using PvuI and ClaI, the ends made blunt ended and cloned into the blunt ended and dephosphorylated NheI-cleavage site in the E3-region of E3E4-pShuttle (-NdeI)-AdEASY. The thus obtained construct is E2-late promoter-E1A-12S-IRES-YB-1-E3E4-pShuttle (-NdeI)-AdEASY.

Subsequently, the E2-late promoter-E1A-12S-IRES-YB-1-E3E4 cassette was excised from the E2-late promoter-E1A-12S-IRES-YB-1-E3E4-pShuttle (-NdeI)-AdEASY with SpeI and PacI and cloned into the SpeI and PacI cut pAdEASY. The resulting construct was referred to as E1a-12S-IRES-YB-1-E3E4-pAdEASY.

AdPSJL-12S-Yb-1-AdEASY was generated by homologous recombination upon transformation of BJ5183 (EC) bacteria with the plasmid Xvir-3'UTR in pShuttle AdEASY and E1a-12S-IRES-YB-1-E3E4-pAdEASY.
Cloning of the Cassette E2-late Promoter-E1A-12S and/or E2-late Promoter-E1A-12S-IRES-YB-1 in the E4-region After manipulation and deletion, respectively, of the E4 region using PstI 634 by were removed. The cassettes E2-late promoter-E1A-12S and/or E2-late promoter-E1A-12S-IRES-YB-1 can be introduced into the E4-region. Alternatively, the E2-region may remain intact under such conditions.
Cloning of the RGD-motive For an improved infectivity the HI loop of the fibre knob domain was modified according to Dmitriev et al. 1998 (An Adenovirus Vector with Genetically Modified Fibers Demonstrates Expanded Tropism via Utilization of a Coxsackievirus and Adenovirus Receptor-Independent Cell Entry Mechanism): The respective region was amplified using the primes RGD-Hpa fw (5'-GAGgtaacCTAAGCACTGCCAAG-3') (SEQ. ID. NO. 25), RGD-EcoRV rev (5'-CATAGAGTATGCAGATATCGT-TAGTGTTACAGGTTTAGTTTTG-3') (SEQ. ID. NO. 26) as well as RGD-EcoRV fw (5'-CAGCGACATGAActtaagT-GAGCTGC-3') (SEQ. ID. NO. 27) and RGD-Bfr rev (5'-CAGCGACATGAActtaagTGAGCTGC-3') (SEQ. ID. NO. 28), and an EcoRV-cleavage site thus generated. Paired oligonucleotides were cloned into this cleavage site which code for an Arg-Gly-Asp (RGD)- peptide with RGD oligo 1(5'-CACACTAAACGGTACACAGGAAACAG-GAGACACAACTTGTGACTGCCGCGGAGACT GTTTCTGCCC-3') (SEQ. ID. NO. 29), and RGD oligo 2(5'-GGGCAGAAACAGTCTCCGCGGCAGTCA-CAAGTTGTGTCTCCTGTTTCCTGTGTACCG TTTAGT-GTG-3') (SEQ. ID. NO. 30). Thus the RGD motif is contained in the HI loop of the fibre knob domain.

In FIGS. 30 and 31 the cloned E1B55k-3'UTR is described in more detail and the pE3/E4 Shuttle plasmid in the Adeasy system is depicted in FIG. 32. The plasmid is characterised in that manipulations and deletions, respectively, have been made to regions E3 and E4 which allow to clone different cassettes by means of different restriction site such as NheI for the E3 region and PstI for the E4 region without adversely affecting the open reading frames other than the one of E4orf6 and L5. Additionally, a sequence for the RGD motif is introduced into the region of the HI loop.

Positions of the deletions corresponding to the wildtype adenovirus sequence.
E3 deletion: 28138-30818
E4 deletion: 33246-33875
RGD motif: 32678 (9 amino acids introduced, central 3 amino acids RGD: CDCRGDCFC (SEQ. ID. NO. 31).

EXAMPLE 17

Infection of HeLa Cells with Adenovirus dl520

100.000 HeLa cells were plated per dish. At the next day the cells were infected with various titers (pfu/ml) of adenovirus dl520. The infection was done in 500 µl serum-free DMEM medium for 1 h at 37° C. Subsequently, the infection medium was removed and replaced by 2 ml complete medium (10% FCS/DMEM). After 3-5 days an analysis was performed using crystal violet staining.

The result of this experiment is depicted in FIG. 23. The adenovirus dl520 does not show any lysis at low MOIs (5-10 pfu/cell) upon infection of HeLa cells which do not have YB-1 in the nucleus. In contrast thereto, dl520 showed a factually complete lysis at an MOI (multiplicity of infection) of 100-200 pfu per cell and a still predominant lysis at an MOI of 50 pfu per cell. Therefrom it can be concluded that dl520 and similar viruses which are capable of switching on the adenoviral genes E1B55k and E4orf6 at higher MOIs, are suitable to transport either directly or indirectly overexpressed or deregulated YB-1 into the nucleus and thus to induce cell lysis.

EXAMPLE 18

Luciferase Assay for Determining the E2-late Promoter Activity

It is known that YB-1 binds to the adenoviral E2-late promoter in the nucleus (Holm et al., JBC 2002, 277, 10427-20434) and that this promoter is also well suited for the expression of nucleic acids. The use of the adenoviral E2-late promoter is particularly motivated by the fact that it can be regulated by YB-1, whereby YB-1 acts as a positive effector, i.e. the promoter is only active in the presence of YB-1 in the nucleus. Insofar said adenoviral E2-late promoter can be regulated in a highly selective manner and thus used in systems in which YB-1 is present in the nucleus and factually avoids any expression of the nucleic acid which is under the control of the adenoviral E2-late promoter in case that YB-1 is not present in the nucleus as an effector and regulator, respectively. The E2-late promoter comprises 3 Y-boxes (CCAAT) which are relevant for the activation of the E2 gene. Different E2-late promoter constructions have been prepared and tested for their specificity and activity. The analysis was carried out as follows.

The cell lines EPG-257 RDB (epithelial stomach carcinoma) which has YB-1 in the nucleus, HeLa (epithelial uterine cervix carcinoma) and U2OS (osteosarcoma) were seeded using three different cell concentrations in 6 well plates. The wells which showed confluence of 70% at the next day, were used for transfection. For each well 500 ng SpinMiniprep (Qiagen) purified plasmid DNA of the different E2-late promoter constructions in luciferase vectors (commercially available from Promega, starting plasmid: pGL3-enhancer) were added to 500 µl OptiMEM in a 1.5 ml locking cap reaction vessel and 5 µl DOTAP to 500 µl in a further locking cap reaction vessel. Both solutions were combined and mixed. The mixture was incubated for complex formation for 30 minutes at room temperature. The cells were rinsed three times with PBS and covered with a layer of the transfection mixture. The plates were incubated at 37° C. for 5 hours, subsequently rinsed again three times with PBS and provided with complete medium.

The cells were processed with the Luciferase Assay System Kit of Promega (Cat. No. E1500) 48 h after infection: Each well was provided with a layer of 500 µl lysis buffer, the cells rinsed off from the well plate with a 1 ml pipette after 10 minutes at room temperature and transferred into a 1.5 ml locking cap reaction vessel. The cell lysate was subsequently centrifuged at 4° C. for 15 minutes at 14.000 rpm. To each 50 µl of the supernatant 100 µl luciferase substrate were added and measured with TopCount (Canberra-Packard GmbH, 63303 Dreieich) Microplate Scintillation & Luminescence counter in black plates with 96 wells at a wave length of 945 nm.

Protein was measured with the BCA Protein Assay Reagent Kit, catalogue number 23227 (PIERCE, Rockford, Ill., USA) at 570 nm in a bioluminometer (Biolumin™ 960) kinetic fluorescence/absorbance plate reader of Molecular Dynamics. The relative light signals of the samples were translated into the protein amount (RLU/µg protein).

The following plasmids were used: pGL3-enhancer (Promega) from which the enhancer was removed by means of BamHI (2250 bp) and BsaBI (2003 bp), served as a blank reading. The various E2 promoter constructions were cloned into the MCS in the enhancer-lacking pGL3 vector by means of restriction sites Apa I and Sac I. The hCMV promoter was cloned by means of Bgl II and Hind III into the pGL3 enhancer and served as a positive control. The positive control allowed to estimate transfection efficiency and also served as a reference value for luciferase activity. For each cell line the CMV control was set 100% and the enzyme activity produced by the E2 promoter constructions put in relation thereto and depicted as a bar graph in FIG. 24.

The various constructs were referred to as follows:
1. comprising the Y-box I, II and III corresponding to bases 25932-26179 by (referring to the wildtype adenovirus sequence, see also the part of the subsequently provided adenoviral E2 region)

2. comprising the Y-box II and III corresponding to bases 25932-26127 by (referring to the wildtype adenovirus sequence, see also the part of the subsequently provided adenoviral E2 region)
3. comprising the Y-box III corresponding to bases 25932-26004 by (referring to the wildtype adenovirus sequence, see also the part of the subsequently provided adenoviral E2 region)
4. comprising no Y-box as acting as the blank reading Part of the Adenoviral E2 Region (Taken from Virology 1992, 186, 280-285)
(The YB-1 binding sites are printed in bold):

(SEQ. ID. No. 8)

```
25561 aggaactttatcctagagcgctcaggaatcttgcccgccacctgctgtgcacttcctagc
25621 gactttgtgcccattaagtaccgcgaatgccctccgccgctaggggccactgctaccctt
25681 ctgcagctagccaactaccttgcctaccactctgacataatggaagacgtgagcggtgac
25741 ggttactggagtgtcactccgctgcaacctatgcaccccgcaccgctccctggtttgc
25801 aattcgcagctgcttaacgaaagtcaaattatcggtacctttgagctgcagggtccctcg
25861 cctgacgaaaagtccgcggctccgggctgaaactcactccgggggctgtggacgtcggct
25921 taccttcgcaaatttgtacctgaggactaccacgcccacgagattaggttctacgaagag c
25981 caat cccgcccgccaaatgcggagcttaccgcctgcgtcattacccagggccacattctt
26041 gg ccaat gcaagccatcaacaaagcccgccaagagtttctgctacgaaagggacggggg
26101 gtttacttggaccccccagtccggcgaggagctcaad ccaat cccccgccgccgcagccc
26161 tatcagcagcagccgcgggcccttgcttcccaggatggcacccaaaaagaagctgcagct
26221 gccgccgccacccacggacgaggaggaatactgggacagtcaggcagaggaggttttgga
26281 cgaggaggaggaggacatgatggaagactgggagagcctagacgaggaagcttccgaggt
26341 cgaagaggtgtcagacgaaacaccgtcaccctcggtcgcattccctcgccggcgcccca
26401 gaaatcggcaaccggttccagcatggctacaacctccgctcctcaggcgccgccggcact
26461 gcccgttcgccgaccataccgtagatgggacaccactggaaccagggccggtaagtccaa
26521 gcagccgccgccgttagcccaagagcaacaacagcgccaaggctaccgctcatggcgcgg
26581 gcacaagaacgccatagttgcttgcttgcaagactgtgggggcaacatctccttcgcccg
26641 ccgctttcttctctaccatcacggcgtggccttcccccgtaacatcctgcattactaccg
26701 tcatctctacagcccatactgcaccggcggcagcggcagcggcagcaacagcagcggcca
26761 cacagaagcaaaggcgaccggatagcaagactctgacaaagcccaagaaatccacgcgg
```

The results presented in FIG. 24 confirm in an impressive manner that the individual promoter fragments which contain different E2-late/Y-boxes, are suitable for the expression of therapeutic transgenes in YB-1 nucleus-positive tumor cells and may thus be used as promoters in the meaning of the present invention.

EXAMPLE 19

Effect of YB-1 Expressed by Adenovirus on Particle Release

Human osteosarcoma cells (U2OS) were infected with the E1/E3-deleted adenoviral vector AdYB-1 and Ad312 only having E1A-deleted, at an MOI of 50 pfu/cell. AdYB-1 contains in its genome the sequence coding for the cellular transcription factor YB-1 and thus expresses the Y-box binding protein 1 (YB-1). In order to evaluate the release of viral particles as "plaque forming units" (pfu) after infection, either the supernatant of the culture medium or the remaining cell layer was isolated 2 and 5 days, respectively, post infectionem. The intracellular particles were released by 3 cycles of thawing/freezing. The particle number was analysed using the plaque assay on 293 cells.

The result is in depicted in FIG. 25, whereby the solid bars indicate the intracellular remaining viral particles, whereas the cross-striped bars represent the released, extracellular viral particles.

The result depicted in FIG. 25 confirms that AdYB-1, as a whole, produces more pfu than Ad312 and releases more particles. After 5 days the AdYB-1 infected cells clearly show a cytopathic effect (CPE) in contrast to Ad312-infected cells.

EXAMPLE 14

Replication of Adenovirus in Cells after Addition of Irinotecan

In order to determine the effect of Irinotecan on adenoviral replication $10^6$ U373 tumour cells were plated in 10 cm$^2$ Petri dishes. In a first reaction 5 µM Irinotecan was added after 24 hours. After another 24 hours the cells were infected with 10 pfu/cell dl520. After incubation of 3 days without Irinotecan DNA was isolated in accordance with the procedure described in example 10.

In a parallel reaction the thus prepared U373-cells were not pre-incubated with Irinotecan. After 48 hours of cultivating the cells without Irinotecan, they were infected with 10 pfu/ cell dl520 and subsequently incubated without Irinotecan for another 3 days. DNA was isolated as described above.

Subsequently 2 μg DNA were digested with restriction enzyme Kpn I and a Southern Blot analysis performed. A part of the adenoviral genome (position: 22734-24235) generated by means of PCR was used as a probe.

The result is depicted in FIG. 26. FIG. 26 shows that after incubation with Irinotecan adenoviral replication is significantly increased in U373 cells after treatment with Irinotecan (lane 2) compared to untreated control where no incubation with Irinotecan was performed (lane 1). This means that adenoviral replication is increased under the influence of Irinotecan.

EXAMPLE 15

Replication of Adenovirus in Cells after Administration of Trichostatin A

In order to test the effect of Trichostatin A on adenoviral replication, $10^6$ U373 tumour cells were plated in 10 cm$^2$ Petri dishes. After 24 hours 0.25, 0.5 and 0.75 μM Trichostatin A was added. After another 24 hours the cells were infected with 10 pfu/cell dl520.

After 3 days of incubation in medium without Trichostatin DNA was isolated. Subsequently 2 μg DNA were digested with restriction enzyme Kpn I and a Southern Blot analysis performed. A part of the adenoviral genome (position: 22734-24235) generated by means of PCR was used as a probe.

The result is depicted in FIG. 27. FIG. 27 shows that after incubation with increasing concentrations of Trichostatin A adenoviral replication in U373 cells (lanes 2, 3 and 4) is significantly increased compared to untreated controls where no incubation with Trichostatin A was performed (lane 1). This means that viral replication is increased under the influence of Trichostatin A.

EXAMPLE 16

Influencing the Expression of Coxsackievirus-adenovirus-receptor (CAR) on U373 Cells in Response to Addition of Trichostatin A 200,000 U373 cells were plated in 6 well plates. After 24 hours the cells were cultivated with 1 μM Trichostatin for 24 hours. After another 24 hours the cells were isolated. Subsequently, analysis of CAR expression was performed according to a standard protocol using Facs-analysis and the primary antibody anti-CAR clone RmcB from the company Upstate, and a rabbit-anti-mouse FITC as secondary antibody (company DAKO).

The result is depicted in FIG. 28. Without Trichostatin treatment 11.3% of the cells were CAR-positive, whereby after incubation of the cells with 1 μM Trichostatin 56.2% of the cells were CAR-positive. The figures are percentages of the overall cells used in the test.

From FIG. 28 it can be taken that under the influence of the histone deacylase inhibitor Trichostatin A CAR, which is an important factor for the binding of adenovirus, is expressed at a higher level and more available, respectively, which increases the efficacy of transfection of the thus treated cells.

EXAMPLE 23

Oncolysis of U373 Cells by Adenovirus after Combined Treatment of the Cells with Irinotecan and Trichostatin A 200,000 U373 cells were plated in a 6 well plate. After 24 hours either 2 μM Irinotecan or only 1 μM Trichostatin A or 1 μM Irinotecan+0.5 μM Trichostatin were added to the medium. After 24 hours of incubation the cells were infected with 10, 20 and 30 pfu/cell dl520. After 3-5 days the analysis was performed using crystal violet staining. The assays were performed in duplicate.

The result is depicted in FIG. 29. The six plates represented in panel 1 show a complete cell layer which was not affected by incubation with a combination of Irinotecan and Trichostatin A as shown by crystal violet staining. The next two wells of panel 1 show the cell layer after infection with 10 and 20 pfu/cell dl520, respectively. Also under such conditions there is no lysis of the cells which is due to the absence of replication of dl520. Thus it is shown that neither dl520 at 10 or 20 pfu/cells nor 1 μM Irinotecan+0.5 μM Trichostatin A alone are suitable to induce cell lysis.

The further 6 well plates 2, 3 and 4 depicted in FIG. 29, herein also referred to as panels 2, 3 and 4, were basically treated in accordance with this scheme. The individual wells were inoculated with U373 cells as previously described and the cells cultivated therein. The wells were inoculated with 10, 20 or 30 pfu/cell dl520 in duplicate, whereby the difference between the three 6 well plates resided in the kind of cytostatics used. In panel 2 2 μM Irinotecan, in panel 3 1 μM Trichostatin A and in panel 4 1 μM Irinotecan and 0.5 μM Trichostatin A was added to the individual wells.

In the 6 well plate 2 (panel 2) with 2 μM Irinotecan the cells were lysed with 30 pfu/cell dl520. In the 6 well plate 3 (panel 3) with 1 μM Trichostatin A the cells were lysed at 20 and 30 pfu/cell dl520. In the 6 well plate 4 (panel 4) with 1 μM Irenotecan+0.5 μM Trichostatin A the cells, in contrast thereto, were already lysed at 10 pfu/cell dl 520.

The test, the results of which are depicted in FIGS. 26 to 29, shows that the combination consisting of Irinotecan+Trichostatin A+dl520 induces a more effective cell lyses of tumour cells as any compound alone. This results, on the one hand, from Trichostatin A increasing CAR-expression and thus significantly improves infectability of the cells. On the other hand, Irinotecan translates YB-1 into the cell nucleus and thus induces an improved adenoviral replication. Additionally, the cellular YB-1 is assisting adenoviral replication after infection with dl520 and is no longer available for DNA-repair processes. Depending on the point of view, this results in an improved efficacy of dl520 on the one hand and an increased efficacy of the cytostatics on the other hand.

The features of the invention disclosed in the preceding specification, the claims as well as the figures can both individually as well as in any combination be important to the realisation of the invention in its various embodiments.

The invention claimed is:

1. A recombinant adenovirus, wherein upon infection of an eukaryotic cell, the adenovirus expresses a first polypeptide, wherein the first polypeptide is selected from the group comprising an E1B polypeptide, an E4 polypeptide, and a combination thereof, prior to expressing a second polypeptide, wherein the second polypeptide is an E1A polypeptide, whereby the E4 polypeptide is expressed prior to the E1A polypeptide.

2. The recombinant adenovirus of claim 1, wherein the E1B polypeptide is E1B 55 Kd polypeptide.

3. The recombinant adenovirus of claim 1, wherein the E4 polypeptide is E4orf6 polypeptide.

4. The recombinant adenovirus of claim 1, wherein the E1A polypeptide is E1A12S polypeptide.

5. The recombinant adenovirus of claim 1, further comprising a YB-1-controlled promoter, wherein the YB-1-controlled promoter is operably linked to at least one polynucleotide encoding the first or second polypeptide.

6. The recombinant adenovirus of claim 1, further comprising an E2 late promoter, wherein the E2 late promoter is operably linked to a polynucleotide encoding the second polypeptide.

7. The recombinant adenovirus of claim 1, further comprising a polynucleotide encoding a third polypeptide comprising YB-1 polypeptide that is not E1A.

8. The recombinant adenovirus of claim 1, wherein the first and the second polypeptides are expressed from a polynucleotide comprising an expression cassette.

9. The recombinant adenovirus of claim 8, wherein the second polypeptide is an E1A polypeptide, and a promoter operably linked to a polynucleotide encoding the second polypeptide is not an E1A promoter.

10. The recombinant adenovirus of claim 8, wherein the polynucleotide further encodes a third polypeptide comprising a YB-1 polypeptide.

11. The recombinant adenovirus of claim 10, wherein the polynucleotide encoding the third polypeptide is operably linked to a promoter comprising an E2 late promoter.

12. The recombinant adenovirus of claim 8, wherein the polynucleotide further comprises an IRES sequence, wherein the IRES sequence separates the nucleic acid sequences encoding the first and second polypeptides.

13. The recombinant adenovirus of claim 1, wherein the adenovirus is replication-deficient in non-tumor cells.

14. The recombinant adenovirus of claim 1, wherein the adenovirus is capable of replicating in cells comprising deregulated YB-1 or having YB-1 in the nucleus.

* * * * *